US012570747B2

(12) United States Patent
Throsby et al.

(10) Patent No.: US 12,570,747 B2
(45) Date of Patent: Mar. 10, 2026

(54) TGF-BETA-RII BINDING PROTEINS

(71) Applicant: Merus N.V., Utrecht (NL)

(72) Inventors: Mark Throsby, Utrecht (NL); Rinse Klooster, Utrecht (NL); Cornelis Adriaan De Kruif, Utrecht (NL)

(73) Assignee: Merus N.V., Utrecht (NL)

( * ) Notice: Subject to any disclaimer, the term of this patent is extended or adjusted under 35 U.S.C. 154(b) by 223 days.

(21) Appl. No.: 17/757,953

(22) PCT Filed: Dec. 22, 2020

(86) PCT No.: PCT/NL2020/050813
§ 371 (c)(1),
(2) Date: Jun. 24, 2022

(87) PCT Pub. No.: WO2021/133167
PCT Pub. Date: Jul. 1, 2021

(65) Prior Publication Data
US 2025/0270331 A1 Aug. 28, 2025

(30) Foreign Application Priority Data
Dec. 24, 2019 (NL) ..................................... 2024576

(51) Int. Cl.
*C07K 16/28* (2006.01)
(52) U.S. Cl.
CPC ...... *C07K 16/2863* (2013.01); *C07K 2317/76* (2013.01); *C07K 2317/92* (2013.01)
(58) Field of Classification Search
None
See application file for complete search history.

(56) References Cited

FOREIGN PATENT DOCUMENTS

| EP | 1245676 A1 | 10/2002 |
| WO | WO-2010053814 A1 | 5/2010 |
| WO | WO-2012093125 A1 | 7/2012 |
| WO | WO-2018075304 A1 | 4/2018 |
| WO | WO-2021133167 A1 | 7/2021 |

OTHER PUBLICATIONS

Ikeuchi et al., Nature Portfolio, 11:20624, https://doi.org/10.1038/s41598-021-98977-8, Oct. 2021.*
Uniprot Accession No. P01834, downloaded Jun. 11, 2025.*
Uniprot Accession No. P01857, downloaded Jun. 11, 2025.*
Bierie, B., et al., "TGF-beta and cancer," Cytokine Growth Factor Rev. 17(1-2):29-40, Elsevier, Netherlands (Feb. 2006).
Davidson, E., et al., "A high-throughput shotgun mutagenesis approach to mapping B-cell antibody epitopes," Immunology 143(1):13-20, American Association of Immunologists, United States (Sep. 2014).

Davies, J., et al., "Antibody VH Domains as Small Recognition Units," Biotechnology 13(5):475-479, Elsevier, Netherlands (May 1995).
De Haard, H.J., et al., "A large Non-immunized Human Fab Fragment Phage Library That Permits Rapid Isolation and Kinetic Analysis of High Affinity Antibodies," J Biol Chem. 274(26):18218-18230, American Society for Biochemistry and Molecular Biology, United States (Jun. 1999).
Dennler, S., et al., "Direct binding of Smad3 and Smad4 to critical TGF beta-inducible elements in the promoter of human plasminogen activator inhibitor-type 1 gene," EMBO J. 17(11):3091-3100, Springer, Germany (Jun. 1998).
Hao, Y., et al., "TGF-ß-Mediated Epithelial-Mesenchymal Transition and Cancer Metastasis," Int J Mol Sci. 20(11):2767, MDPI, Switzerland (Jun. 2019).
Hata, A., et al., "TGF-ß Signaling from Receptors to Smads," Cold Spring Harb Perspect Biol. 8(9):a022061, Cold Spring Harbor Laboratory Press, United States (Sep. 2016).
Hogrefe, H.H., et al., "A bacteriophage lambda vector for the cloning and expression of immunoglobulin Fab fragments on the surface of filamentous phage," Gene 128:119-26, Elsevier, Netherlands (Jun. 1993).
Hoogenboom, H.R., "Selecting and screening recombinant antibody libraries," Nat Biotechnol. 23(9):1105-16, Springer, Germany (Sep. 2005).
Hu, S., et al., "Minibody: A novel engineered anti-carcinoembryonic antigen antibody fragment (single-chain Fv-C$_H$3) which Exhibits Rapid, high-level targeting of Xenografts," Cancer Res. 56(13):3055-61, American Association for Cancer Research, United States (Jul. 1996).
Hu, X., et al., "Cloning, expression and characterisation of a single-chain Fv antibody fragment against domoic acid in *Escherichia coli*," J Biotechnol. 120(1):38-45, Elsevier, Netherlands (Oct. 2005).
Huston, J.S., et al., "Protein engineering of antibody binding sites: Recovery of specific activity in an anti-digoxin single-chain Fv analogue produced in *Escherichia coli*," Proc Natl Acad Sci U S A. 85(16):5879-83, National Academy of Sciences, United States (Aug. 1988).
International Search Report and Written Opinion for International Application No. PCT/NL2020/050813, European Patent Office, Netherlands, mailed on Mar. 26, 2021, 14 pages.
Jespers, L., et al., "Aggregation-resistant domain antibodies selected on phage by heat denaturation," Nat Biotechnol. 22(9):1161-5, Springer, Germany (Sep. 2004).
Jung, B., et al., "Transforming Growth Factor ß Superfamily Signaling in Development of Colorectal Cancer," Gastroenterology 152(1):36-52, Elsevier, Netherlands (Jan. 2017).
Kim, D.Y., et al., "Antibody light chain variable domains and their biophysically improved versions for human immunotherapy," MAbs. 6(1):219-35, Taylor & Francis, United Kingdom (Jan. 2014).

(Continued)

*Primary Examiner* — Marianne P Allen
(74) *Attorney, Agent, or Firm* — Sterne, Kessler, Goldstein & Fox P.L.L.C.

(57) ABSTRACT

The present invention relates to an antibody or antibody fragment thereof that specifically binds to the extracellular domain of human TGF-βRII. The present invention further relates to a vector comprising a polynucleotide encoding the antibody or antibody fragment of the invention, an isolated cell producing the antibody or antibody fragment of the invention, and a pharmaceutical composition comprising the antibody or antibody fragment of the invention. The antibody or antibody fragment of the invention can be used to treat cancer.

35 Claims, 12 Drawing Sheets
Specification includes a Sequence Listing.

(56) References Cited

OTHER PUBLICATIONS

Kim, Y.P., et al., "Effective therapeutic approach for head and neck cancer by an engineered minibody targeting the EGFR receptor," PLoS One. 1:9(12), PLOS, United States (Dec. 2014).

Kruskal, J.B., "An overview of sequence comparison: Time warps, string edits and macromolecules," D. Sankoff and J. B. Kruskal, (ed.), pp. 1-44, Society for Industrial and Applied Mathematics, United States (Apr. 1983).

Lilley, G.G., et al., "Recombinant single-chain antibody peptide conjugates expressed in *Escherichia coli* for the rapid diagnosis of HIV," J Immunol Methods. 171(2):211-26, Elsevier, Netherlands (May 1994).

Marks, J.D., et al., "By-passing immunization. Human antibodies from V-gene libraries displayed on phage," J Mol Biol. 222(3):581-97, Elsevier, Netherlands (Dec. 1991).

Porter, R.R., "The hydrolysis of rabbit y-globulin and antibodies with crystalline papain," Biochem J. 73(1):119-26, Biochemical Society, United Kingdom (Sep. 1959).

Quail, D.F., et al., "Microenvironmental regulation of tumor progression and metastasis," Nat Med. 19(11):1423-37, Springer, Germany (Nov. 2013).

Siegel, P.M., "Cytostatic and apoptotic actions of TGF-beta in homeostasis and cancer," Nat Rev Cancer 3(11):807-21, Springer, Germany (Nov. 2003).

Smith, G.P., "Filamentous fusion phage: novel expression vectors that display cloned antigens on the virion surface," Science 228(4705):1315-7, American Association for the Advancement of Science, United States (Jun. 1985).

Tanha, J., et al., "Optimal design features of camelized human single-domain antibody libraries," J Biol Chem. 276(27):24774-80, American Society for Biochemistry and Molecular Biology, United States (Jul. 2001).

Thompson, J.D., et al., "Clustal W: Improving the sensitivity of progressive multiple sequence alignment through sequence weighting, position-specific gap penalties and weight matrix choice," Nucleic Acids Res. 22(22):4673-80, Oxford University Press, United Kingdom (Nov. 1994).

To, R., et al., "Isolation of monomeric human V(H)s by a phage selection," J Biol Chem. 280(50):41395-403, American Society for Biochemistry and Molecular Biology, United States (Dec. 2005).

Valedkarimi, Z., et al., "Production and characterization of anti-human IgG F(ab')2 antibody fragment," Hum Antibodies 26(4):171-176, IOS Press BV, Netherlands (Dec. 2018).

Vander Ark, A, et al., "TGF-ß receptors: In and beyond TGF-ß signaling," Cell Signal 52:112-120, Elsevier, Netherlands (Dec. 2018).

Wieland, W.H., et al., "Display and selection of chicken IgA Fab fragments," Vet Immunol Immunopathol. 110(1-2):129-40, Elsevier, Netherlands (Mar. 2006).

Guimond, A., et al., "Mapping of putative binding sites on the ectodomain of the type II TGF-beta receptor by scanning-deletion mutagenesis and knowledge-based modeling," *FEBS Lett* 456(1):79-84, Federation of European Biochemical Societies & Wiley, United Kingdom (1999).

* cited by examiner

IGKV1-39 (SEQ ID NO: 99)

DIQMTQSPSSLSASVGDRVTITCRASQSISSYLNWYQQKPGKAPKLLIYAASSLQSGVPSRFSG
SGSGTDFTLTISSLQPEDFATYYCQQSYSTP

Figure 1B

IGKV1-39/jk1 (SEQ ID NO: 16)

DIQMTQSPSSLSASVGDRVTITCRASQSISSYLNWYQQKPGKAPKLLIYAASSLQSGVPSRFSG

SGSGTDFTLTISSLQPEDFATYYCQQSYSTPPTFGQGTKVEIK

Figure 1C

IGKV1-39/jk5 (SEQ ID NO: 100)

DIQMTQSPSSLSASVGDRVTITCRASQSISSYLNWYQQKPGKAPKLLIYAASSLQSGVPSRFSG
SGSGTDFTLTISSLQPEDFATYYCQQSYSTPPITFGQGTRLEIK

Figure 2
Figure 2A
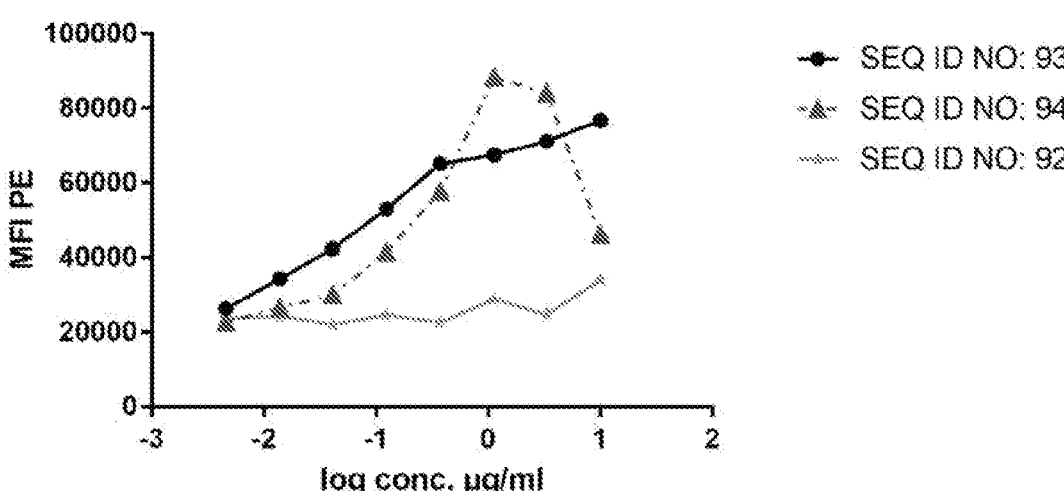
Figure 2B
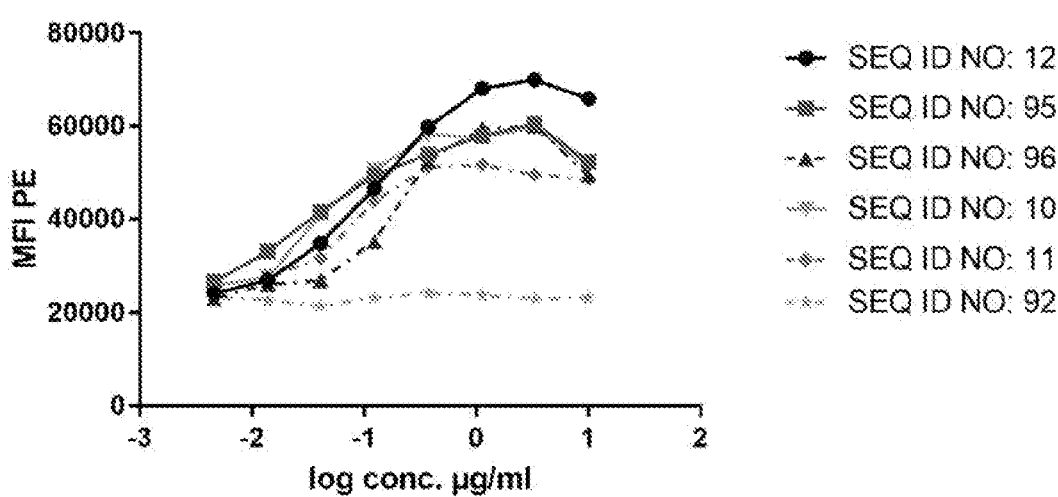

Figure 3
Figure 3A
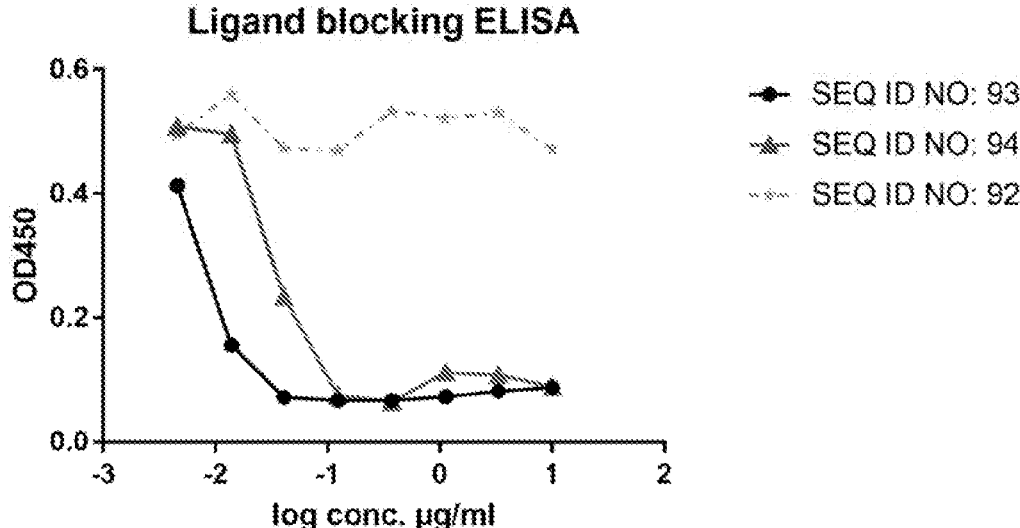
Figure 3B
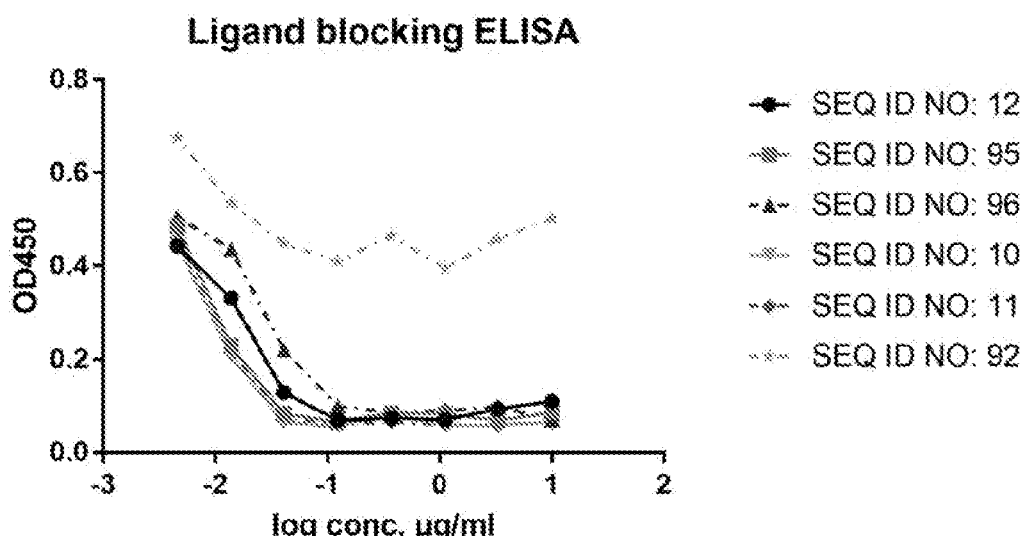

Figure 4

| SEQ ID NO: | | 1 ........10 ........20 ........30 ........40 ........50 ........60 ........70 ........80 ........90 .......100 .......110 .......120 |
|---|---|---|
| 12 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........GDPWGQGTLVTVSS |
| 57 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 58 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 59 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 60 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 61 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 62 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 63 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 64 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 65 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 66 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 67 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 68 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 69 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 70 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 71 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 72 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 73 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 74 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 75 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 76 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 77 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 78 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 79 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 80 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 81 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 82 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 83 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 84 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 85 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 86 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 87 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 88 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 89 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 90 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |
| 91 | (1) | QVQLVESGGGLVQPGGSLRLSCAVSGFRYAMSWVRQAPGKGLEWVSAISA..GD..NTDSVKGRFSISRDNSKNTLYLQMNSLRAEDTAVYFCAKG........FDPWGQGTLVTVSS |

Figure 7
Figure 7A
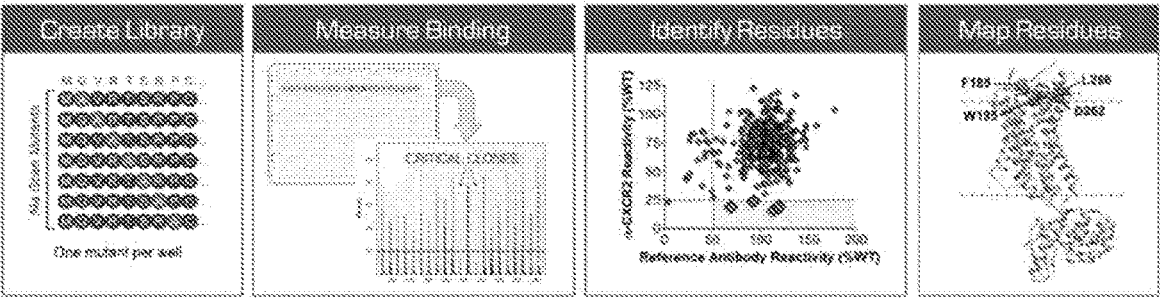
Figure 7B
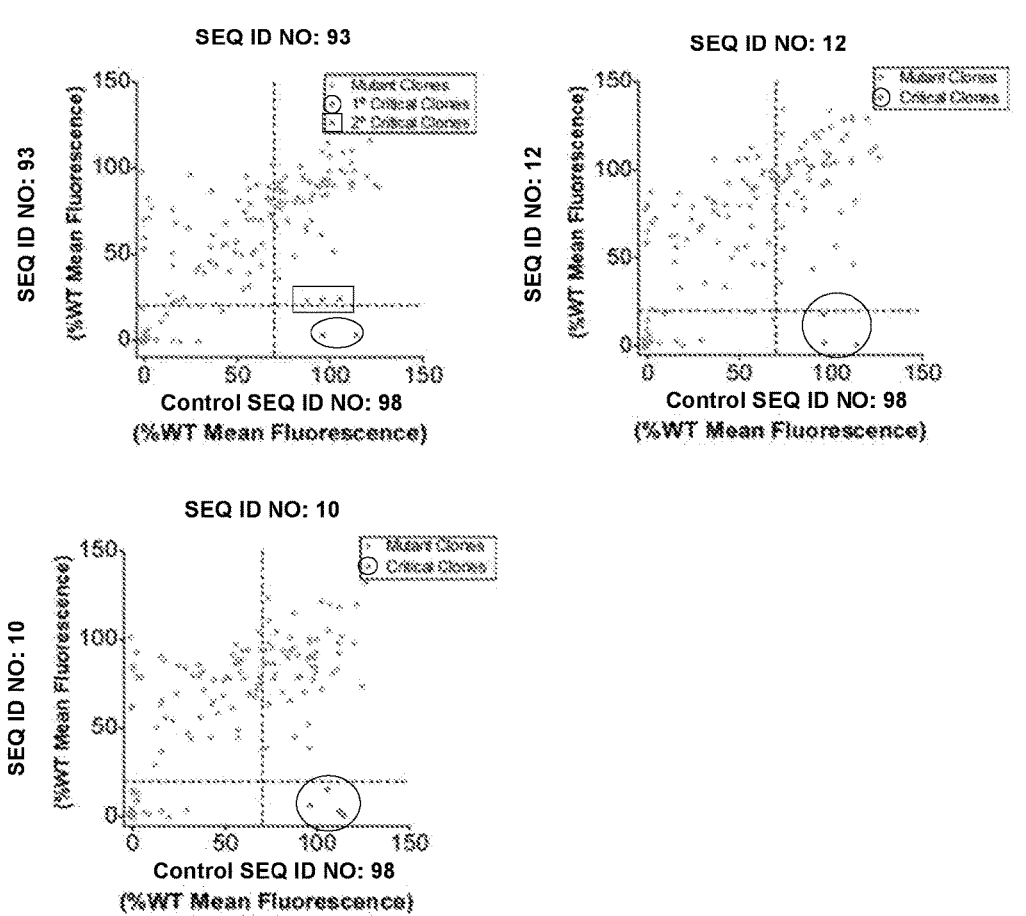

| Binding Reactivity (% WT) | | | | |
|---|---|---|---|---|
| Mutation | SEQ ID NO: 93 | SEQ ID NO: 12 | SEQ ID NO: 10 | SEQ ID NO: 98 |
| F25A | 2.28 (0) | 1.5 (0) | 6.6 (1) | 96.3 (41) |
| L28A | 22.8 (2) | 94.2 (10) | 44.9 (2) | 88.1 (11) |
| T52A | 23.4 (9) | 17.9 (13) | 38.6 (13) | 96.1 (13) |
| I54A | 24 (0) | 75.9 (28) | 15.4 (3) | 105.5 (22) |
| D119A | 2.8 (3) | 1 (1) | 0.6 (0) | 114.3 (14) |
| E120A | 91.5 (9) | 46.6 (2) | 2.9 (1) | 112.3 (6) |

SEQ ID NO: 93        SEQ ID NO: 12

SEQ ID NO: 10

TGF-BETA-RII BINDING PROTEINS

CROSS-REFERENCE TO RELATED APPLICATIONS

This application is a U.S. national stage filing of International Application No. PCT/NL2020/050813, filed Dec. 22, 2020; which claims priority to NL Application No. 2024576, filed Dec. 24, 2019. The entire contents of International Application No. PCT/NL2020/050813 are hereby incorporated herein by reference.

REFERENCE TO A SEQUENCE LISTING SUBMITTED ELECTRONICALLY VIA EFS-WEB

This application includes a Sequence Listing submitted electronically via EFSWeb (name: "4096_0440001_Seglisting_ST25.txt"; size: 123,857 bytes; and created on: Dec. 12, 2022), which is hereby incorporated by reference in its entirety.

FIELD OF THE INVENTION

The present invention relates to the field of medicine. More specifically, the present invention relates to proteins that bind transforming growth factor-beta receptor II (TGF-βRII) and their use in the treatment of humans, in particular in the treatment of cancer.

BACKGROUND TO THE INVENTION

Transforming Growth Factor-β (TGF-β) is a signaling molecule part of the TGF-β superfamily. There are three TGF-β ligands (TGF-β1, 2 and 3) that regulate a variety of cellular functions. TGF-β signaling has a tumor-suppressive role in normal cells but is capable of having a tumor-promoting role in malignant cells. They play a role in processes such as proliferation, migration, differentiation, apoptosis, angiogenesis and epithelial-mesenchymal transition (Bierie and Moses, 2006. Siegel and Massague, 2003). These signals are mediated through the binding to TGF-β receptor type-2 (TGF-βRII), which leads to the dimerization with and phosphorylation of TGF-βRI. This heterotetrameric complex composed of two TGF-βRII and two TGF-βRI then recruits and phosphorylates SMAD2 and SMAD3, which in turn recruits and binds to the co-SMAD molecule SMAD4 to form the SMAD/co-SMAD complex, and translocates to the nucleus where it regulates the transcription of TGF-β target genes (Hata and Chen, 2016. Vander Ark, Cao et al., 2018).

High levels of TGF-β expression have been shown to be associated with a poor prognosis in cancer. TGF-β may induce epithelial-mesenchymal transition which facilitates the migration and metastasis of cancer cells. Gene expression profiles have indicated that TGF-β signaling is a significant pathway in liver metastases of colorectal cancer (Jung, Staudacher et al., 2017). Furthermore, it has been reported that stromal-epithelial interactions play roles in cancer progression. An abundant stromal cellular component found in solid tumors, is the cancer associated fibroblast (CAF), which aside from building and remodeling the extracellular matrix that may serve as a scaffold for the tumor, also contributes to immune evasion, as well as promotes tumor development and growth (Quail and Joyce, 2013). Tumor-derived TGF-β1 induces the transdifferentiation of fibroblasts into the 'activated' CAFs by binding to TGFβRII, which is capable of promoting a pro-tumorigenic stromal environment.

Existing modes of targeting the TGF-β signaling pathway to inhibit aberrant TGF-β signaling characteristics of CAFs and tumors to date have had sub-optimal efficacy and/or development liabilities. One anti-TGF-βRII monoclonal antibody is LY3022859 disclosed in WO2010/053814, which was reported to block the ectodomain of TGF-βRII. However, dose escalation studies in phase I led to cytokine release syndrome and was considered unsafe in patients with advanced solid tumors. Another agent, disclosed in WO2012/093125, is an anti-TGF-βRII single variable domain with shorter half-life and wherein the precise mechanism of action or binding domain of this molecule has not been established. To date there has been no anti-TGF-βRII antibody which has successfully gone through clinical trials as the complexity and pleiotropic nature of TGF-β tumor regulation renders the drug development challenging (Hao, Baker et al., 2019). Herein, we describe new heavy chain variable regions, heavy chains, Fabs and full-length IgG monospecific antibodies capable of binding TGF-βRII. These antibodies, or antibodies comprising these heavy chains or heavy chain variable regions, target a novel position on TGF-βRII, and block the interaction between the receptor and its ligand, which is an improvement over existing antibodies.

SUMMARY OF THE INVENTION

The object of the present invention is to provide a new pharmaceutical agent for the treatment of human disease, in particular for the treatment of cancer. This object is met by the provision of an antibody or antibody fragment thereof, and particular binding domains, that specifically binds to the extracellular domain of human TGF-βRII, as described and claimed herein.

In a first aspect, the present invention relates to an antibody or antibody fragment thereof that specifically binds to the extracellular domain of human TGF-βRII, wherein the antibody or antibody fragment binds to an epitope of the extracellular domain of human TGF-βRII of which phenylalanine (F) at position 25 of isoform A of human TGF-βRII, or at position 50 of isoform B of human TGF-βRII, is a critical residue for binding.

Preferably, such antibody or antibody fragment binds to TGF-βRII, blocks or inhibits binding of a human TGF-β to a human TGF-βRII, thereby inhibiting the signal transduction into the cell, and blocking or inhibiting heterodimerization of TGF-βRII.

In a second aspect, the present invention relates to a vector comprising a polynucleotide encoding either or both the heavy chain and the light chain of the antibody or antibody fragment as described herein.

In a third aspect, the present invention relates to a cell producing the antibody or antibody fragment as described herein.

In a fourth aspect, the present invention relates to a pharmaceutical composition comprising the antibody or antibody fragment as described herein and a pharmaceutically acceptable carrier, diluent, or excipient.

In a fifth aspect, the present invention relates to a pharmaceutical agent for preventing, suppressing symptom progression or recurrence of, and/or treating cancer, wherein the pharmaceutical agent comprises the antibody or antibody fragment as described herein as an active ingredient.

In a sixth aspect, the present invention relates to a method of treating cancer in a subject, the method comprising administering an effective amount of the antibody or antibody fragment as described herein, or the pharmaceutical composition as described herein, to the subject.

In a seventh aspect, the present invention relates to a method of blocking binding of human TGF-β to human TGF-βRII on a cell, the method comprising providing the antibody or antibody fragment as described herein to the cell and allowing the antibody or antibody fragment to bind to the human TGF-βRII of the cell, to thereby block binding of human TGF-β to human TGF-βRII on the cell.

In an eighth aspect, the present invention relates to a method of inhibiting signal transduction into a cell induced by binding of a human TGF-β to a human TGF-βRII of the cell, the method comprising providing the antibody or antibody fragment as described herein to the cell and allowing the antibody or antibody fragment to bind to the human TGF-βRII of the cell, to thereby inhibit the signal transduction into the cell.

In a ninth aspect, the present invention relates to a method of preventing or inhibiting metastasis, the method comprising administering an effective amount of the antibody or antibody fragment as described herein, or the pharmaceutical composition as described herein, to a subject.

DETAILED DESCRIPTION OF THE INVENTION

In general, the present invention relates to a protein, in particular an antibody or antibody fragment thereof, that specifically binds to the extracellular domain of human TGF-βRII. Preferably, the antibody is isolated. Preferably, the antibody is a monoclonal antibody. More preferably, the antibody is an isolated monoclonal antibody.

An "isolated monoclonal antibody" refers to an antibody produced by a clonal cell. Examples of isolated antibodies include, but are not limited to, an antibody that has been affinity purified, an antibody that has been produced in a hybridoma or other cell line in vitro, and a human antibody derived from a transgenic non-human animal.

The term "antibody" refers to an immunoglobulin molecule comprising four polypeptide chains: two heavy (H) chains and two light (L) chains. Each heavy chain comprises a heavy chain variable region (VH) and a heavy chain constant region (CH). The heavy chain variable region comprises three heavy chain complementarity determining regions (HCDRs) and four framework regions (FRs), and is preferably human or humanized. The heavy chain constant region is comprised of three domains: CH1, CH2 and CH3; and may be derived from any organism, preferably a human. The CH1 and CH2 domains of the heavy chain constant region are connected through a flexible hinge region. Each light chain comprises a light chain variable region (VL) and a light chain constant region (CL). The light chain variable region can be of two types: kappa (K) or lambda (λ) and, like the VH, comprises three light chain complementarity determining regions (LCDRs) and four framework regions. The light chain variable region is preferably human or humanized. The light chain constant region is comprised of one domain: CL; and may be derived from any organism, preferably a human. The two heavy chains are linked to each other by disulfide bonds between the two hinge regions, and each heavy chain pairs with a light chain by a disulfide bond between the CH1 and CL regions. In a conventional antibody, the two heavy chains and the two light chains are identical, providing the antibody with two identical antigen-binding sites.

Antibody binding has different qualities including specificity and affinity. The specificity determines which antigen or epitope thereof is specifically bound by an antibody binding domain. The affinity is a measure for the strength of binding to a particular antigen or epitope.

A "human" antibody refers to an antibody in which all antibody domains are derived from human germline immunoglobulin sequences. The human antibody to be used in the present invention can be produced by a method using a mouse transformed to produce a human antibody, e.g., Humab mouse, a KM mouse, a Xeno mouse, a Tc mouse, or a MeMo® mouse (WO2009/157771). The human antibody can also be prepared using SCID mice into which human immune cells have been reconstructed such that a human antibody response is made upon immunization.

A "humanized" antibody region refers to an antibody prepared by, e.g., grafting a complementarity determining region (CDR) sequence of an antibody derived from a germline of an animal other than human, such as mouse or chicken, into human framework sequences of a human antibody. Also, a humanized antibody can be produced by linking nucleic acid encoding CDR regions of an antibody isolated from antibody-producing hybridoma's to a nucleic acid encoding a framework region of the human-derived antibody using a well-known method.

An antibody is capable of binding an antigen through its heavy chain and/or light chain variable regions, and in particular through its specific CDRs. The CDRs of the heavy and/or light chain variable regions of an antibody bind to an "epitope", also referred to as "antigenic determinant", of an antigen. Epitopes can be formed from contiguous amino acids or noncontiguous amino acids juxtaposed by tertiary folding of a protein, so-called linear and conformational epitopes, respectively. Epitopes formed from contiguous, linear amino acids are typically retained on exposure to denaturing solvents, whereas epitopes formed by tertiary folding, conformation is typically lost on treatment with denaturing solvents. An epitope may typically include 3, 4, 5, 6, 7, 8, 9, 10, 11, 12, 13, 14 or 15 amino acids in a unique spatial conformation.

An "antigen" typically is a molecule capable of inducing an immune response in a host organism, thereby producing antibodies with specificity for the antigen. At the molecular level, an antigen is characterized by its ability to be bound by the antigen-binding site of an antibody. As described above, the antigen-binding site of an antibody is formed by its heavy and/or light chain variable regions, and in particular by its CDRs. An antigen comprises at least one, but often more, epitopes.

Also mixtures of antigens can be regarded as an 'antigen', and the ordinary skilled person would appreciate that sometimes a lysate of tumor cells, or viral particles may be indicated as 'antigen' whereas such tumor cell lysate or viral particle preparation exists of many antigenic determinants.

In the present invention, the antigen is human TGF-βRII. Human TGF-βRII is a transmembrane protein of which there are different isoforms. The amino acid sequence of human TGF-βRII isoform A is provided as SEQ ID NO: 101; the amino acid sequence of the extracellular domain of human TGF-βRII isoform A is provided as SEQ ID NO: 102. Human TGF-βRII isoform B is a splice variant encoding a longer isoform due to an insertion in the extracellular domain. The amino acid sequence of human TGF-βRII isoform B is provided as SEQ ID NO: 103; the amino acid sequence of the extracellular domain of isoform B of human TGF-βRII is as set forth in SEQ ID NO: 104.

TGF-βRII is a member of the serine/threonine protein kinase family and the TGFB receptor subfamily. It is known under various synonyms, including TGFBR2, AAT3, FAA3, LDS1B, LDS2, LDS2B, MFS2, RIIC, TAAD2, TGFR-2, TGFbeta-RII, transforming growth factor beta receptor 2, and TBR-ii, TBRII. TGF-βRII forms a heterodimeric complex with another receptor protein, and binds TGF-beta. This receptor/ligand complex phosphorylates proteins, which then enter the nucleus and regulate the transcription of a subset of genes related to cell proliferation.

An antibody binds an antigen with a particular binding affinity. The "binding affinity" is determined by the dissociation constant ($K_D$), calculated by the formula: $k_{off}/k_{on}$, and refers to the strength of the antibody-antigen interaction. Depending on the desired biological activity, an antibody can be selected based on its high and/or low $k_{on}$ and/or $k_{off}$ rates.

An "antibody fragment" includes, but is not limited to, a functional fragment of a heavy chain and/or a light chain. Such functional fragment comprises at least one CDR derived from, or synthesized based on, a CDR from an antibody heavy chain or light chain, and is capable of specifically recognizing an antigen. An antibody fragment can for instance be, but is not limited to, a Fab, F(ab')₂, scFv, minibody, or sdAb. An "antibody fragment" further refers to a proteinaceous moiety comprising a functional part of an antibody. In the present case at least the heavy chain variable region, or one or more of the HCDRs, described herein. The antibody fragment can be any binding agent, including, but not limited to, single chain Fvs, single chain or Tandem diabodies (TandAb®), VHHs, Anticalins®, Nanobodies®, a BiTE®, a Fab, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins® or a KALBITOR®.

A "Fab" typically means a binding domain comprising a heavy chain variable region, a light chain variable region, a CH1 and a CL region.

A "F(ab')₂" typically means a binding domain comprising two Fab domains linked to each other by means of a hinge region.

A "single-chain variable fragment" (scFv) typically means a binding domain comprising a VH domain and a VL domain which are connected via a linker, for example a peptide linker of, for example, from about 10 to about 25 amino acids in length.

A "minibody" typically means a binding domain comprising two scFv's and a CH3 domain.

A "single domain antibody" (sdAb) typically means a binding domain comprising only the VH or the VL domain of an antibody, usually fused or otherwise linked to, part of, an Fc region. Like a whole antibody, it is able to bind selectively to a specific antigen. Single-domain antibody fragments may be engineered from heavy-chain antibodies found in camelids; these are at times called VHH fragments (Nanobodies®). Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single domain antibodies is currently based on heavy chain variable domains, nanobodies derived from light chains have also been shown to be capable of binding to target epitopes. Nanobodies are therefore also encompassed by the invention.

An "antibody fragment" also refers to at least one CDR, wherein the at least one CDR is part of a protein construct that exhibits binding specificity for an antigen. Preferably, the at least one CDR is HCDR3. In one embodiment, the protein construct comprises HCDR1, HCDR2 and HCDR3. In another embodiment, the protein construct comprises HCDR1, HCDR2, HCDR3, LCDR1, LCDR2 and LCDR3. The protein construct may further comprise, part of, an Fc region, including CH2 and/or CH3. The protein construct may also comprise a CH1 region. The CH1, CH2 and/or CH3 regions may be engineered to obtain any desired properties with respect to antigen binding and/or effector function.

The invention also encompasses variants of the antibody or antibody fragment of the invention. A "variant" of the antibody or antibody fragment of the invention comprises at least a functional part of the antibody or antibody fragment as described herein, or a derivative or analogue thereof. Such functional part, derivative or analogue comprises at least the binding domain of the antibody or antibody fragment described herein, including the heavy chain variable region and/or light chain variable region comprising the CDRs as disclosed herein. A variant may comprise one to five amino acid substitutions in one or more of the CDRs. For instance, an amino acid residue may be substituted with a conservative amino acid residue. A variant may also comprise one or more amino acid substitutions in the one or more framework regions. Preferably, the variant comprises a VH region that has at least 80%, 85%, 90%, 92%, 94%, 96%, 97%, 98%, or 99% sequence identity to the VH amino acid sequence of the antibody or antibody fragment of the invention. Preferably, the variant comprises a VL region that has at least 80%, 85%, 90%, 92%, 94%, 96%, 97%, 98%, or 99% sequence identity to the VL amino acid sequence of the antibody or antibody fragment of the invention.

"Percent (%) identity" as referring to nucleic acid or amino acid sequences herein is defined as the percentage of residues in a candidate sequence that are identical with the residues in a selected sequence, after aligning the sequences for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley).

In particular, percent sequence identity according to the invention set out herein between two nucleic acid sequences may be determined using the AlignX application of the Vector NTI Program Advance 11.5.2 software using the default settings, which employ a modified ClustalW algorithm (Thompson, J. D., Higgins, D. G., and Gibson T. J.

(1994) Nuc. Acid Res. 22: 4673-4680), the swgapdnamt score matrix, a gap opening penalty of 15 and a gap extension penalty of 6.66. Amino acid sequences may be aligned with the AlignX application of the Vector NTI Program Advance 11.5.2 software using default settings, which employ a modified ClustalW algorithm (Thompson, J. D., Higgins, D. G., and Gibson T. J., 1994), the blosum62mt2 score matrix, a gap opening penalty of 10 and a gap extension penalty of 0.1.

A variant maintains the binding specificity of the antibody or antibody fragment of the invention, for example the antigen specificity. The binding affinity of the variant may, however, be different than that of the original antibody or antibody fragment of the invention. The variant may, for instance, have a lower or higher $K_{on}$ and/or $K_{off}$ rate than the antibody or antibody fragment as described herein.

A functional derivative of the antibody or antibody fragment of the invention can be an antibody mimetic, a polypeptide, an aptamer or a combination thereof. These proteins or aptamers typically bind to one target. It is to be understood that any combination of these antibodies, antibody mimetics, polypeptides and aptamers can be linked together by methods known in the art. For example, in some embodiments the antibody or antibody fragment of the invention is a conjugate or part of a fusion protein.

An antibody mimetic is a polypeptide that, like antibodies, can specifically bind an antigen, but that is not structurally related to antibodies. Antibody mimetics are usually artificial peptides or proteins with a molar mass of about 3 to 20 kDa. Non-limiting examples of antibody mimetics are affibody molecules (typically based on the Z domain of Protein A); affilins (typically based on Gamma-B crystalline or Ubiquitin); affimers (typically based on Cystatin); affitins (typically based on Sac7d from *Sulfolobus acidocaldarius*); alphabodies (typically based on Triple helix coiled coil); anticalins (typically based on Lipocalins); avimers (typically based on A domains of various membrane receptors); DARPins (typically based on ankyrin repeat motif); fynomers (typically based on SH3 domain of Fyn 7); kunitz domain peptides (typically based on Kunitz domains of various protease inhibitors); and monobodies (typically based on type III domain of fibronectin).

Monobodies are synthetic binding proteins that are constructed using a fibronectin type III domain (FN3) as a molecular scaffold. Monobodies are an alternative to antibodies for creating target-binding proteins. Monobodies and other antibody mimetics are typically generated from combinatorial libraries in which portions of the scaffold are diversified using molecular display and directed evolution technologies such as phage display, mRNA display and yeast surface display.

Aptamers are oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecules.

An antibody of the invention is preferably an IgG antibody, preferably an IgG1 or an IgG4 antibody. Most preferably, the antibody is an IgG1 antibody. Such full length IgG antibody is preferred because of its favorable half-life and the desire to stay as close to fully autologous (human) molecules for reasons of immunogenicity. IgG1 is favored based on its long circulatory half-life in man.

The term 'full length IgG' or 'full length antibody' according to the invention is defined as comprising an essentially complete IgG, which however does not necessarily have all functions of an intact IgG. For the avoidance of doubt, a full length IgG contains two heavy and two light chains. Each chain comprises constant (C) and variable (V) regions, which can be broken down into domains designated CH1, CH2, CH3, VH, and CL, VL. An IgG antibody binds to antigen via the variable region domains contained in the Fab portion, and after binding can interact with molecules and cells of the immune system through the constant domains, mostly through the Fc portion. Full length antibodies according to the invention encompass IgG molecules wherein mutations may be present that provide desired characteristics.

A full length IgG may contain variations in the constant regions to modulate effector function, both increasing and mitigating such functions, including antibody-dependent cellular cytotoxicity (ADCC), or cellular dependent cytotoxicity (CDC), to increase homo- or heterodimerization for generating monospecific or multispecific antibodies from host cells comprising a nucleic acid encoding different heavy chains, and to facilitate separation of antibodies or antibody fragments produced by such host cells.

For instance, leucine at position 235 according to the EU numbering system may be substituted with glycine, and/or glycine at position 236 according to the EU numbering system may be substituted with arginine. Such modification(s) ensure that binding to an Fc receptor and/or effector function is eliminated or decreased. Other variations of the CH2 and Fc region are known in the art to the same effect are also encompassed within the present invention.

Full length IgG should not have deletions of substantial portions of any of the regions. However, IgG molecules wherein one or several amino acid residues are deleted, without essentially altering the binding characteristics of the resulting IgG molecule, are embraced within the term "full length IgG". For instance, such IgG molecules can have a deletion of between 1 and 10 amino acid residues, preferably in non-CDR regions, wherein the deleted amino acids are not essential for the binding specificity of the IgG.

For instance, lysine at position 447 according to the EU numbering system may be deleted. Such deletion reduces the heterogeneity of the antibody. Furthermore, in order to suppress the swapping in an IgG4 antibody molecule, serine located in the hinge region at position 228 according to the EU numbering system may be substituted with proline.

Suitable light chains for use in an antibody or antibody fragment of the invention include a light chain that is produced in response to immunization with an antigen, referred to as a cognate light chain, or a synthetically produced light chain based thereon. A suitable light chain also includes a common light chain (cLC), such as those that can be identified by screening for the most commonly employed light chains in existing antibody libraries (wet libraries or in silico), where the light chains do not substantially interfere with the affinity and/or selectivity of the epitope-binding domains of the heavy chains, but are also suitable to pair with an array of heavy chains. A common light chain is preferably encoded by germline sequences of V- and J gene segments which are rearranged but have not, or minimally, undergone somatic hypermutation. For example, a suitable light chain includes one from a transgenic non-human animal, such as MeMo® having a common light chain integrated into its genome and which can be used to generate large panels of common light chain antibodies having diversity at the heavy chain and are capable of specifically binding an antigen upon exposure to said antigen.

The term "common light chain" thus refers to a light chain that can be associated with two or more different heavy chains and exhibits binding ability to an antigen (see for instance WO2009/157771, WO2019/190327 and WO2014/051433). A preferred light chain V gene for such a common light chain is IGKV1-39. Preferred light chain J genes are jk1 and jk5. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org. Preferred examples of a common light chain include a light chain encoded by a human κ light chain IgVκ1-39*01/IGJκ1*01 (nomenclatures of IMGT database) germline gene (hereinafter, abbreviated as the "IGVK1-39/JK1 common light chain"), as well as IgVκ1-39*01/IGJκ5. A variety of MeMo® transgenic animals referred to above comprises the IGVK1-39/JK1 common light chain.

A common light chain according to the invention also refers to light chains which may be identical or have some amino acid sequence differences while the binding specificity of the antibody or antibody fragment of the invention is not affected. Those of ordinary skill in the art will recognize that "common" also refers to functional equivalents of the light chain of which the amino acid sequence is not identical. Variants of said light chain exist wherein changes are present in comparison to the parental common light chain that do not materially influence the formation of functional binding regions. Such variants are thus also capable of binding different heavy chains and forming functional antigen binding domains. It is for instance possible within the scope of the definition of common light chains as used herein, to prepare or find variable light chains that are not identical but still functionally equivalent, e.g., by introducing and testing conservative amino acid changes, changes of amino acids in regions that do not or only partly contribute to binding specificity when paired with a cognate chain, and the like. Such variants are thus also capable of binding different cognate chains and forming functional antigen binding domains. The term 'common light chain' as used herein thus refers to light chains which may be identical or have some amino acid sequence differences while retaining the binding specificity of the resulting antibody after pairing with a heavy chain. A combination of a certain common light chain and such functionally equivalent variants is encompassed within the term "common light chain". Reference is made to WO 2004/009618, WO2019/190327 and WO2009/157771 for a detailed description of the use of common light chains. Preferably, a common light chain is used in the present invention which is a germline-like light chain, more preferably a germline light chain, preferably a rearranged germline human kappa light chain, most preferably either the rearranged germline human kappa light chain IgVκ1-39/Jκ or IGVκ3-20/Jr.

The antibody or antibody fragment can be produced, for example, from a hybridoma using a hybridoma method. Alternatively, the antibody or antibody fragment can be produced by secretion from a mammalian cell co-expressing the heavy and/or light chains, or fragments thereof. Preferably, the antibody or antibody fragment is produced by immunizing a non-human animal. These, and other, methods are known in the art and can suitably be used for producing the antibody or antibody fragment of the present invention.

Antibodies can be produced from various animal species. The MeMo® transgenic animals referred to above comprising the IGVK1-39/JK1 common light chain can suitably be used. Generally, transgenic mice are immunized with the human target DNA and/or protein followed by immunization boosts, thereby generating an immune response including the production of antigen-specific antibodies. Serum titers from immunized mice can be determined by ELISA and FACS analysis. Spleen and draining lymphoid material of the immunized mice may then be collected and single cell suspensions generated. RNA can be isolated and cDNA synthesized that encode the heavy chain and/or variable regions of such antibodies. VH and/or VL-family specific PCR can then be performed in order to generate phage display libraries. Human target protein binding Fabs can then be selected using for instance the Kingfisher selection robot. The nucleic acid encoding the heavy chain and/or light chain variable region of the Fabs that bind the target protein can be used for the production of antibodies in host cells.

There are instances where immunization of the transgenic organism generates antibodies, but where such antibodies are not cross-reactive for a human and transgenic animal, making the assaying and testing of such antibodies less efficient. Accordingly, it may be beneficial to obtain binding domains or antibodies, including chimeric or humanized binding domains or antibodies, that contain variable regions and/or complementary determining regions (CDR), and the nucleic acids that encode said variable regions and or CDRs, that are based on, derived or obtained from a nucleic acid, of species that are evolutionarily distant to humans. One potential source of such variable regions may be birds, for example, domesticated birds, such as chickens, ducks or ostriches. Antibody repertoires generated via immunization of birds, for example, chickens, ducks or ostriches may identify unique epitopes when compared to antibodies generated via the immunization of mice or other species evolutionarily close to humans (e.g., rodents and cynomolgus).

A primary DNA or protein immunization may be carried out followed by more booster immunizations. IgY antibodies can be isolated from yolk of the collected eggs or serum from the immunized birds. Spleen and/or bone marrow are removed from birds showing a significant humoral response against the target protein. RNA can subsequently be isolated and cDNA is synthesized. The generated cDNA samples are then used as a template to amplify and digest VH and/or VL genes using two primers. The PCR products are then cloned in a phagemid vector for the display of Fab fragments on phage essentially as described in de Haard et al. (J Biol Chem. (1999), Vol. 274(26), pp. 18218-18230). The nucleic acids encoding the VH and/or VL regions are ligated into a vector and the resulting ligated vector transformed into cells to yield libraries. Panning selections using KingFisher Flex can then be performed to select the phages that bind the target protein. Screening can be carried out by FACS on cells expressing the human or mouse target protein. The VH and/or VL genes of all clones that specifically bind the human and/or mouse target protein are sequenced. The nucleic acid encoding the heavy chain and/or light chain variable region of the binding domain that bind the target protein can be used for the production of antibodies in host cells.

Antibody fragments can be produced by methods known in the art.

scFv antibodies can be produced by isolating mRNA from the hybridoma or mammalian cell, which is then reverse transcribed into cDNA for PCR amplification. This results in the production of large libraries containing a varied range of VH and VL antibody genes (Marks and Hoogenboom, Journal of Molecular Biology (1991), Vol. 222, pp. 581-597). While constructing the scFv, the domains may be ordered as VH-linker-VL or as VL-linker-VH (Hu, O'Dwyer and Wall, Journal of Biotechnology (2005), Vol. 120, pp. 38-45). An example of a linker may be the classical (G4S)3 linker (Huston et al., Proc Natl Acad Sci USA (1988), Vol. 85, pp. 5879-5883). For minibodies, the DNA fragment encoding the hinge-CH3 domain can, for example, be based on the sequences of human IgG1 (Kim et al., PLOS One (2014), Vol. 9(12), e113442). scFv and hinge-CH3 regions may be assembled either by ligating cohesive ends generated by XhoI and SALI, or by using PCR to bring the XhoI restriction site of the scFv product together with the hinge, to the NH2 terminus of the CH3 (Hu et al., Cancer Research (1996), Vol. 56, pp. 3055-3061). After PCR, the V domains of an antibody can then be recombined through in vitro recombination in plasmids or phagemids (Lilley et al., Journal of Immunological Methods (1994), Vol. 171, pp. 211-226. Hogrefe et al., Gene (1993), Vol. 128, pp. 119-126). This phage display technology relies on the fusion of the antibody fragments to the phage minor coat protein pIII or its C-terminal domain (Smith, Science (1985), Vol. 228, pp. 1315-1317. Hoogenboom, Nature Biotechnology (2005), Vol. 23, pp. 1105-1116). Aside from displaying scFv fragments, phage display is now also widely used to display Fab fragments (Wieland et al., Veterinary Immunology and Immunopathology (2006), Vol. 110, pp. 129-140).

Fab fragments can be generated from monoclonal antibodies via enzymatic digestion using papain or pepsin. Papain digestion of antibodies produces three distinct fragments: two antigen-binding fragments called Fab fragments or regions, each with a single antigen-binding site, and one Fc region by cleaving below the CH1 domain (Porter, Biochem (1959), Vol. 73, pp. 119-126). Pepsin digestion of antibodies produces two fragments: a F(ab')2 fragment containing two antigen binding regions connected via the disulfide bridge of the hinge region and an Fc fragment (Valedkarimi et al., Human Antibodies (2018), Vol. 26, pp. 171-176). These Fab and F(ab')2 fragments may be purified through a combination of the following techniques: ion exchange, protein A or G affinity, antigen affinity or gel filtration chromatographies (Mage and Lamoyi. Monoclonal Antibody Production Techniques and Applications, Marcel Dekker Inc, New York, 1987, pp. 79-97). F(ab')n or (modified F(ab')n) may be produced in connection with the invention described herein and can be obtained using any suitable enzymatic cleavage and/or digestion techniques. In certain embodiments, the antibody fragment can be obtained by cleavage with the IdeS protease, an IgG-degrading enzyme of *Streptococcus pyogenes* that cleaves a human IgG1 at a specific site below the hinge leaving intact a F(ab')n antibody fragment, wherein n is the number of antibody domains present on the IgG, wherein the heavy chain on one side of the F(ab')n is paired to the heavy chain on the other side at their respective C-terminus, wherein the pairing comprises two or more disulfide bridges. Methods for generation of bispecific and multispecific antibodies wherein n=2 or more have been previously described. See PCT/NL2019/050199; PCT/NL2013/050294; PCT/NL2013/050293, which are incorporated by reference.

Alternatively, an antibody fragment lacking a Fc region can be obtained by use of a cysteine protease from *Porphyoromonas gingivalis*, that digests human IgG1 at a specific site above the hinge (KSCDK/THTCPPC), generating intact Fab and Fc fragments. An antibody fragment can be formed via this technique through the expression of a heavy chain comprising a variable domain and constant domain (e.g., CH1, CH2 and/or CH3), which is connected to an additional variable domain via a linker described herein, or paired to a light chain, which is connected to an additional variable domain via a linker described herein, and wherein a proteolytic enzyme, such as from *Porphyoromonas gingivalis* cleaves the constant domains of said heavy chain, leaving an intact truncated antibody binding fragment.

The generation of sdAbs has been achieved through phage display and by using repertoires of naïve or synthetic VH or VL dAbs based on the incorporation of solubilizing residues from camelid sdAbs into human VHs (Tanha et al., J. Biol. Chem (2001), Vol. 276, pp. 24774-24780. Davies and Riechmann, Biotechnology (1995), Vol. 13, pp. 475-479). Human sdAbs have also been attained without the need of engineering, through a selection method based on reversible unfolding and affinity criteria which resulted in a number of VHs from synthetic human VH phage display libraries (Jespers at al, Nat. Biotechnol (2004), Vol. 337, pp. 893-903). Another phage selection method may be used to obtain exclusively non-aggregating human VH domains from a naïve human VH display library (To et al., J Biol Chem (2005), Vol. 280, pp. 41395-41403). This same technique may be applied to obtained VLs (Kim et al., Landes Bioscience (2014), Vol. 6:1, pp. 219-235).

The antibody or antibody fragment of the present invention can be used for the treatment of cancer, by administering an effective amount of the antibody or antibody fragment to a subject in need thereof.

As used herein, the terms "subject" and "patient" are used interchangeably and refer to a mammal such as a human, mouse, rat, hamster, guinea pig, rabbit, cat, dog, monkey, cow, horse, pig and the like (e.g., a patient, such as a human patient, having cancer).

The terms "treat," "treating," and "treatment," as used herein, refer to any type of intervention or process performed on or administering an active agent or combination of active agents to a subject with the objective of curing or improving a disease or symptom thereof. This includes reversing, alleviating, ameliorating, inhibiting, or slowing down a symptom, complication, condition or biochemical indicia associated with a disease, as well as preventing the onset, progression, development, severity or recurrence of a symptom, complication, condition or biochemical indicia associated with a disease.

As used herein, "effective treatment" or "positive therapeutic response" refers to a treatment producing a beneficial effect, e.g., amelioration of at least one symptom of a disease or disorder, e.g., cancer. A beneficial effect can take the form of an improvement over baseline, including an improvement over a measurement or observation made prior to initiation of therapy according to the method. For example, a beneficial effect can take the form of slowing, stabilizing, stopping or reversing the progression of a cancer in a subject at any clinical stage, as evidenced by a decrease or elimination of a clinical or diagnostic symptom of the disease, or of a marker of cancer. Effective treatment may, for example, decrease in tumor size, decrease the presence of circulating tumor cells, reduce or prevent metastases of a tumor, slow or arrest tumor growth and/or prevent or delay tumor recurrence or relapse.

The term "therapeutic amount" or "effective amount" refers to an amount of an agent or combination of agents that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In some embodiments, a therapeutic amount is an amount sufficient to delay tumor development. In some embodiments, a therapeutic amount is an amount sufficient to prevent or delay tumor recurrence.

The therapeutic amount of the drug or composition may: (i) reduce the number of cancer cells; (ii) reduce tumor size; (iii) inhibit, retard, slow to some extent and may stop cancer cell infiltration into peripheral organs; (iv) inhibit tumor metastasis; (v) inhibit tumor growth; (vi) prevent or delay occurrence and/or recurrence of tumor; and/or (vii) relieve to some extent one or more of the symptoms associated with the cancer.

A therapeutic amount may vary according to factors such as the disease state, age, sex, and weight of the individual to be treated, and the ability of the agent or combination of agents to elicit a desired response in the individual.

A therapeutic amount can be administered in one or more administrations.

A therapeutic amount also includes an amount that balances any toxic or detrimental effects of the agent or combination of agents and the therapeutically beneficial effects.

In more specific terms, the present invention provides an antibody or antibody fragment thereof that specifically binds to the extracellular domain of human TGF-βRII, wherein the antibody or antibody fragment binds to an epitope of the extracellular domain of human TGF-βRII of which phenylalanine (F) at position 25 is a critical residue for binding.

In the research leading up to the present invention, antibodies have been identified that bind to a particular epitope of the extracellular domain of human TGF-βRII. This epitope comprises at least the amino acid residue at position 25 of the extracellular domain of isoform A of human TGF-βRII. The amino acid sequence of the extracellular domain of isoform A of human TGF-βRII is as set forth in SEQ ID NO: 102. The amino acid at position 25 of this sequence is phenylalanine (F) (bold and underlined). The database accession number for the human TGF-βRII protein and the gene encoding isoform A is GenBank NM_001024847.2 (protein seq reference is NP_001020018.1; SEQ ID NO:102). A splice variant encoding a longer isoform due to an insertion in the extracellular domain is isoform B. The gene encoding isoform B is GenBank NM_003242.6 (protein seq reference is NP_003233.4; SEQ ID NO: 103 with the insertion underlined). The amino acid at position 25 of the extracellular domain of isoform A corresponds to the amino acid at position 50 of the extracellular domain of isoform B. The amino acid sequence of the extracellular domain of isoform B of human TGF-βRII is as set forth in SEQ ID NO: 104. The amino acid, phenylalanine (F), at position 50 of this sequence is in bold and underlined. These accession numbers are primarily given to provide a further method of identifying the TGF-βRII protein as a target, the actual sequence of the TGF-βRII protein bound by an antibody may vary, for instance because of a mutation in the encoding gene such as those occurring in some cancers or the like.

Anywhere this description refers to the amino acid at position 25 of human TGF-βRII, it refers to the amino acid at position 25 of the extracellular domain of isoform A of human TGF-βRII as well as to the corresponding position of another isoform of human TGF-βRII, in particular position 50 of isoform B. The same applies to other amino acid positions identified herein.

The amino acid residue at position 25 of the extracellular domain of human TGF-βRII was found to be a critical residue for binding of the antibodies of the invention, as determined by alanine scanning. In alanine scanning, the amino acids at each position of an antigen, in the present case TGF-βRII, are substituted one by one with alanine. If this diminishes or significantly reduces the binding of an antibody that binds the unmodified antigen, the amino acid that is substituted thus contributes to binding and is considered to be a critical residue. The antibody or antibody fragment thus specifically binds an epitope comprising such residue. In the present context, an amino acid residue is considered as a critical residue if its binding activity or reactivity is reduced by more than 50%, as compared to the unmodified amino acid sequence. "Significantly reduced" thus means a binding activity or reactivity which is reduced by at least more than 50%, as compared to the unmodified amino acid sequence of the extracellular domain of human TGFβRII.

Accordingly, the antibody or antibody fragment of the present invention has a binding activity or reactivity of less than 50%, preferably less than 40%, 30%, 20%, 10%, 5%, or 2%, when the phenylalanine (F) at position 25 of the amino acid sequence of the extracellular domain of human TGFβRII, the wildtype sequence of which is as set forth in SEQ ID No.102, is replaced with alanine (A), as compared to the wildtype amino acid sequence of the extracellular domain of human TGFβRII.

Thus, an antibody or antibody fragment of the present invention specifically binds to an epitope of human TGF-βRII comprising phenylalanine (F) at position 25 of the amino acid sequence of the extracellular domain of human TGF-βRII. Preferably, the binding of an antibody or antibody fragment to this epitope is determined by alanine scanning, wherein an antibody or antibody fragment that binds to this epitope has a binding activity or reactivity of less than 50%, preferably less than 40%, 30%, 20%, 10%, 5%, or 2%, when alanine (A) is present at position 25 of the amino acid sequence of the extracellular domain of human TGF-βRII, as compared to when phenylalanine (F) is present at said position.

Another way of defining an antibody or antibody fragment of the present invention is that it binds to an epitope of the extracellular domain of human TGFβRII of which a substitution of a phenylalanine (F) residue that in isoform A of human TGFβRII, the wildtype sequence of which is as set forth in SEQ ID No.102, is at position 25, for an alanine (A), reduces the binding of the antibody or antibody fragment by at least 50%, preferably by at least 60%, 70%, 80%, 90%, 95%, or 98%.

An antibody or antibody fragment of the present invention may also be defined as an antibody or antibody fragment that binds to an epitope in the extracellular domain of human TGF-βRII, wherein the epitope comprises a phenylalanine (F) residue that in isoform A of human TGF-βRII, the wildtype sequence of which is as set forth in SEQ ID No.102, is at position 25. In addition to the critical amino acid residue at position 25, aspartate (D) at position 119 of the epitope of the extracellular domain of isoform A of human TGF-βRII was identified as a further critical residue for binding. The amino acid at position 119 of isoform A corresponds to the amino acid at position 144 of the extracellular domain of isoform B of human TGF-βRII (SEQ ID NO: 104). The antibody or antibody fragment of the invention preferably has a binding reactivity of less than 10%, more preferably less than 5%, 4%, 3%, or 2%, when the aspartate (D) at position 119 of the wildtype amino acid sequence of the extracellular domain of human TGF-βRII is replaced with alanine (A), as compared to the wildtype amino acid sequence of the extracellular domain of human TGF-βRII.

In a particular embodiment, the antibody or antibody fragment preferably has:

a binding reactivity of less than 5%, preferably less than 3%, when the phenylalanine (F) at position 25 of the wildtype amino acid sequence of the extracellular domain of human TGF-βRII is replaced with alanine (A);

a binding reactivity of less than 5%, preferably less than 3%, when the aspartate (D) at position 119 of the wildtype amino acid sequence of the extracellular domain of human TGF-βRII is replaced with alanine (A), as compared to the wildtype amino acid sequence of the extracellular domain of human TGFβRII Thus, the present invention encompasses an antibody or antibody fragment that specifically binds to an epitope of human TGF-βRII comprising phenylalanine (F) at position 25 and aspartate (D) at position 119 of the amino acid sequence of the extracellular domain of human TGF-βRII. Preferably, the binding of an antibody or antibody fragment to this epitope is determined by alanine scanning, wherein an antibody or antibody fragment that binds to this epitope has a binding activity or reactivity of less than 50%, preferably less than 5%, or 3%, when alanine is present at position 25 of the amino acid sequence of the extracellular domain of human TGF-βRII, and a binding activity or reactivity of less than 10%, preferably less than 5%, or 3%, when alanine (A) is present at position 119 of the amino acid sequence of the extracellular domain of human TGF-βRII, as compared to when phenylalanine (F) and aspartate (D) are present at said respective positions, wherein each change is tested in isolation and not as a combination of two changes as compared to the wildtype extracellular domain.

Another way of defining an antibody or antibody fragment of the present invention is that it binds to an epitope of the extracellular domain of human TGFβRII of which a substitution of a phenylalanine (F) residue that in isoform A of human TGFβRII, the wildtype sequence of which is as set forth in SEQ ID No.102, is at position 25, for an alanine (A), reduces the binding of the antibody or antibody fragment by at least 50%, preferably by at least 95%, or 97%; and a substitution of an aspartate (D) residue that in isoform A of human TGFβRII, the wildtype sequence of which is as set forth in SEQ ID No.102, is at position 119, for an alanine (A), reduces the binding of the antibody or antibody fragment by at least 90%, preferably by at least 95%, or 97%.

An antibody or antibody fragment of the present invention may also be defined as an antibody or antibody fragment that binds to an epitope in the extracellular domain of human TGF-βRII, wherein the epitope comprises a phenylalanine (F) residue and an aspartate (D) residue that in isoform A of human TGF-βRII, the wildtype sequence of which is as set forth in SEQ ID No.102, are at positions 25 and 119 respectively.

In another embodiment, the antibody or antibody fragment binds to an epitope of the extracellular domain of human TGF-βRII of which threonine (T) at position 52 of the epitope of the extracellular domain of isoform A of human TGF-βRII is a further critical residue for binding. The amino acid at position 52 of isoform A corresponds to the amino acid at position 77 of isoform B of human TGF-βRII. In this embodiment, the antibody or antibody fragment preferably has:

a binding reactivity of less than 5%, preferably less than 2%, when the phenylalanine (F) at position 25 of wildtype amino acid sequence of the extracellular domain of human TGF-βRII is replaced with alanine (A);

a binding reactivity of less than 60%, preferably less than 40% or 30%, more preferably less than 20%, when the threonine (T) at position 52 of the wildtype amino acid sequence of the extracellular domain of human TGF-βRII is replaced with alanine (A); and a binding reactivity of less than 3% when the aspartate (D) at position 119 of the wildtype amino acid sequence of the extracellular domain of human TGF-βRII is replaced with alanine (A), as compared to the wildtype amino acid sequence of the extracellular domain of human TGF-βRII.

Thus, the present invention encompasses an antibody or antibody fragment that specifically binds to an epitope of human TGF-βRII comprising phenylalanine (F) at position 25, threonine (T) at position 52, and aspartate (D) at position 119, of the amino acid sequence of the extracellular domain of human TGF-βRII. Preferably, the binding of an antibody or antibody fragment to this epitope is determined by alanine scanning, wherein an antibody or antibody fragment that binds to this epitope has a binding activity or reactivity of less than 50%, preferably less than 5%, or 2%, when alanine (A) is present at position 25 of the amino acid sequence of the extracellular domain of human TGF-βRII, a binding activity or reactivity of less than 60%, preferably less than 40%, 30%, or 20%, when alanine (A) is present at position 52 of the amino acid sequence of the extracellular domain of human TGF-βRII, and a binding activity or reactivity of less than 10%, preferably less than 3%, when alanine (A) is present at position 119 of the amino acid sequence of the extracellular domain of human TGF-βRII, as compared to when phenylalanine (F), threonine (T) and aspartate (D) are present at said respective positions, wherein each change is tested in isolation and not as a combination of two changes as compared to the wildtype extracellular domain.

Another way of defining an antibody or antibody fragment of the present invention is that it binds to an epitope of the extracellular domain of human TGFβRII of which a substitution of a phenylalanine (F) residue that in isoform A of human TGFβRII, the wildtype sequence of which is as set forth in SEQ ID No.102, is at position 25, for an alanine (A), reduces the binding of the antibody or antibody fragment by at least 50%, preferably by at least 95%, or 98%;

a substitution of a threonine (T) residue that in isoform A of human TGFβRII, the wildtype sequence of which is as set forth in SEQ ID No.102, is at position 52, for an alanine (A), reduces the binding of the antibody or antibody fragment by at least 60%, preferably by at least 70%, or 80%; and a substitution of an aspartate (D) residue that in isoform A of human TGFβRII, the wildtype sequence of which is as set forth in SEQ ID No.102, is at position 119, for an alanine (A), reduces the binding of the antibody or antibody fragment by at least 90%, preferably by at least 97%.

An antibody or antibody fragment of the present invention may also be defined as an antibody or antibody fragment that binds to an epitope in the extracellular domain of human TGF-βRII, wherein the epitope comprises a phenylalanine (F) residue, a threonine (T) residue, and an aspartate (D) residue that in isoform A of human TGF-βRII, the wildtype sequence of which is as set forth in SEQ ID No.102, are at positions 25, 52 and 119 respectively.

In another embodiment, the antibody or antibody fragment binds to an epitope of the extracellular domain of human TGF-βRII of which isoleucine (I) at position 54 and glutamate (E) at position 120 of the epitope of the extracellular domain of isoform A of human TGF-βRII are further critical residues for binding. The amino acids at positions 54 and 120 of isoform A correspond to the amino acids at positions 79 and 145, respectively, of isoform B of human TGF-βRII. In this embodiment, the antibody or antibody fragment preferably has:

a binding reactivity of less than 10% when the phenylalanine (F) at position 25 of the wildtype amino acid sequence of the extracellular domain of human TGF-βRII is replaced with alanine (A);

a binding reactivity of less than 20% when the isoleucine (I) at position 54 of the wildtype amino acid sequence of the extracellular domain of human TGF-βRII is replaced with alanine (A);

a binding reactivity of less than 3%, preferably less than 2%, more preferably less than 1%, when the aspartate (D) at position 119 of the wildtype amino acid sequence of the extracellular domain of human TGF-βRII is replaced with alanine (A); and a binding reactivity of less than 80%, preferably less than 70%, 60%, 50%, 40%, more preferably less than 30%, most preferably less than 10% or 5%, when the glutamate (E) at position 120 of the wildtype amino acid sequence of the extracellular domain of human TGF-βRII is replaced with alanine (A), as compared to the wildtype amino acid sequence of the extracellular domain of human TGF-βRII.

Thus, the present invention encompasses an antibody or antibody fragment that specifically binds to an epitope of human TGF-βRII comprising phenylalanine (F) at position 25, isoleucine (I) at position 54, aspartate (D) at position 119, and glutamate (E) at position 120, of the amino acid sequence of the extracellular domain of human TGF-βRII. Preferably, the binding of an antibody or antibody fragment to this epitope is determined by alanine scanning, wherein an antibody or antibody fragment that binds to this epitope has a binding activity or reactivity of less than 50%, preferably less than 10%, when alanine (A) is present at position 25 of the amino acid sequence of the extracellular domain of human TGF-βRII, a binding activity or reactivity of less than 20% when alanine (A) is present at position 54 of the amino acid sequence of the extracellular domain of human TGF-βRII, a binding activity or reactivity of less than 10%, preferably less than 3%, 2%, or 1%, when alanine (A) is present at position 119 of the amino acid sequence of the extracellular domain of human TGF-βRII, and a binding activity or reactivity of less than 80% preferably less than 70%, 60%, 50%, 40%, 30%, 10%, or 5%, when alanine (A) is present at position 120 of the amino acid sequence of the extracellular domain of human TGF-βRII, as compared to when phenylalanine (F), threonine (T), aspartate (D), and glutamate (E) are present at said respective positions, wherein each change is tested in isolation and not as a combination of two changes as compared to the wildtype extracellular domain.

Another way of defining an antibody or antibody fragment of the present invention is that it binds to an epitope of the extracellular domain of human TGFβRII of which a substitution of a phenylalanine (F) residue that in isoform A of human TGFβRII, the wildtype sequence of which is as set forth in SEQ ID No.102, is at position 25, for an alanine (A), reduces the binding of the antibody or antibody fragment by at least 50%, preferably by at least 90%;

a substitution of an isoleucine (I) residue that in isoform A of human TGFβRII, the wildtype sequence of which is as set forth in SEQ ID No.102, is at position 54, for an alanine (A), reduces the binding of the antibody or antibody fragment by at least 80%;

a substitution of an aspartate (D) residue that in isoform A of human TGFβRII, the wildtype sequence of which is as set forth in SEQ ID No.102, is at position 119, for an alanine (A), reduces the binding of the antibody or antibody fragment by at least 90%, preferably by at least 97%, 98%, or 99%; and a substitution of a glutamate (E) residue that in isoform A of human TGFβRII, the wildtype sequence of which is as set forth in SEQ ID No.102, is at position 120, for an alanine (A), reduces the binding of the antibody or antibody fragment by at least 30%, preferably by at least 40%, 50%, 60%, 70%, 90%, or 95%.

An antibody or antibody fragment of the present invention may also be defined as an antibody or antibody fragment that binds to an epitope in the extracellular domain of human TGF-βRII, wherein the epitope comprises a phenylalanine (F) residue, an isoleucine (I) residue, an aspartate (D) residue, and a glutamate (E) residue that in isoform A of human TGF-βRII, the wildtype sequence of which is as set forth in SEQ ID No.102, are at positions 25, 54, 119, and 120 respectively.

The present inventors identified a number of antibodies that comprise a heavy chain variable region that specifically binds to an epitope of the extracellular TGF-βRII of which phenylalanine (F) at position 25 is critical for binding. One example of such antibody comprises a heavy chain variable region (VH) having:

(a) a VH-CDR1 comprising the amino acid sequence set forth in SEQ ID No. 1, (b) a VH-CDR2 comprising the amino acid sequence set forth in SEQ ID No. 2, and (c) a VH-CDR3 comprising the amino acid sequence set forth in SEQ ID No. 3, wherein one to five amino acid residue(s) may be varied with conservative amino acid(s) thereof in any one or more of the CDR(s) selected from VH-CDR1, VH-CDR2 and VH-CDR3. This antibody is encompassed by the present invention.

Another example of such antibody comprises a heavy chain variable region (VH) having:

(a) a VH-CDR1 comprising the amino acid sequence set forth in SEQ ID No. 4, (b) a VH-CDR2 comprising the amino acid sequence set forth in SEQ ID No. 5, and (c) a VH-CDR3 comprising the amino acid sequence set forth in SEQ ID No. 6, wherein one to five amino acid residue(s) may be varied with conservative amino acid(s) thereof in any one or more of the CDR(s) selected from VH-CDR1, VH-CDR2 and VH-CDR3. This antibody is also encompassed by the present invention.

Another example of such antibody comprises a heavy chain variable region (VH) having:

(a) a VH-CDR1 comprising the amino acid sequence set forth in SEQ ID No. 7, (b) a VH-CDR2 comprising the amino acid sequence set forth in SEQ ID No. 8, and (c) a VH-CDR3 comprising the amino acid sequence set forth in SEQ ID No. 9, wherein one to five amino acid residue(s) may be varied with conservative amino acid(s) thereof in any one or more of the CDR(s) selected from VH-CDR1, VH-CDR2 and VH-CDR3. This antibody is also encompassed by the present invention.

The heavy chain variable region of the antibody or antibody fragment of the invention may thus comprise a CDR1 selected from the group consisting of the sequences as set forth in SEQ ID NOs: 1, 4, and 7; a CDR2 selected from the group consisting of the sequences as set forth in SEQ ID NOs: 2, 5, and 8; and/or a CDR3 selected from the group consisting of the sequences as set forth in SEQ ID NOs: 3, 6, and 9; wherein one to five amino acid residue(s) may be varied with conservative amino acid(s) thereof in any one or more of the CDR(s) selected from CDR1, CDR2 and CDR3.

The framework regions of the heavy chain variable region may be selected from any suitable framework regions. Examples of suitable framework regions are the framework regions encoded by the human V genes IGHV3-15 and IGHV3-23. These germline V genes may comprise one or more somatic mutations.

In one embodiment of the present invention, the antibody or an antibody fragment thereof comprises a VH having amino acid sequence: EVQLVESGGGLVQPGGSLRLS-CAASGFTFDIYAMTWVRQAPGKGLEWVSVISG SGGTTYYADSVKGRFTISRDNSKNTLYLQMNSLRAE-DTAVYYCARRGQYRDIV GATDYWGQGTLVTVSS (SEQ ID NO: 10), or a VH amino acid sequence having at least 80%, preferably at least 90%, more preferably at least 95%, identity thereto.

In another embodiment, the antibody or an antibody fragment thereof comprises a VH having amino acid sequence: QVQLVESGGGLVEPGGSLRLS-CAASGFTFSNAWMSWVRQAPGKGLEWVGRIK TTIS-GGATDFAAPVKGRFTISRDDSKNTLYLQMNSLKTED-TAVYYCTLDLRDY WGQGTLVTVSS (SEQ ID NO: 11), or a VH amino acid sequence having at least 80%, preferably at least 90%, more preferably at least 95%, identity thereto.

In another embodiment, the antibody or an antibody fragment thereof comprises a VH having amino acid sequence: QVQLVESGGGLVQPGGSLRLSCAVSGFTFR-RYAMSWVRQAPGKGLEWVSAIS ASGDRTH-NTDSVKGRFSISRDNSKNTLYLQMNSLRAED-TAVYFCAKGIAASGK NYFDPWGQGTLVTVSS (SEQ ID NO: 12), or a VH amino acid sequence having at least 80%, preferably at least 90%, more preferably at least 95%, identity thereto.

The heavy chain variable region can have 0-10, preferably 0-5 amino acid variations with respect to the indicated amino acid sequence. In a preferred embodiment the heavy chain variable region comprises 0-9, 0-8, 0-7, 0-6, 0-5, 0-4, preferably 0-3, preferably 0-2, preferably 0-1 and more preferably 0 amino acid variations, insertions, deletions, substitutions, additions with respect to the indicated amino acid sequence, or a combination thereof at positions other than the CDRs. A combination of an insertion, addition, deletion or substitution is a combination if aligned sequences do not differ at more than 10, preferably no more than 5 positions. A gap in one of the aligned sequences counts for as many amino acids as skipped in the other sequence. An amino acid substitution, if any, is preferably a conservative amino acid substitution. The substitutions in the heavy chain variable region may be in addition to the substitutions in the one or more CDRs as described above. Conservative amino acids are known in the art based on similarities of the respective functional groups based on characteristics such as charge, hydrophobicity, hydrophilicity, acidity, basic, and size.

An amino acid variation, insertion, deletion, substitution, addition or combination thereof is preferably not made in the binding interface of the heavy and light chain.

If an amino acid is changed in the interface of the H/L chain interaction, it is preferred that the corresponding amino acids in the other chain are changed to accommodate the change. An insertion or addition of an amino acid preferably does not entail the insertion or addition of a proline.

The invention encompasses antibodies or antibody fragments comprising a variant of the antibody or antibody fragment as described herein. In particular an antibody or antibody fragment comprising a VH having any one of SEQ ID NO: 22-91 and 93, i.e. any one of the VH sequences as shown in FIG. 4. Also encompassed are antibodies or antibody fragments comprising at least HCDR3, or all CDRs, of any one of SEQ ID NO: 22-91 and 93. Preferred antibodies or antibody fragments comprise a heavy chain variable region having, or which is derived from, an amino acid sequence set forth in SEQ ID NO: 40; 43; 46; 47; 48 or 54, which are variants of antibodies comprising a heavy chain variable region comprising an amino acid sequence set forth in SEQ ID NO: 11. Other preferred antibodies or antibody fragments comprise a heavy chain variable region having, or which is derived from, an amino acid sequence set forth in SEQ ID NO: 67; 70; 75; 76; 77; 78; 83; 84; or 88, which are variants of antibodies comprising a heavy chain variable region comprising an amino acid sequence set forth in SEQ ID NO: 12. Other preferred antibodies or antibody fragments comprise a heavy chain variable region having, or which is derived from, an amino acid sequence set forth in SEQ ID NO:24 or 26, which are variants of antibodies comprising a heavy chain variable region comprising an amino acid sequence set forth in SEQ ID NO: 10. The most preferred variants are those comprising a heavy chain variable region having an amino acid sequence set forth in SEQ ID NO: 40; 43; 46; 47; 48; 54; 67; 70; 75; 76; 77; 78; 83; 84; or 88.

The heavy chain variable region of such variant can have 0-10, preferably 0-5 amino acid variations with respect to the indicated amino acid sequence. In a preferred embodiment the heavy chain variable region comprises 0-9, 0-8, 0-7, 0-6, 0-5, 0-4, preferably 0-3, preferably 0-2, preferably 0-1 and more preferably 0 amino acid variations, insertions, deletions, substitutions, additions with respect to the indicated amino acid sequence, or a combination thereof at positions other than the CDRs.

The antibody or antibody fragment, or the binding domain, of the present invention may comprise any suitable light chain, such as for instance a cognate light chain or a common light chain as defined herein.

In one embodiment, the light chain variable region comprises the amino acid sequence of an IgVκ1-39*01 gene segment as depicted in FIG. 1B with 0-10, preferably 0-5 amino acid variations, insertions, deletions, substitutions, additions or a combination thereof. IgVκ1-39 is short for Immunoglobulin Variable Kappa 1-39 Gene. The gene is also known as Immunoglobulin Kappa Variable 1-39; IGKV139; IGKV1-39. External Ids for the gene are HGNC: 5740; Entrez Gene: 28930; Ensembl: ENSG00000242371. A preferred amino acid sequence for IgVκ1-39 is given in FIG. 1A. This lists the sequence of the V-region. The V-region can be combined with one of five J-regions. FIGS. 1B and 1C describe two preferred sequences for IgVκ1-39 in combination with a J-region. The joined sequences are indicated as IGKV1-39/jk1 and IGKV1-39/jk5; alternative names are IgVκ1-39*01/IGKV1*01 or IgVκ1-39*01/IGJκ5*01 (nomenclature according to the IMGT database worldwide web at imgt.org).

It is preferred that the IgVκ1-39*01 comprising light chain variable region is a germline sequence. It is further preferred that the IGJκ1*01 or IGJκ5*01 comprising light chain variable region is a germline sequence. It is further preferred that the IGKV1-39/jk1 or IGKV1-39/jk5 light chain variable regions are germline sequences.

Mature B-cells that produce an antibody with a light chain often produce a light chain that has undergone one or more mutations with respect to the germline sequence, meaning the normal sequence in non-lymphoid cells of the organism. The process that is responsible for these mutations is referred to as somatic hypermutation. The resulting light chain is referred to as an affinity matured light chain. Such light chains, when derived from a germline IgVκ1-39*01 sequence are IgVκ1-39*01 derived light chains. In this specification, the phrase "IgVκ1-39*01" will include IgVκ1-39*01-derived light chains. The mutations that are introduced into nucleic acid encoding the light chain by somatic hypermutation can also be introduced artificially in the lab. In the lab also other variations to a light chain can be introduced without affecting the properties of the light chain in kind, not necessarily in amount. A light chain is at least an IgVκ1-39*01 light chain if it comprises a sequence as depicted in FIG. 1A, FIG. 1B or FIG. 1C with 0-10, preferably 0-5 amino acid variations, insertions, deletions, substitutions, additions or a combination thereof. Preferably, the IgVκ1-39*01 light chain is a light chain comprising a sequence as depicted in FIG. 1A, FIG. 1B or FIG. 1C with 0-9, 0-8, 0-7, 0-6, 0-5, 0-4 amino acid variations, insertions, deletions, substitutions, additions or a combination thereof, more preferably a sequence as depicted in FIG. 1A, FIG. 1B or FIG. 1C with 0-5, preferably 0-4, 0-3, 0-2, 0-1 amino acid variations, insertions, deletions, substitutions, additions or a combination thereof, even more preferably a sequence as depicted in FIG. 1A, FIG. 1B or FIG. 1C with 0-3 amino acid variations, insertions, deletions, substitutions, additions or a combination thereof, even more preferably a sequence as depicted in FIG. 1A FIG. 1B or FIG. 1C with 0-2 amino acid variations, insertions, deletions, substitutions, additions or a combination thereof, even more preferably a sequence as depicted in FIG. 1A, FIG. 1B or FIG. 1C with 0-1 amino acid variations, insertions, deletions, substitutions, additions or a combination thereof, and most preferably 0 amino acid variations, insertions, deletions, substitutions, additions or a combination thereof.

In one embodiment, the antibody or an antibody fragment thereof, or the binding domain, comprises a light chain variable region (VL) having:

(a) a VL-CDR1 comprising the amino acid sequence set forth in SEQ ID No. 19, (b) a VL-CDR2 comprising the amino acid sequence set forth in SEQ ID No. 20, and (c) a VL-CDR3 comprising the amino acid sequence set forth in SEQ ID No. 21, wherein one to five amino acid residue(s) may be substituted with conservative amino acid(s) thereof in any one or more of the CDR(s) selected from VL-CDR1, VL-CDR2 and VL-CDR3.

The light chain variable region of the antibody or antibody fragment, or binding domain, of the invention preferably comprises a CDR1, CDR2, and CDR3 region comprising the amino acid sequence CDR1-QSISSY (SEQ ID NO:

13), CDR2-AAS (SEQ ID NO: 14), CDR3-QQSYSTPPT (SEQ ID NO: 15), i.e. the CDRs of IGKV1-39 (according to IMGT), allowing for 0-5 amino acid substitutions with respect to the indicated amino acid sequence. According to Kabat numbering, the amino acid sequences are: CDR1-RASQSISSYLN (SEQ ID NO: 19), CDR2-AASSLQS (SEQ ID NO: 20), CDR3-QQSYSTPPT (SEQ ID NO: 21). Any amino acid variations, insertions, deletions, substitutions, additions or combination thereof are preferably not in the CDR3 region of the light chain variable region, preferably not in the CDR1 or CDR2 region of the light chain variable region. An amino acid substitution is preferably a conservative amino acid substitution.

In particular, the light chain variable region of the antibody or antibody fragment, or binding domain, of the invention preferably comprises the amino acid sequence DIQMTQSPSSLSASVGDRVTITCRASQSIS-SYLNWYQQKPGKAPKLLIYAASSLQ SGVPSRFSGSGSGTDFTLTISSLQPEDFATYYCQQSYS-TPPTFGQGTKVEIK (SEQ ID NO: 16), or a VL amino acid sequence having at least 80% identity thereto. This thus, allows for 0-5 amino acid variations, insertions, deletions, substitutions, additions or a combination thereof. An amino acid substitution is preferably a conservative amino acid substitution.

The antibody of the present invention may be of any isotype: IgA, IgM, IgG, IgD or IgE. Preferably, the antibody is an IgG, in particular an IgG1 or IgG4. Most preferably, the antibody is an IgG1.

The constant region of an antibody of the present invention is preferably a human constant region, but may be of any animal. It can be a mouse or rat constant region. A mouse constant region or rat constant region may advantageously be used, depending on the host organism immunized or screening methodology employed to select the recombined antibodies generated in response to an antigen.

The antibody or antibody fragment thereof may comprise a heavy chain constant region comprising the amino acid sequence set forth in SEQ ID No. 17. The antibody or antibody fragment thereof may comprise a light chain constant region comprising the amino acid sequence set forth in SEQ ID No. 18. The constant region may contain one or more, preferably not more than 10, preferably not more than 5 amino acid differences with the constant region of a conventional human antibody.

Some antibodies are modified in the CH2/lower hinge region, for instance to reduce Fc-receptor interaction or to reduce ADCC, C1q binding or other effector activity. The antibody of the invention may be an IgG antibody with a variant CH2 and/or lower hinge domain such that interaction of the antibody to an Fc-gamma receptor is reduced. Such a mutant CH2 and/or lower hinge domain preferably comprises an amino variation at position 235 and/or 236 (EU numbering), preferably comprising residues at the following positions 235G and/or 236R.

The isolated monoclonal antibody may comprise two heavy chain constant regions of an IgG1 antibody, wherein lysine at position 447 according to the EU numbering system is deleted.

A preferred antibody or antibody fragment of the present invention comprises heavy chain variable region CDR and light chain variable region CDR combinations as listed in Table 1.

TABLE 1

| | | Possible combinations of heavy chain variable region CDRs and light chain variable region CDRs. | | | | |
|---|---|---|---|---|---|---|
| Antibody | HCDR1 | HCDR2 | HCDR3 | LCDR1 | LCDR2 | LCDR3 |
| 1 | SEQ ID NO: 1 | SEQ ID NO: 2 | SEQ ID NO: 3 | SEQ ID NO: 19 | SEQ ID NO: 20 | SEQ ID NO: 21 |
| 2 | SEQ ID NO: 4 | SEQ ID NO: 5 | SEQ ID NO: 6 | SEQ ID NO: 19 | SEQ ID NO: 20 | SEQ ID NO: 21 |
| 3 | SEQ ID NO: 7 | SEQ ID NO: 8 | SEQ ID NO: 9 | SEQ ID NO: 19 | SEQ ID NO: 20 | SEQ ID NO: 21 |
| 4 | SEQ ID NO: 105 | SEQ ID NO: 106 | SEQ ID NO: 107 | SEQ ID NO: 19 | SEQ ID NO: 20 | SEQ ID NO: 21 |
| 5 | SEQ ID NO: 108 | SEQ ID NO: 109 | SEQ ID NO: 110 | SEQ ID NO: 19 | SEQ ID NO: 20 | SEQ ID NO: 21 |
| 6 | SEQ ID NO: 111 | SEQ ID NO: 112 | SEQ ID NO: 113 | SEQ ID NO: 19 | SEQ ID NO: 20 | SEQ ID NO: 21 |
| 7 | SEQ ID NO: 114 | SEQ ID NO: 115 | SEQ ID NO: 116 | SEQ ID NO: 19 | SEQ ID NO: 20 | SEQ ID NO: 21 |
| 8 | SEQ ID NO: 117 | SEQ ID NO: 118 | SEQ ID NO: 119 | SEQ ID NO: 19 | SEQ ID NO: 20 | SEQ ID NO: 21 |
| 9 | SEQ ID NO: 120 | SEQ ID NO: 121 | SEQ ID NO: 122 | SEQ ID NO: 19 | SEQ ID NO: 20 | SEQ ID NO: 21 |
| 10 | SEQ ID NO: 123 | SEQ ID NO: 124 | SEQ ID NO: 125 | SEQ ID NO: 19 | SEQ ID NO: 20 | SEQ ID NO: 21 |
| 11 | SEQ ID NO: 126 | SEQ ID NO: 127 | SEQ ID NO: 128 | SEQ ID NO: 19 | SEQ ID NO: 20 | SEQ ID NO: 21 |
| 12 | SEQ ID NO: 129 | SEQ ID NO: 130 | SEQ ID NO: 131 | SEQ ID NO: 19 | SEQ ID NO: 20 | SEQ ID NO: 21 |
| 13 | SEQ ID NO: 132 | SEQ ID NO: 133 | SEQ ID NO: 134 | SEQ ID NO: 19 | SEQ ID NO: 20 | SEQ ID NO: 21 |

A preferred antibody or antibody fragment of the invention comprises a heavy chain having a VH comprising an amino acid sequence selected from the group consisting of SEQ ID NO: 10, 11, 12, 22-91 and 93, in particular a preferred VH as described herein, and a light chain having a VL comprising the amino acid sequence set forth in SEQ ID NO: 16. This antibody or antibody fragment can comprise any constant domain as described herein.

In one embodiment, the antibody or antibody fragment thereof as described herein comprises a heavy chain having a VH comprising the amino acid sequence set forth in SEQ ID No. 10, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 11, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 12, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 43, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 75, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 70, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 84, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 88, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 40, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 83, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 78, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 47, and a light chain having a VL comprising the amino acid sequence set forth in SEQ ID No. 16.

In another embodiment, the antibody or antibody fragment thereof as described herein comprises a heavy chain having a VH comprising the amino acid sequence set forth in SEQ ID No. 76, and a light chain having a VL comprising the amino acid sequence set forth in SEQ ID No. 16.

In one embodiment, the antibody or antibody fragment thereof as described herein comprises two heavy chain variable regions of SEQ ID NO: 10 and two light chain variable regions of SEQ ID NO: 16.

In another embodiment, the antibody or antibody fragment thereof as described herein comprises two heavy chain variable regions of SEQ ID NO: 11 and two light chain variable regions of SEQ ID NO: 16, In another embodiment, the antibody or antibody fragment thereof as described herein comprises two heavy chain variable regions of SEQ ID NO: 12 and two light chain variable regions of SEQ ID NO: 16.

In one embodiment, the antibody or antibody fragment thereof as described herein comprises two heavy chain variable regions of SEQ ID NO: 43 and two light chain variable regions of SEQ ID NO: 16.

In one embodiment, the antibody or antibody fragment thereof as described herein comprises two heavy chain variable regions of SEQ ID NO: 75 and two light chain variable regions of SEQ ID NO: 16.

In one embodiment, the antibody or antibody fragment thereof as described herein comprises two heavy chain variable regions of SEQ ID NO: 70 and two light chain variable regions of SEQ ID NO: 16.

In one embodiment, the antibody or antibody fragment thereof as described herein comprises two heavy chain variable regions of SEQ ID NO: 84 and two light chain variable regions of SEQ ID NO: 16.

In one embodiment, the antibody or antibody fragment thereof as described herein comprises two heavy chain variable regions of SEQ ID NO: 88 and two light chain variable regions of SEQ ID NO: 16.

In one embodiment, the antibody or antibody fragment thereof as described herein comprises two heavy chain variable regions of SEQ ID NO: 40 and two light chain variable regions of SEQ ID NO: 16.

In one embodiment, the antibody or antibody fragment thereof as described herein comprises two heavy chain variable regions of SEQ ID NO: 83 and two light chain variable regions of SEQ ID NO: 16.

In one embodiment, the antibody or antibody fragment thereof as described herein comprises two heavy chain variable regions of SEQ ID NO: 78 and two light chain variable regions of SEQ ID NO: 16.

In one embodiment, the antibody or antibody fragment thereof as described herein comprises two heavy chain variable regions of SEQ ID NO: 47 and two light chain variable regions of SEQ ID NO: 16.

In one embodiment, the antibody or antibody fragment thereof as described herein comprises two heavy chain variable regions of SEQ ID NO: 76 and two light chain variable regions of SEQ ID NO: 16.

In one embodiment, the antibody of the invention comprises:

(A) a heavy chain having a VH comprising the amino acid sequence set forth in SEQ ID No. 10, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In another embodiment, the antibody of the invention comprises:

(A) a heavy chain having a VH comprising the amino acid sequence set forth in SEQ ID No. 11, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In another embodiment, the antibody of the invention comprises:

(A) a heavy chain having a VH comprising the amino acid sequence set forth in SEQ ID No. 12, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 43, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 75, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 70, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 84, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 88, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 40, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 83, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 78, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 47, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

In one embodiment, the antibody of the invention comprises:

(A) a heavy chain having a VH comprising the amino acid sequence set forth in SEQ ID No. 76, and a heavy chain constant region comprising the amino acid sequence set forth in SEQ ID No. 17; and (B) a light chain having a VL comprising the amino acid sequence set forth in SEQ ID No. 16, and a light chain constant region comprising the amino acid sequence set forth in SEQ ID No. 18.

The invention further provides a binding domain that specifically binds to human TGF-βRII, wherein the binding domain comprises:

any one of the heavy chain variable regions (VH) selected from:

(A) a VH having a VH-CDR1, VH-CDR2, and VH-CDR3 of the VH having an amino acid sequence set forth in SEQ ID No. 12;

(B) a VH having a VH-CDR1, VH-CDR2, and VH-CDR3 of the VH having an amino acid sequence set forth in SEQ ID No. 26;

(C) a VH having a VH-CDR1, VH-CDR2, and VH-CDR3 of the VH having an amino acid sequence set forth in SEQ ID No. 30;

(D) a VH having a VH-CDR1, VH-CDR2, and VH-CDR3 of the VH having an amino acid sequence set forth in SEQ ID No. 40;

(E) a VH having a VH-CDR1, VH-CDR2, and VH-CDR3 of the VH having an amino acid sequence set forth in SEQ ID No. 61;

(F) a VH having a VH-CDR1, VH-CDR2, and VH-CDR3 of the VH having an amino acid sequence set forth in SEQ ID No. 65;

(G) a VH having a VH-CDR1, VH-CDR2, and VH-CDR3 of the VH having an amino acid sequence set forth in SEQ ID No. 70;

(H) a VH having a VH-CDR1, VH-CDR2, and VH-CDR3 of the VH having an amino acid sequence set forth in SEQ ID No. 76;

(I) a VH having a VH-CDR1, VH-CDR2, and VH-CDR3 of the VH having an amino acid sequence set forth in SEQ ID No. 85; and (J) a VH having a VH-CDR1, VH-CDR2, and VH-CDR3 of the VH having an amino acid sequence set forth in SEQ ID No. 86;

wherein one to five amino acid residue(s) may be substituted with conservative amino acid(s) thereof in any one or more of the CDR(s) selected from VH-CDR1, VH-CDR2 and VH-CDR3.

The VH-CDR1, VH-CDR2, and VH-CDR3 sequences are indicated in bold and underlined in the listing of sequences provided herein.

In one embodiment, the binding domain of the present invention comprises a VH amino acid sequence selected from SEQ ID NO: 12, 26, 30, 40, 61, 65, 70, 76, 85 and 86, or a VH amino acid sequence having at least 80% identity thereto.

The binding domains of the present invention have shown to be useful in monovalent and multivalent form, providing for a variety of applications in monovalent molecules or bivalent molecules, or as one or more binding domains incorporated into a multispecific molecule. Said binding domains in monovalent form have superior TGF-βRII blocking capabilities as compared to a monovalent control antibody, rendering them suitable for the above applications.

In certain embodiments, the present invention provides an antibody, preferably a multispecific antibody, comprising the binding domain of the present invention in monovalent form, which antibody has comparable receptor blocking activity at equimolar concentrations when compared to a bivalent monospecific control antibody, preferably as measured in the same assay. In certain embodiments, the control antibody comprises two heavy chain variable regions having an amino acid sequence as set forth in SEQ ID NO: 97 and two light chain variable regions having an amino acid sequence as set forth in SEQ ID NO: 135. In certain embodiments, the assay is a TGFβ-reporter assay, preferably a TGFβ-reporter assay as described in Example 5. In certain embodiments, the comparable receptor blocking activity includes a 5 to 2 fold, preferably a 3 fold, deviation, from the receptor blocking activity of the control antibody.

The antibodies and binding domains described and claimed herein, such as for instance those described in the embodiments above, are preferably isolated antibodies or binding domains. Preferably, they are monoclonal antibodies. More preferably, they are isolated monoclonal antibodies.

The antibody or antibody fragment, or binding domain, of the present invention interferes with binding of ligands TGF-β1, TGF-β2, and/or TGF-β3 to TGF-βRII. The term "interferes with binding" means that the antibody or antibody fragment is directed to an epitope on TGF-βRII and competes with TGB-β1, TGB-β2, and/or TGB-β3 for binding to TGF-βRII. The antibody or antibody fragment, or binding domain, may diminish ligand binding, displace ligand binding when this is already bound to TGF-βRII, or may, for instance through steric hindrance, at least partially prevent ligand from binding to TGF-βRII, and/or interfere or prevent TGF-βRI-TGF-βRII complex formation. The antibody or antibody fragment, or binding domain, may diminish the formation of a TGF-βRI and TGF-βRII complex, displace such complex, when a complex is already formed, or may, for instance through steric hindrance, at least partially prevent TGF-βRI from complexing with TGF-βRII. The term "interferes with binding" also means that the antibody or antibody fragment, or binding domain, of the present invention blocks binding of ligands TGF-β 1, TGF-β2, and/or TGF-β3 to TGF-βRII.

The present invention further provides an expression vector comprising a polynucleotide encoding either or both the heavy chain and the light chain of the antibody or antibody fragment, or binding domain, as described herein. Examples of vectors include plasmids, phagemids, cosmids, viruses and phage nucleic acids or other nucleic acid molecules that are capable of replication in a prokaryotic or eukaryotic host cell, e.g. a mammalian cell. The vector may be an expression vector wherein the polynucleotide encoding either or both the heavy chain and the light chain of the antibody or antibody fragment of the invention is operably linked to expression control elements. Typical expression vectors contain transcription and translation terminators, initiation sequences, and promoters useful for regulation of the expression of the polynucleotides.

In the art various methods exist to produce antibodies. Antibodies are typically produced by a cell that expresses nucleic acid encoding the antibody. The invention therefore also provides an isolated cell, or a cell in a tissue culture, that produces and/or comprises the antibody or antibody fragment of the invention. Typically this is an in vitro, isolated or recombinant cell. Such cell comprises a nucleic acid encoding the antibody or antibody fragment of the invention. The cell is preferably an animal cell, more preferably a mammalian cell, more preferably a primate cell, most preferably a human cell. For the purposes of the invention a suitable cell is any cell capable of comprising and preferably of producing an antibody according to the invention and/or comprising a nucleic acid according to the invention. Preferably, the cell is a hybridoma cell, a Chinese hamster ovary (CHO) cell, an NS0 cell or a PER.C6 cell. It is particularly preferred that the cell is a CHO cell.

Further provided is a cell culture, or cell line, comprising a cell according to the invention. Cell lines developed for industrial scale production of proteins and antibodies are herein further referred to as industrial cell lines.

The invention further provides a method for producing the antibody or antibody fragment, or binding domain, of the invention, the method comprising culturing a cell of the invention and harvesting the antibody or antibody fragment, or binding domain, from said culture. Said cell may be cultured in a serum free medium. Preferably said cell is adapted for suspension growth. The antibody or antibody fragment, or binding domain, may be purified from the medium of the culture. Preferably said antibody or antibody fragment, or binding domain, is affinity purified.

The present invention further provides a pharmaceutical composition comprising an antibody or antibody fragment, or binding domain, as described herein, and a pharmaceutically acceptable carrier, diluent, or excipient.

When the antibody or antibody fragment of the present invention is formulated to be used as an injection or infusion solution for drip infusion, the injection or infusion solution may be in any form of an aqueous solution, suspension, or emulsion, or may be formulated as a solid agent together with pharmaceutically acceptable carrier such that that agent will be dissolved, suspended, or emulsified in a solvent at the time of use. Examples of the solvent that is used in the injection or the infusion solution for drip infusion include distilled water for injection, physiological saline, glucose solutions, and isotonic solutions (e.g., in which sodium chloride, potassium chloride, glycerin, mannitol, sorbitol, boric acid, borax, propylene glycol or the like is soluble).

Examples of pharmaceutically acceptable carriers include stabilizers, solubilizers, suspending agents, emulsifiers, soothing agents, buffering agents, preservatives, antiseptic agents, pH adjusters, and antioxidants. As stabilizers, various amino acids, albumin, globulin, gelatin, mannitol, glucose, dextran, ethylene glycol, propylene glycol, polyethylene glycol, ascorbic acid, sodium bisulfite, sodium thiosulfate, sodium edetate, sodium citrate, dibutylhydroxytoluene, or the like, can be used. As solubilizers, alcohols (e.g., ethanol), polyols (e.g., propylene glycol and polyethylene glycol), nonionic surfactants (e.g., Polysorbate 20 (registered trademark), Polysorbate 80 (registered trademark) and HCO-50), or the like, can be used. As suspending agents, glyceryl monostearate, aluminum monostearate, methyl cellulose, carboxymethyl cellulose, hydroxymethyl cellulose, sodium lauryl sulfate, or the like, can be used. As emulsifiers, gum arabic, sodium alginate, tragacanth, or the like, can be used. As soothing agents, benzyl alcohol, chlorobutanol, sorbitol, or the like, can be used. As buffering agents, phosphate buffer, acetate buffer, borate buffer, carbonate buffer, citrate buffer, Tris buffer, glutamic acid buffer, epsilon aminocaproic acid buffer, or the like, can be used. As preservatives, methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edeate, boric acid, borax, or the like, can be used. As antiseptic agents, benzalkonium chloride, parahydroxybenzoic acid, chlorobutanol, or the like, can be used. As the pH adjusters, hydrochloric acid, sodium hydroxide, phosphoric acid, acetic acid, or the like, can be used. As antioxidants, (1) aqueous antioxidants such as ascorbic acid, cysteine hydrochloride, sodium bisulfate, sodium metabisulfite, and sodium sulfite, (2) oil-soluble antioxidants such as ascorbyl palmitate, butylated hydroxy anisole, butylated hydroxy toluene, lecithin, propyl gallate, and α-tocopherol, or (3) metal chelating agents such as citric acid, ethylenediaminetetraacetic acid, sorbitol, tartaric acid, and phosphoric acid, can be used.

The injection or infusion solution for drip infusion can be produced by performing sterilization in the final process, or aseptic manipulation, e.g., sterilization by filtration with a filter and subsequently filling an aseptic container. The injection or infusion solution for drip infusion may be used by dissolving the vacuum dried or lyophilized aseptic powder (which may include a pharmaceutically acceptable carrier powder) in an appropriate solvent at the time of use.

The invention further provides a method of treating cancer in a subject comprising administering an effective amount of an antibody or antibody fragment, binding domain, or a pharmaceutical composition, as described herein to the subject in need thereof. As such, the invention provides an antibody or antibody fragment, or biding domain, as described herein for use in the treatment of cancer in a subject. The invention further provides a pharmaceutical agent for use in for preventing, suppressing symptom progression or recurrence of, and/or treating cancer, wherein the pharmaceutical agent comprises the antibody or antibody fragment thereof, or binding domain, as described herein as an active ingredient.

Cancer patients usually have aberrant cells that are to be removed from the body. The term 'aberrant cells' as used herein includes tumor cells, more specifically tumor cells present on any type of cancerous tissues associated with cancer-types correlated with higher than normal TGF-βRII expression. Aberrant cells herein further refers to those having increased signaling as a consequence of increased expression of TGF-β and/or release of TGF-β, and those forming a suppressive environment reducing effectiveness of tumor immunity due to abnormal TGF-β signaling and/or expression or higher than normal TGF-β, TGF-βRI and/or TGF-βRII expression, and/or higher than normal release of latent TGF-β.

The antibody or antibody fragment, or binding domain, of the invention will be effective in the treatment of several types of cancer, including for instance cancer-types correlated with higher than normal TGF-β signaling, in particular with higher than normal TGF-βRII expression. Examples include, but are not limited to, breast cancer, colon cancer, colorectal cancer, gastric cancer, glioblastoma, neck cancer, hepatocellular carcinoma, non-small cell lung cancer, small cell lung cancer, melanoma, myelodysplastic syndrome, pancreatic cancer, prostate cancer and renal cancer.

The antibody or antibody fragment, or binding domain, of the present invention blocks binding of human TGF-β to human TGF-βRII on the cell, thereby inhibiting TGF-βRII signaling. This leads to decreased proliferation of deleterious or aberrant cells and/or enhanced tumor immunity and other beneficial effect.

The invention therefore also provides a method of blocking binding of human TGF-β to human TGF-βRII on a cell, the method comprising providing the antibody or antibody fragment, or binding domain, as described herein to the cell and allowing the antibody or antibody fragment to bind to the human TGF-βRII of the cell, to thereby block binding of human TGF-β to human TGF-βRII on the cell. This may be an in vitro method.

Depending on the desired activity, the antibody of the present invention may have modulated effector function. Antibody-dependent cellular cytotoxicity (ADCC), also referred to as antibody-dependent cell-mediated cytotoxicity, is a mechanism of cell-mediated immune defence whereby an effector cell of the immune system actively lyses a target cell, whose membrane-surface antigens have been bound by specific antibodies. ADCC effector function is typically mediated by Fc receptors (FcRs). The receptors are key immune regulatory receptors connecting the antibody mediated (humoral) immune response to cellular effector functions. Receptors for all classes of immunoglobulins have been identified, including FcγR (IgG), FcεRI (IgE), FcαRI (IgA), FcμR (IgM) and FcδR (IgD). There are three classes of receptors for human IgG found on leukocytes: CD64 (FcγRI), CD32 (FcγRIIa, FcγRIIb and FcγRIIc) and CD16 (FcγRIIIa and FcγRIIIb). FcγRI is classed as a high affinity receptor (nanomolar range KD) while FcγRII and FcγRIII are low to intermediate affinity (micromolar range KD). In antibody dependent cellular cytotoxicity (ADCC), FcvRs on the surface of effector cells (natural killer cells, macrophages, monocytes and eosinophils) bind to the Fc region of an IgG which itself is bound to a target cell. Upon binding, a signalling pathway is triggered which results in the secretion of various substances, such as lytic enzymes, perforin, granzymes and tumour necrosis factor, which mediate in the destruction of the target cell. The level of ADCC effector function varies for human IgG subtypes.

Although this is dependent on the allotype and specific FcγR in simple terms ADCC effector function is high for human IgG1 and IgG3, and low for IgG2 and IgG4. Knowledge of the binding site of the FcvRs on the antibody has resulted in engineered antibodies that do not have ADCC effector functions.

Another type of effector function is independent on effector cells and is referred to as complement-dependent cytotoxicity (CDC). This is an effector function of IgG and IgM antibodies. It is another mechanism of action by which therapeutic antibodies or antibody fragments can achieve an antitumor effect. CDC is initiated when C1q, the initiating component of the classical complement pathway, is fixed to the Fc portion of target-bound antibodies. This is the first step of a complex complement activation cascade that can ultimately result in the lysis of the antibody marked cell.

In an antibody of the invention, ADCC activity can be enhanced by different techniques by slightly modifying the constant region, one of them being the removal of fucose. Removal of fucose has resulted in increased anti-tumour activity in several in vivo models (Junttila et al., Cancer Research (2010), Vol. 70(22), pp. 4481-4489). Afucosylation technology may be applied, thereby preventing fucosylation of the N-linked carbohydrate structure in the Fc region.

In an antibody of the invention, effector function can also be reduced or eliminated. For instance, leucine at position 235 according to the EU numbering system may be substituted with glycine, and/or glycine at position 236 according to the EU numbering system may be substituted with arginine. Such modification(s) ensure that binding to an Fc receptor and/or effector function is eliminated or decreased. Other substitutions, deletions, or insertions known in the art to the same effect are also encompassed within the present invention.

The invention further provides a method of inhibiting signal transduction into a cell induced by binding of a human TGF-β to a human TGF-βRII of the cell, the method comprising providing the antibody or antibody fragment, or binding domain, as described herein to the cell and allowing the antibody or antibody fragment to bind to the human TGF-βRII of the cell, to thereby inhibit the signal transduction into the cell. This may be an in vitro method.

The invention also provides a method of preventing or inhibiting metastasis, the method comprising administering an effective amount of the antibody or antibody fragment, binding domain, or the pharmaceutical composition, as described herein, to a subject.

The antibody or antibody fragment, or binding domain, of the present invention may be used in the treatment of cancer as a single therapy but may also be combined with other anti-cancer agents. Other anti-cancer agents include, but are not limited to, therapeutic antibodies that target the same or different tumor antigens or modulate elements of the immune system, agents used in chemotherapy (e.g. cyclophosphamide), and agents used in hormone therapy, or in applications related to localized administration including an oncolytic virus. Treatment with the antibody or antibody fragment, or binding domain, of the present invention may also be combined with other anti-cancer treatments, such as for instance surgery or radiotherapy. Combinations of treatment can be simultaneous, separate, or sequential.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

"Plurality" means two or more.

Note that in the present specification, unless stated otherwise, amino acid positions assigned to CDRs and frameworks in a variable region of an antibody or antibody fragment are specified according to Kabat's numbering (see Sequences of Proteins of Immunological Interest (National Institute of Health, Bethesda, Md., 1987 and 1991)). Amino acids in the constant regions are indicated according to the EU numbering system based on Kabat's amino acid positions (see Sequences of proteins of immunological interest, NIH Publication No. 91-3242).

Accession numbers are primarily given to provide a further method of identification of a target, the actual sequence of the protein bound may vary, for instance because of a mutation in the encoding gene such as those occurring in some cancers or the like. The antigen binding site binds the antigen and a variety of variants thereof, such as those expressed by some antigen positive immune or tumor cells.

When herein reference is made to a gene, a protein, the reference is preferably to the human form of the gene or protein. When herein reference is made to a gene or protein reference is made to the natural gene or protein and to variant forms of the gene or protein as can be detected in tumors, cancers and the like, preferably as can be detected in human tumors, cancers and the like.

HGNC stands for the HUGO Gene nomenclature committee. The number following the abbreviation is the accession number with which information on the gene and protein encoded by the gene can be retrieved from the HGNC database. Entrez Gene provides the accession number or gene ID with which information on the gene or protein encoded by the gene can be retrieved from the NCBI (National Center for Biotechnology Information) database. Ensemble provides the accession number with which information on the gene or protein encoded by the gene can be obtained from the Ensemble database. Ensembl is a joint project between EMBL-EBI and the Wellcome Trust Sanger Institute to develop a software system which produces and maintains automatic annotation on selected eukaryotic genomes.

BRIEF DESCRIPTION OF THE DRAWINGS

FIG. 1 presents the amino acid sequences of the IGKV1-39 light chain variable V region (FIG. 1A); IGKV1-39/jk1 light chain variable region (FIG. 1B); and IGKV1-39/jk5 light chain variable region (FIG. 1C).

FIG. 2 presents the FACS data of antibody binding to endogenously expressed TGF-βRII on CCD18Co cells. FIG. 2A shows the MFI PE of antibodies comprising heavy chain variable regions having SEQ ID NO: 92 (negative control); SEQ ID NO: 93; and SEQ ID NO: 94. FIG. 2B shows the MFI PE of antibodies comprising heavy chain variable regions having SEQ ID NO: 92 (negative control); SEQ ID NO: 10; SEQ ID NO: 11; SEQ ID NO: 12; SEQ ID NO: 95; and SEQ ID NO: 96.

FIG. 3 presents the ELISA data of ligand blocking activity of antibodies comprising heavy chain variable regions having SEQ ID NO: 92 (negative control); SEQ ID NO: 93; and SEQ ID NO: 94 (FIG. 3A), and of antibodies comprising heavy chain variable regions having SEQ ID NO: 92 (negative control); SEQ ID NO: 10; SEQ ID NO: 11; SEQ ID NO: 12; SEQ ID NO: 95; and SEQ ID NO: 96 (FIG. 3B).

Figure 4:
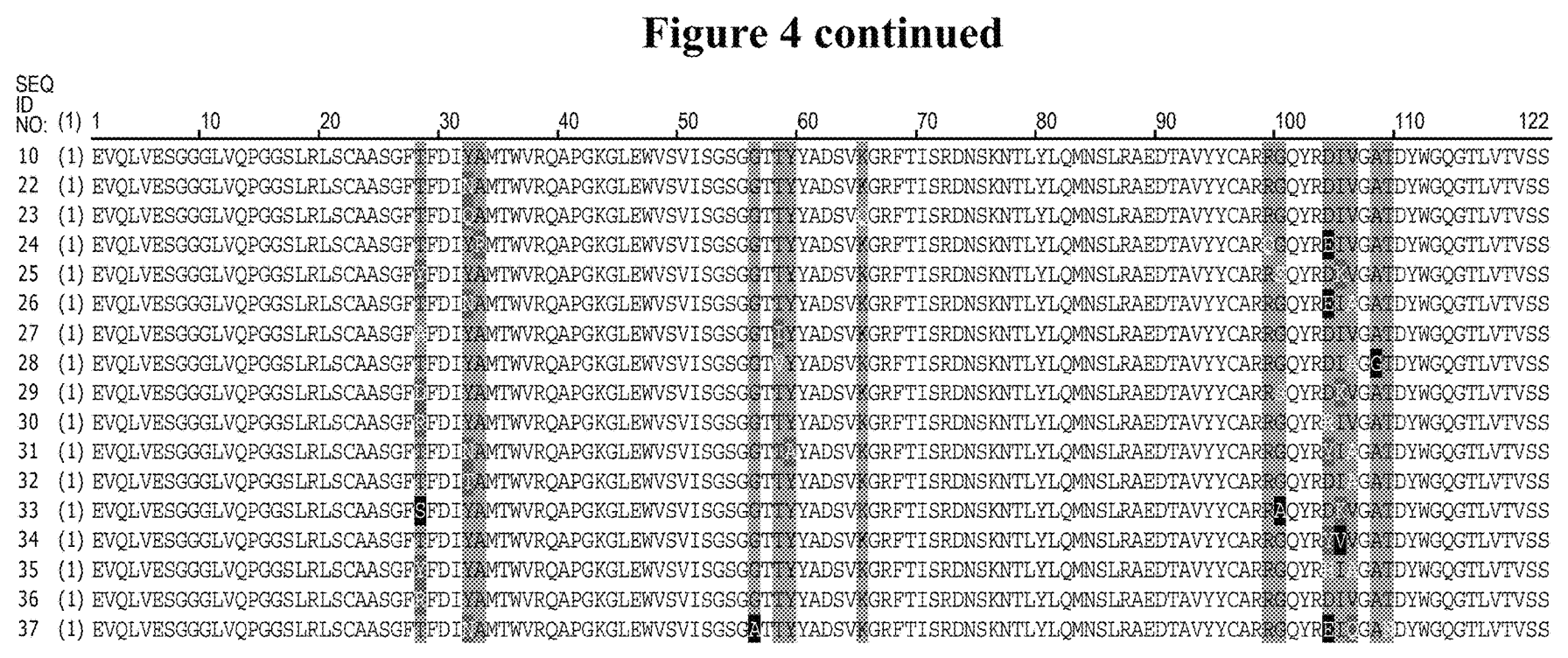
Figure 4:
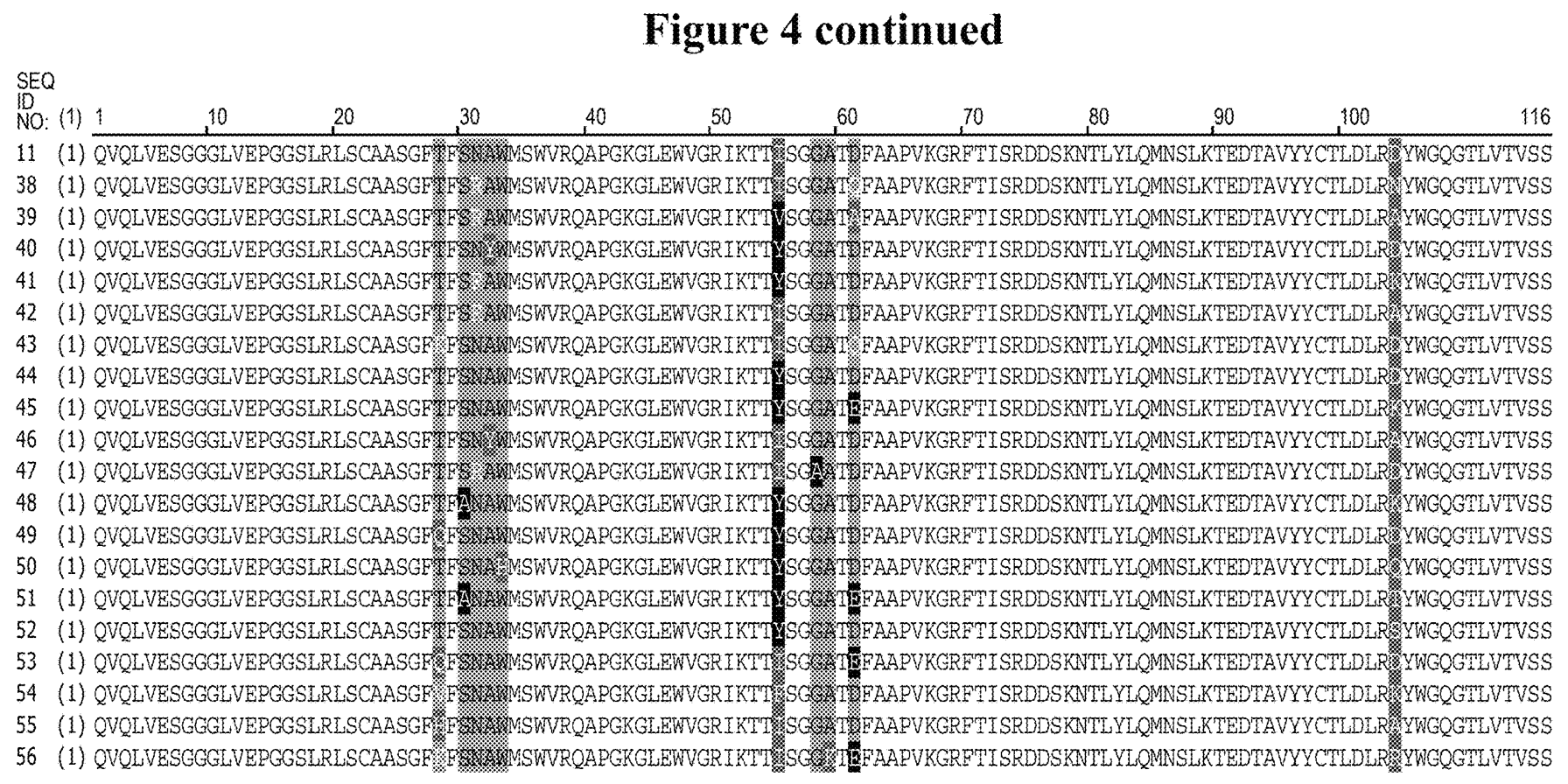

FIG. 4 presents an amino acid sequence alignment generated using the AlignX application of the Vector NTI Program Advance 11.5.2 software of the heavy chains comprising heavy chain variable regions having SEQ ID NO: 10 (middle alignment); SEQ ID NO: 11 (bottom alignment); and SEQ ID NO: 12 (top alignment) with their respective affinity matured variants. Identical amino acids are indicated with black letters against a white background; weakly similar amino acids are indicated with white letters against a grey background; conservative changes are indicated with black letters against a grey background; and non-similar amino acids are indicated with white letters against a dark grey background.

FIG. 7A presents an overview of how critical residues are identified and mapped. FIG. 7B shows the mean fluorescence of SEQ ID NO: 10; SEQ ID NO: 12; and SEQ ID NO: 93, as a percentage compared to wildtype.

Figure 5:
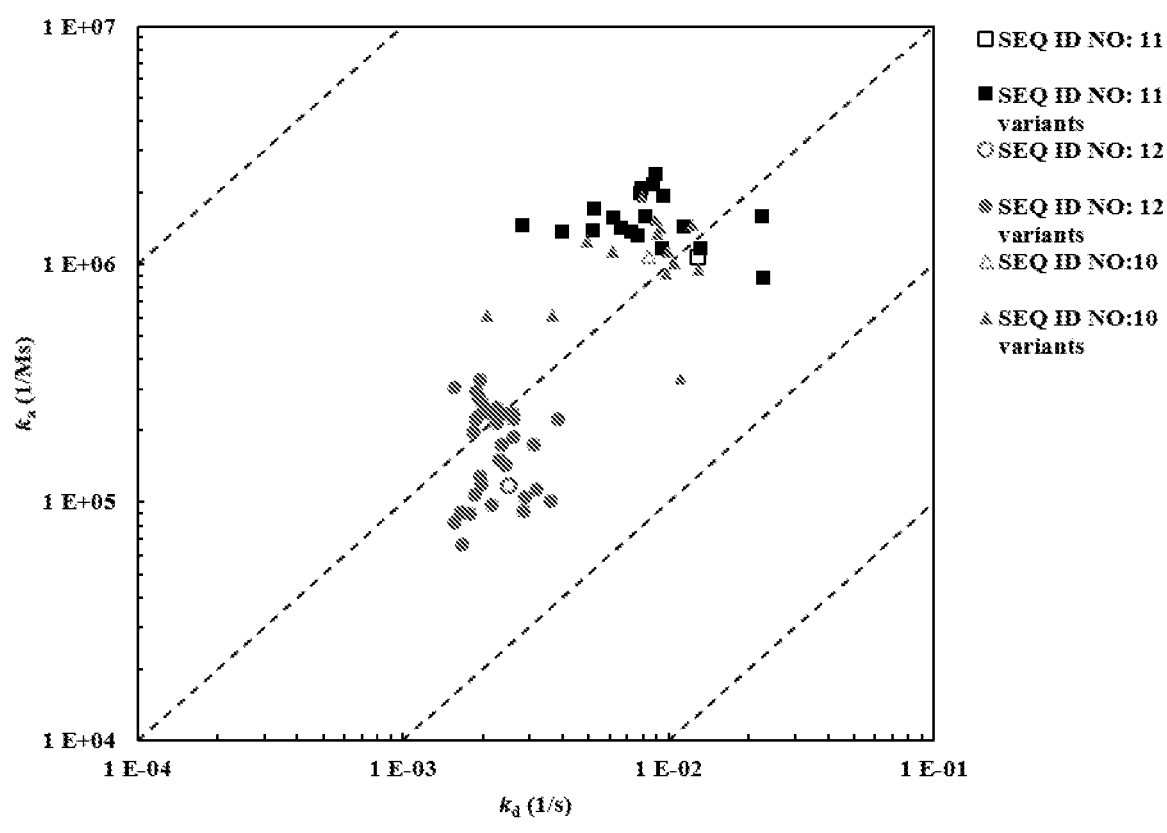
FIG. 5 shows the binding affinity of the parental antibodies (SEQ ID NO: 10; SEQ ID NO: 11; SEQ ID NO: 12) and the affinity matured variants (SEQ ID NO: 10 variants; SEQ ID NO: 11 variants; SEQ ID NO: 12 variants). $k_a$=on-rate in 1/Ms. $k_d$=off-rate in 1/s.

A) Δ TGF-βRII binding domain comprising a heavy chain variable region having amino acid sequence as set forth in SEQ ID NO: 76; □ TGF-βRII binding domain comprising a heavy chain variable region having amino acid sequence as set forth in SEQ ID NO: 61; • TGF-βRII binding domain comprising a heavy chain variable region having amino acid sequence as set forth in SEQ ID NO: 26.

B) ○ TGF-βRII binding domain comprising a heavy chain variable region having amino acid sequence as set forth in SEQ ID NO: 70; *TGF-βRII binding domain comprising a heavy chain variable region having amino acid sequence as set forth in SEQ ID NO: 70; □ TGF-βRII binding domain comprising a heavy chain variable region having amino acid sequence as set forth in SEQ ID NO: 61; • TGF-βRII binding domain comprising a heavy chain variable region having amino acid sequence as set forth in SEQ ID NO: 86; Δ

TGF-βRII binding domain comprising a heavy chain variable region having amino acid sequence as set forth in SEQ ID NO: 65.

C) *TGF-βRII binding domain comprising a heavy chain variable region having amino acid sequence as set forth in SEQ ID NO: 65; ○ TGF-βRII binding domain comprising a heavy chain variable region having amino acid sequence as set forth in SEQ ID NO: 40; • TGF-βRII binding domain comprising a heavy chain variable region having amino acid sequence as set forth in SEQ ID NO: 12; □ TGF-βRII binding domain comprising a heavy chain variable region having amino acid sequence as set forth in SEQ ID NO: 76; Δ TGF-βRII binding domain comprising a heavy chain variable region having amino acid sequence as set forth in SEQ ID NO: 26.

D) • TGF-βRII binding domain comprising a heavy chain variable region having amino acid sequence as set forth in SEQ ID NO: 12; □ TGF-βRII binding domain comprising a heavy chain variable region having amino acid sequence as set forth in SEQ ID NO: 85.

E) • TGF-βRII binding domain comprising a heavy chain variable region having amino acid sequence as set forth in SEQ ID NO: 86.

The following Examples illustrate the invention but are not intended to limit the invention in any way.

EXAMPLES

Example 1—Antibody Production

Transgenic mice comprising a common IGKV1-39 light chain (MeMo® mice) were immunized with human TGF-βRII (isoform A), thereby generating an immune response including the production of human anti-TGF-βRII specific antibodies. Lymphoid material of the immunized mice was collected, from which nucleic acids were extracted and used for the synthesis of cDNA encoding the heavy chain variable regions of such antibodies. The cDNA was used to generate phage display libraries, from which human TGF-βRII binding Fabs were selected using the Kingfisher selection robot.

Two rounds of affinity-driven selections with different concentrations of biotinylated recombinant protein were performed using the Kingfisher robot. Human TGF-βRII-Fc was biotinylated with the EZ-Link™ Sulfo-NHS-Biotin kit (ThermoFisher; cat. no. 21217) according to the protocol of the manufacturer, aliquoted and stored at −20° C. until further use. Two subsequent rounds of in-solution selections were performed with the biotinylated human TGF-βRII-Fc using the Kingfisher robot. In the first round of selection, three different concentrations of protein were used. As a negative control, selections without antigen were included. 50 μg/ml of total human IgG (Sigma; cat. no. 1456) was added in solution during all phage library incubations to minimize the selection of Fc binders. After washing, bound phage was eluted with trypsin. Phage output was determined according to the spot method, wherein TG1 cells were infected and plated on LB agar amp/glu plates for picking single colonies for screening. A second round of selection was performed with the outputs from the first round. In the second round of selection, TGF-βRII-Fc-biotin was used at decreasing amounts of protein starting at the concentration used for the respective first selection round output.

Colonies were picked into 96-wells plates for preparation of periplasmic extracts containing soluble Fab. The obtained Fab-containing fractions were used for identification of TGF-βRII specific clones using FACS.

Human TGF-βRII transiently transfected HEK293T cells were used for FACS screening. The Fab end-concentration was between 0.5 and 5 μg/ml. Fabs binding TGF-βRII were detected with goat anti-kappa light chain antibodies (Ab0646; 5 μg/ml) followed by rabbit anti-goat PE (Ab0330; 1/100 dilution).

Two rounds of immunization were performed resulting in a large panel of Fabs for further characterization. In the second round of immunization, a different vector was used to increase expression levels and the mice were co-immunized with human TGF-βRI. This may have contributed to a higher immune response generated in the mice observed during the second round of immunization.

A positive control antibody was produced based on information obtained from US 2010/0119516. This positive control antibody comprises two heavy chain variable regions and two light chain variable regions having the amino acid sequences of mAb TGF1 (SEQ ID NO: 97 and SEQ ID NO: 135 respectively) described therein. An antibody comprising these heavy and light chain variable regions is reported to block ligand binding to TGF-βRII.

A negative control antibody against RSV was produced. This negative control antibody comprises two heavy chain variable regions having an amino acid sequence as set forth in SEQ ID NO: 136 and two light chain variable regions as set forth in SEQ ID NO: 16.

Example 2—Antibody Characterization

The VH fragments of the TGF-βRII binding Fabs identified in Example 1 were recloned into an IgG expression format to express and purify IgG from 293T freestyle cells.
Antigen Binding Antibodies were screened for binding to endogenously expressed human TGF-βRII on CCD18Co cells using FACS. Results are shown in FIG. 2. All antibodies tested showed similar binding to the CCD18Co cells.

The Fab comprising heavy chain variable regions having an amino acid set forth in SEQ ID NO: 11, obtained from the first round of immunization, comprises the same HCDR3 sequence as Fabs obtained from the second round of immunization, for example the Fab comprising heavy chain variable regions having an amino acid sequence set forth in SEQ ID NO: 93. This indicates that the recombination of VDJ gene segments in the mice is to a great extent the same in response to this antigen.
Binding Affinity The binding affinity of antibodies comprising heavy chain variable regions having an amino acid sequence set forth in SEQ ID NO: 10, SEQ ID NO: 11, SEQ ID NO: 93 and SEQ ID NO: 12 was determined by SPR. For this, the antibodies were reformatted as bivalent IgG's monospecific for TGFβRII.

Anti-TGF-βRII IgG antibodies were captured on a CM5 sensor chip surface by an immobilized anti-CH1 antibody (Ab0669; BD cat. no. BD555784), followed by the addition of human recombinant TGF-βRII (R&D systems cat. no. 241-R2/CF; region Ile24-Aps195). Measurements were carried out at 25° C. Coupling was performed at pH 4.5. Results are shown in Table 2.

TABLE 2

Binding affinity of selected antibodies to TGF-βRII.

| IgG | $k_{on}$ (1/Ms) | $k_{off}$ (1/s) | $K_d$ (nM) |
|---|---|---|---|
| SEQ ID NO: 10 | 9.698*10E+5 | 4.313*10E−3 | 4.45 |
| SEQ ID NO: 11 | 1.232*10E+6 | 1.021*10-2 | 8.29 |

TABLE 2-continued

| Binding affinity of selected antibodies to TGF-βRII. | | | |
|---|---|---|---|
| IgG | $k_{on}$ (1/Ms) | $k_{off}$ (1/s) | $K_d$ (nM) |
| SEQ ID NO: 93 | 1.074*10E+6 | 7.104*10E-3 | 6.61 |
| SEQ ID NO: 12 | 1.028*10E+5 | 7.519*10E-4 | 7.31 |

Ligand Blocking

Ligand blocking activity of the IgG samples was determined using an ELISA assay.

An ELISA plate was coated with TGF-β1 at 0.4 μg/ml. Human TGF-βRII-Fc (R&D; cat. no. 341-BR) was added with an end concentration of 0.01 μg/ml. Antibodies were incubated in a three-fold concentration range starting at an end concentration of 10 μg/ml. An antibody that specifically binds tetanus toxoid comprising a heavy chain variable region having an amino acid sequence as set forth in SEQ ID NO: 92, was included as a control. Antibodies that bind human TGF-βRII-Fc were detected with a biotin-conjugated anti-human Fc antibody (1:10.000) and streptavidin-HRP (1:2000).

As shown in FIG. 3, all antibodies tested show good ligand blocking activity when compared to the control antibody. The IC50 values of selected antibodies are presented in Table 3.

TABLE 3

| IC50 values of selected antibodies. | |
|---|---|
| IgG | IC50 (ug/ml) |
| SEQ ID NO: 93 | 0.1551 |
| SEQ ID NO: 10 | 0.138 |
| SEQ ID NO: 11 | 0.5264 |
| SEQ ID NO: 12 | 0.1252 |

Example 3—Affinity Maturation

Fab phage display libraries of variant heavy chains comprising variable heavy chain regions having an amino acid sequence set forth in SEQ ID NO: 10, SEQ ID NO: 11, and SEQ ID NO: 12, that specifically bind TGF-βRII and block ligand interaction and TGF-βRII and TGF-βRI heterodimerization, were generated to evaluate whether antibodies could be produced with higher affinity. The library was designed to generate heavy chain variable regions with increased affinity and having typically three to four variations: one in CDR1, one in CDR2, and one or two in CDR3, with certain number of variants having more than 4 variations overall. An overview of the variants is provided as a sequence alignment in FIG. 4.

Variants with higher affinity were selected using two different selection methods, both with biotinylated human TGF-βRII-Fc as antigen, and both using the Kingfisher selection robot. Several selection rounds were performed. The first selection round comprised an affinity based selection as described in Example 1, using different concentrations of biotinylated TGF-βRII-Fc. Only the output from the selection with the lowest antigen concentration showing clear enrichment was subsequently further used in two separate selection methods. The first selection method entails two additional rounds of affinity based selections, however, this time with further decreasing concentrations of antigen as compared to the optimal antigen concentration used in the preceding selection round. The second selection method also entails two additional rounds of selections which are both affinity based, via decreasing concentrations of antigen, as well as off-rate based, via including a wash step in the presence of an excess of non-biotinylated antigen.

50 μg/ml of total human IgG (Sigma; cat. no. I4506) was added in solution during all phage library incubations to minimize the selection of Fc binders. After washing, bound phage was eluted with trypsin. Phage output was determined according to the spot method, wherein TG1 cells were infected with serial dilutions of phage outputs and plated on LB agar amp/glu plates for counting colonies the next day.

Phage outputs were rescued via bacterial infection to generate sufficient phages for subsequent selections, as well as to generate plates with bacterial colonies. Colonies were picked into 96-wells plates for antibody production. The generated antibodies were used for the preparation of periplasmic extracts containing soluble Fabs.

Affinity matured variants were reformatted as bivalent IgG's monospecific for TGFβRII. SPR analysis was performed to determine the affinity of the variants for TGF-βRII. Results are shown in Table 4 and FIG. 5.

TABLE 4

| affinity of affinity matured variants and parental antibodies. | | | |
|---|---|---|---|
| IgG | $k_{on}$ (1/Ms) | $k_{off}$ (1/s) | $K_d$ (M) |
| SEQ ID NO: 44 | 1.37E+06 | 3.99E-03 | 2.90E-09 |
| SEQ ID NO: 49 | 1.39E+06 | 5.24E-03 | 3.76E-09 |
| SEQ ID NO: 53 | 1.43E+06 | 1.15E-02 | 8.07E-09 |
| SEQ ID NO: 43 | 1.57E+06 | 6.20E-03 | 3.96E-09 |
| SEQ ID NO: 40 | 1.46E+06 | 2.82E-03 | 1.93E-09 |
| SEQ ID NO: 47 | 1.99E+06 | 7.83E-03 | 3.94E-09 |
| SEQ ID NO: 48 | 1.31E+06 | 7.71E-03 | 5.88E-09 |
| SEQ ID NO: 45 | 1.41E+06 | 6.68E-03 | 4.74E-09 |
| SEQ ID NO: 41 | 1.36E+06 | 7.28E-03 | 5.34E-09 |
| SEQ ID NO: 54 | 1.16E+06 | 1.33E-02 | 1.15E-08 |
| SEQ ID NO: 55 | 1.58E+06 | 2.25E-02 | 1.42E-08 |
| SEQ ID NO: 46 | 2.39E+06 | 8.94E-03 | 3.74E-09 |
| SEQ ID NO: 42 | 2.16E+06 | 8.80E-03 | 4.08E-09 |
| SEQ ID NO: 39 | 1.71E+06 | 5.26E-03 | 3.08E-09 |
| SEQ ID NO: 50 | 1.17E+06 | 9.49E-03 | 8.12E-09 |
| SEQ ID NO: 51 | 1.58E+06 | 8.23E-03 | 5.21E-09 |
| SEQ ID NO: 52 | 1.92E+06 | 9.56E-03 | 4.98E-09 |
| SEQ ID NO: 38 | 2.07E+06 | 7.97E-03 | 3.85E-09 |
| SEQ ID NO: 56 | 8.74E+05 | 2.28E-02 | 2.61E-08 |
| SEQ ID NO: 11 | 1.07E+06 | 1.29E-02 | 1.21E-08 |
| SEQ ID NO: 84 | 2.32E+05 | 2.49E-03 | 1.07E-08 |
| SEQ ID NO: 76 | 2.91E+05 | 1.90E-03 | 6.54E-09 |
| SEQ ID NO: 71 | 1.95E+05 | 1.85E-03 | 9.53E-09 |
| SEQ ID NO: 80 | 2.28E+05 | 1.93E-03 | 8.46E-09 |
| SEQ ID NO: 88 | 1.73E+05 | 2.38E-03 | 1.38E-08 |
| SEQ ID NO: 73 | 1.43E+05 | 2.46E-03 | 1.72E-08 |
| SEQ ID NO: 67 | 2.40E+05 | 2.07E-03 | 8.63E-09 |
| SEQ ID NO: 77 | 2.34E+05 | 2.61E-03 | 1.11E-08 |
| SEQ ID NO: 75 | 2.21E+05 | 1.91E-03 | 8.63E-09 |
| SEQ ID NO: 85 | 2.21E+05 | 3.88E-03 | 1.76E-08 |
| SEQ ID NO: 58 | 8.87E+04 | 1.79E-03 | 2.02E-08 |
| SEQ ID NO: 65 | 8.11E+04 | 1.58E-03 | 1.95E-08 |
| SEQ ID NO: 59 | 9.00E+04 | 1.66E-03 | 1.85E-08 |
| SEQ ID NO: 79 | 2.14E+05 | 2.27E-03 | 1.06E-08 |
| SEQ ID NO: 60 | 1.18E+05 | 1.98E-03 | 1.68E-08 |
| SEQ ID NO: 83 | 2.73E+05 | 1.94E-03 | 7.12E-09 |
| SEQ ID NO: 70 | 3.24E+05 | 1.97E-03 | 6.08E-09 |
| SEQ ID NO: 74 | 3.02E+05 | 1.57E-03 | 5.18E-09 |
| SEQ ID NO: 69 | 2.37E+05 | 2.20E-03 | 9.27E-09 |
| SEQ ID NO: 68 | 2.33E+05 | 2.20E-03 | 9.41E-09 |
| SEQ ID NO: 63 | 2.57E+05 | 2.00E-03 | 7.80E-09 |
| SEQ ID NO: 89 | 1.73E+05 | 3.13E-03 | 1.81E-08 |
| SEQ ID NO: 82 | 2.47E+05 | 2.26E-03 | 9.15E-09 |
| SEQ ID NO: 91 | 1.00E+05 | 3.60E-03 | 3.59E-08 |
| SEQ ID NO: 72 | 2.23E+05 | 2.63E-03 | 1.18E-08 |
| SEQ ID NO: 66 | 9.70E+04 | 2.18E-03 | 2.25E-08 |
| SEQ ID NO: 86 | 1.13E+05 | 3.21E-03 | 2.85E-08 |

TABLE 4-continued

| affinity of affinity matured variants and parental antibodies. | | | |
|---|---|---|---|
| IgG | $k_{on}$ (1/Ms) | $k_{off}$ (1/s) | $K_d$ (M) |
| SEQ ID NO: 61 | 6.58E+04 | 1.68E−03 | 2.56E−08 |
| SEQ ID NO: 78 | 1.28E+05 | 1.96E−03 | 1.53E−08 |
| SEQ ID NO: 81 | 1.87E+05 | 2.61E−03 | 1.40E−08 |
| SEQ ID NO: 90 | 1.05E+05 | 2.91E−03 | 2.77E−08 |
| SEQ ID NO: 57 | 9.07E+04 | 2.86E−03 | 3.15E−08 |
| SEQ ID NO: 87 | 1.49E+05 | 2.31E−03 | 1.55E−08 |
| SEQ ID NO: 12 | 1.17E+05 | 2.51E−03 | 2.14E−08 |
| SEQ ID NO: 22 | 6.10E+05 | 2.07E−03 | 3.39E−09 |
| SEQ ID NO: 23 | 6.11E+05 | 3.65E−03 | 5.97E−09 |
| SEQ ID NO: 36 | 9.15E+05 | 9.81E−03 | 1.07E−08 |
| SEQ ID NO: 27 | 1.13E+06 | 6.18E−03 | 5.49E−09 |
| SEQ ID NO: 29 | 1.43E+06 | 9.27E−03 | 6.47E−09 |
| SEQ ID NO: 30 | 3.35E+05 | 1.11E−02 | 3.32E−08 |
| SEQ ID NO: 33 | 1.02E+06 | 1.05E−02 | 1.02E−08 |
| SEQ ID NO: 28 | 1.54E+06 | 8.85E−03 | 5.75E−09 |
| SEQ ID NO: 34 | 1.13E+06 | 9.88E−03 | 8.73E−09 |
| SEQ ID NO: 32 | 1.35E+06 | 9.04E−03 | 6.68E−09 |
| SEQ ID NO: 37 | 9.53E+05 | 1.29E−02 | 1.36E−08 |
| SEQ ID NO: 35 | 1.47E+06 | 1.23E−02 | 8.38E−09 |
| SEQ ID NO: 26 | 1.93E+06 | 7.95E−03 | 4.11E−09 |
| SEQ ID NO: 24 | 1.26E+06 | 4.96E−03 | 3.95E−09 |
| SEQ ID NO: 10 | 1.08E+06 | 8.41E−03 | 7.81E−09 |

Reporter Assay of Variants

Affinity matured variants were reformatted to bivalent IgG format as described in Example 2. The obtained antibodies were used in a TGF-βRII luciferase based reporter assay to test the capacity of the antibodies to inhibit ligand induced activation of the receptor.

293F Freestyle cells were transiently transfected with the reporter CAGA$_{12}$ luciferase. The next day, transfected cells were plated and stimulated with 1 ng/ml of hTGF-β1 in the presence/absence of a 6-point, semi-log serial dilution of anti-TGF-βRII antibody. The anti-TGF-βRII antibody was added simultaneously. The starting and highest concentration of the antibody was 10 μg/ml, and the lowest concentration was 0.03 μg/ml. The 293F Freestyle cells, hTGF-β1 and anti-TGF-βRII antibody mixture was incubated for 3 hours in a 37° C., 5% CO2 incubator. Each plate a titration of a negative competition control comprising a heavy chain variable region having SEQ ID NO: 97 and one well which does not contain TGF-β. As a read out, Steady-Glo Luciferase Assay System detection reagent was added and luciferase was measured after a 5 minute incubation on the EnVision. The fold response was calculated as follows:

$$\frac{(\text{sample with } IgG\ X + TGFbeta) - (\text{negative control } IgG + TGFbeta)}{(\text{positive control } IgG + TGFbeta) - (\text{negative control } IgG + TGFbeta)} \times 100$$

Figure 6:
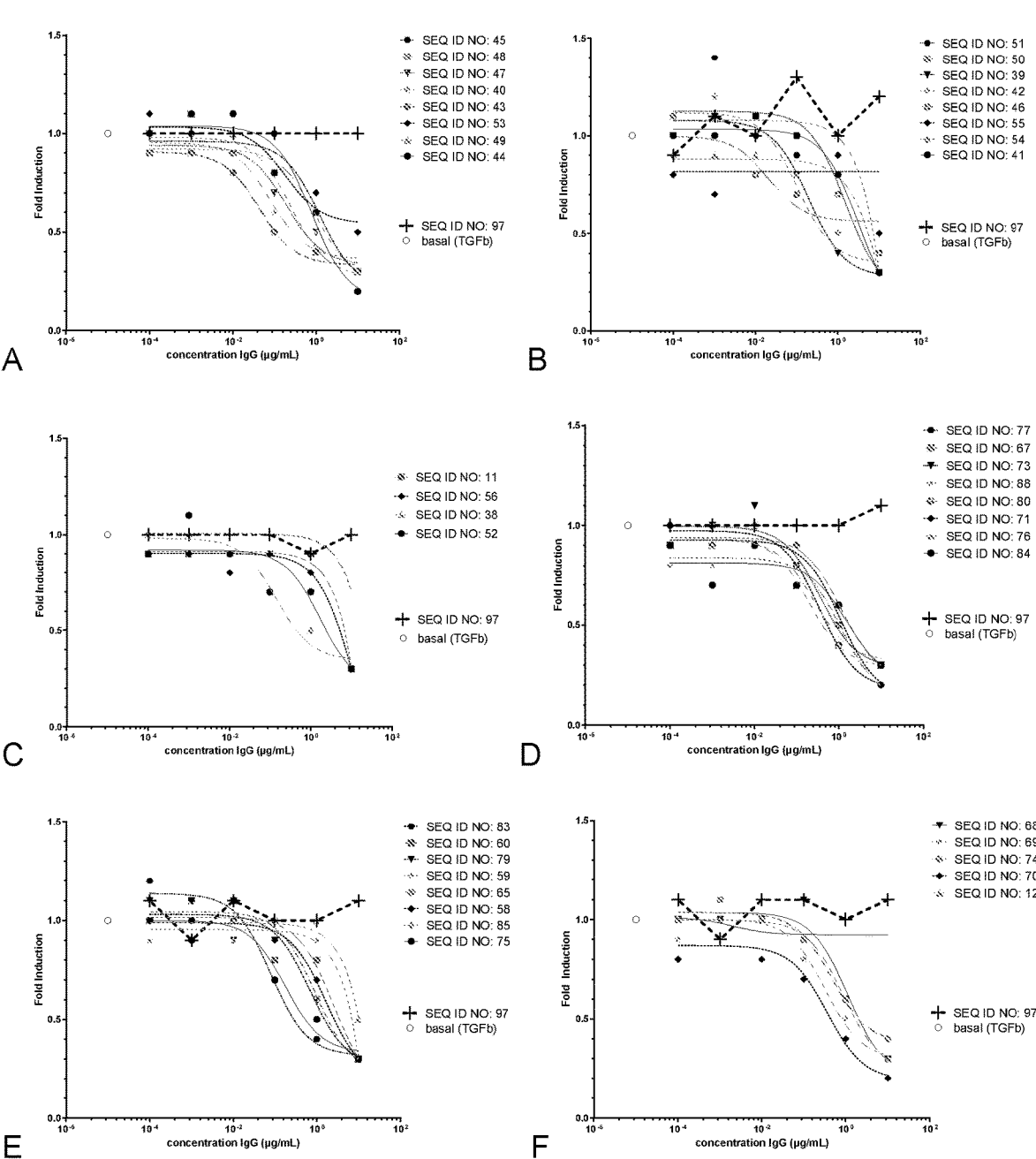
FIG. 6 shows the data from the luciferase reporter assay of the affinity matured variants. The X-axis shows the concentration of antibody in µg/ml. The Y-axis shows the fold induction of the Smad complex as a measure of TGF-β signaling inhibition. Graphs A-K each compare the activity of affinity matured variants with a control antibody (SEQ ID NO: 97). Basal TGF-β is included as a control of TGF-β stimulation of the cells.
Figure 6:
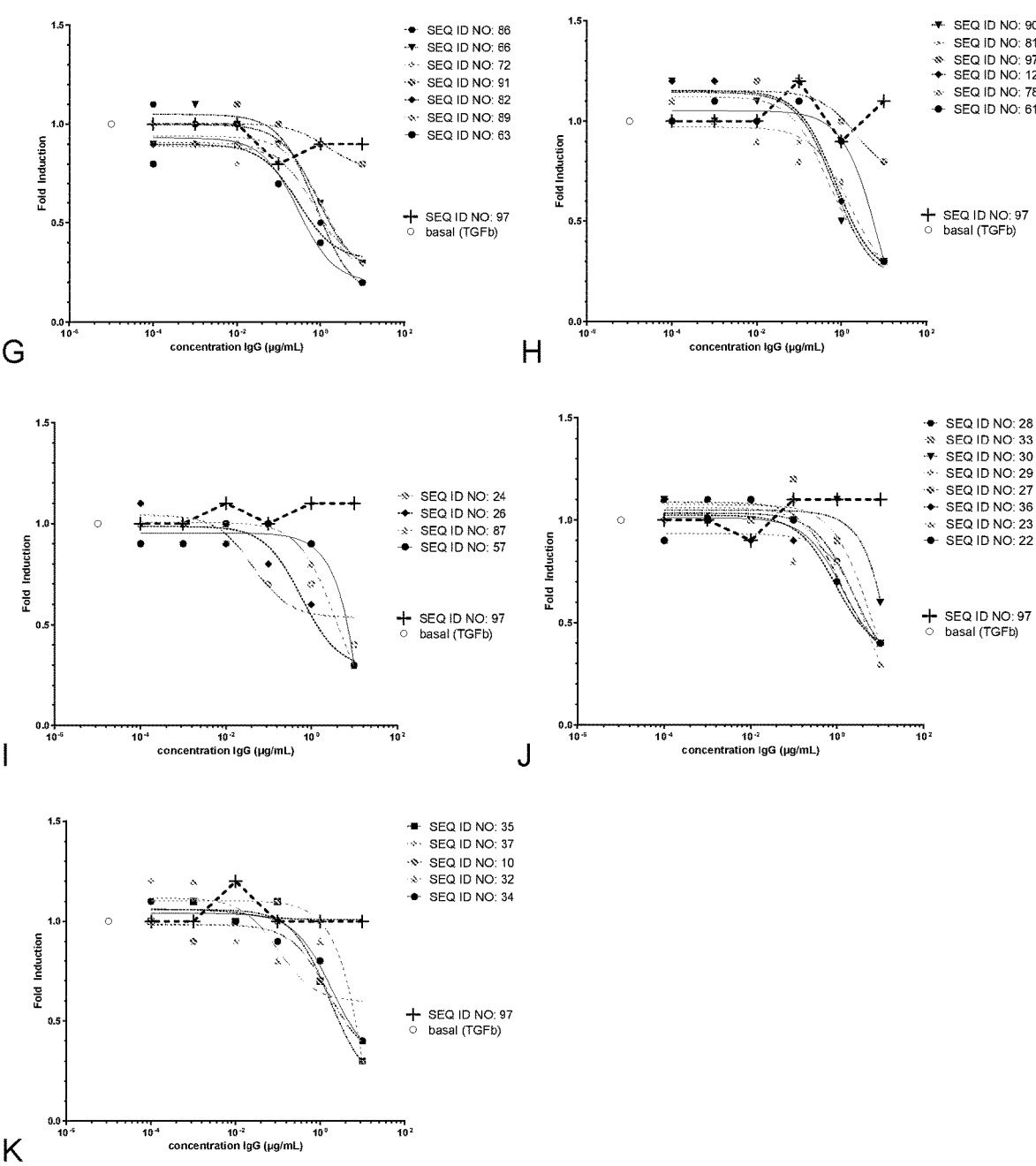

Results are shown in FIG. 6. This data shows that several of the variants exhibit improved ligand blocking activity compared to their parental antibodies. The IC50 values of selected antibodies are presented in Table 5.

TABLE 5

| IC50 values of selected affinity matured variants and parental antibodies. | |
|---|---|
| IgG | IC50 (ug/ml) |
| SEQ ID NO: 10 | 1.53 |
| SEQ ID NO: 12 | 0.86 |

TABLE 5-continued

| IC50 values of selected affinity matured variants and parental antibodies. | |
|---|---|
| IgG | IC50 (ug/ml) |
| SEQ ID NO: 24 | 0.04 |
| SEQ ID NO: 26 | 0.59 |
| SEQ ID NO: 40 | 0.08 |
| SEQ ID NO: 43 | 0.04 |
| SEQ ID NO: 46 | n.a. |
| SEQ ID NO: 47 | 0.19 |
| SEQ ID NO: 48 | 0.25 |
| SEQ ID NO: 54 | 16.40 |
| SEQ ID NO: 67 | 0.25 |
| SEQ ID NO: 70 | 0.36 |
| SEQ ID NO: 75 | 0.18 |
| SEQ ID NO: 76 | 0.20 |
| SEQ ID NO: 77 | 0.36 |
| SEQ ID NO: 78 | 1.50 |
| SEQ ID NO: 83 | 0.08 |
| SEQ ID NO: 84 | 1.54 |
| SEQ ID NO: 88 | 1.16 |

Example 4—Epitope Mapping

Figures 7, 7C, 7D:
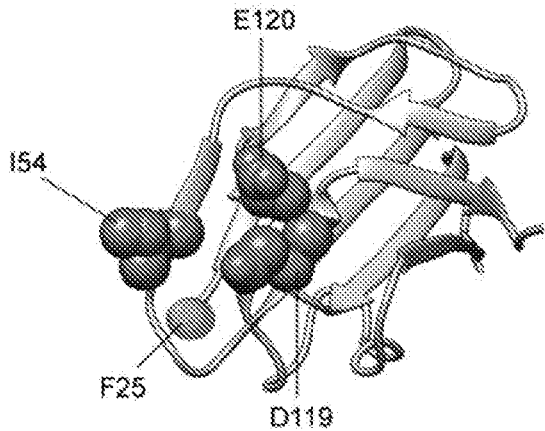
FIG. 7 shows the data from the alanine scan.
FIG. 7C is a table showing the binding reactivity of SEQ ID NO: 10; SEQ ID NO: 12; SEQ ID NO: 93; and SEQ ID NO: 98 (control), as a percentage compared to wildtype. Residues critical for binding are indicated with rectangles.
FIG. 7D shows the mapping of the critical residues on TGFβRII.

To identify the residues of TGF-βRII that are part of the epitope bound by the antibodies generated herein, shotgun mutagenesis experiments were performed using standard techniques (Davidson and Doranz, 2014). As a control in the shotgun mutagenesis approach, an antibody comprising heavy chain variable regions having SEQ ID NO: 98 was used. This antibody was unable to block ligand binding to the receptor and could bind the receptor in the presence of all functional TGF-βRII antibodies. Results are shown in FIG. 7.

Example 5—TGF-βRII Blocking Activity of Antibodies Comprising a TGF-βRII Binding Domain RSVxTGF-βRII and Antigen AxTGF-βRII antibodies were screened in a TGFβ reporter assay.

Bispecific antibodies were produced comprising a first binding domain that binds TGF-βRII comprising a VH region of a selection of antibodies as described herein and a second binding domain that binds RSV comprising a VH region having an amino acid sequence as set forth in SEQ ID NO: 136, or a second binding domain that binds an antigen expressed on the same cell as TGF-βRII (Antigen A). Antigen A is an arbitrarily selected antigen not reactive with TGFβ or impacting the signaling cascade tested in the TGFβ reporter assay. Also included were the positive control antibody and negative control antibodies as described in Example 1.

The TGFβ reporter assay uses a CAGA$_{12}$ luciferase vector containing 12 copies of the CAGA box which are the SMAD3 and SMAD4 binding sequences [Dennler et al, 1998]. Binding of TGFβ to TGF-βRII leads to phosphorylation of TGF-βRI. Phosphorylation of TGF-βRI initiates a signaling cascade that leads to phosphorylation and activation of SMAD2 and SMAD3, which then form a complex with SMAD4. The SMAD complex then translocates to the nucleus and binds to the SMAD binding element (SBE) in the nucleus, leading to transcription and expression of TGFβ/SMAD responsive genes. The CAGA$_{12}$ luciferase reporter can be used to monitor activation by TGFβ and to screen TGF-βRII blocking antibodies after transfecting the reporter in mammalian cells.

Cryopreserved 293FF cells stably transfected to express Antigen A were transiently transfected with the TGFβ reporter. IgGs were tested at a final concentration of 10 μg/ml to 100 μg/ml. IgGs were added in a final volume of 25 μl (4× concentrated). Subsequently, 25 μl of hTGFβ1 (4× concentrated) was added with a final concentration of 1 ng/ml. 50 μL transfected cell suspension ($5 \times 10^4$ cells) was added. 100 μL Steady-Glo™ substrate was added to each well and allowed to incubate for 5 minutes. Luminescence was measured on EnVision and results analyzed using Graphpad Prism.

Figure 8:
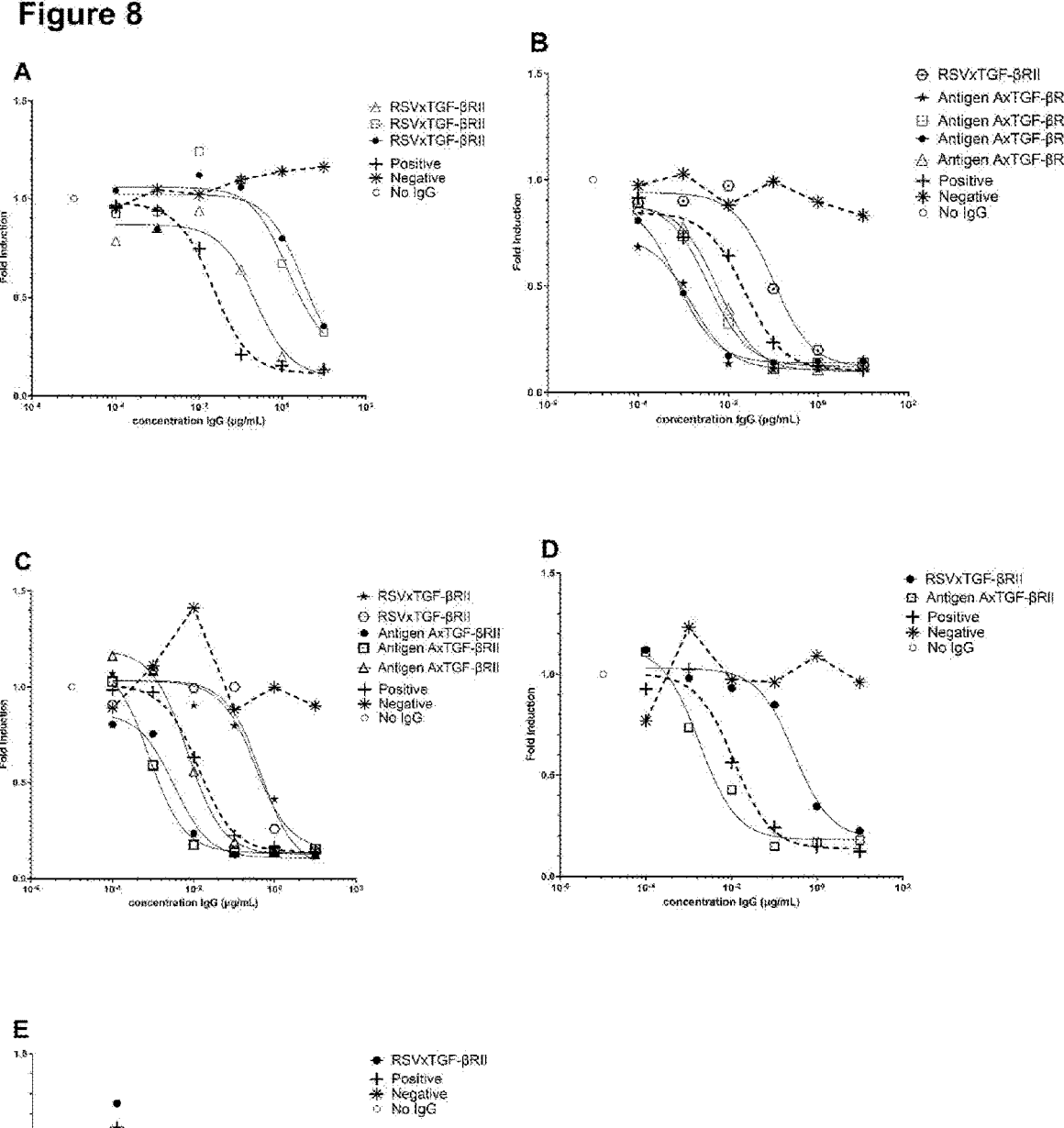
FIG. 8 shows the results from screening a variety of bispecific antibodies comprising a TGF-βRII binding domain of the invention in a TGF-β reporter assay. The X-axis shows the concentration of antibody in µg/ml. The Y-axis shows the fold induction of Smad signaling. Graphs A-E each compare the activity of the bispecific antibodies comprising a single TGF-βRII binding domain with the positive control antibody known to block ligand binding to TGF-βRII (+) as described in Example 1. Basal TGF-β is included as a control of TGF-β stimulation of the cells.

Results are shown in FIG. 8. The bispecific antibodies comprising a monovalent binding domain for TGF-βRII and a control binding domain against RSV, as well as the bispecific antibodies comprising a monovalent binding domain for TGF-βRII and Antigen A, block the interaction of TGF-β with TGF-βRII. The bispecific antibody targeting TGF-βRII and RSV, which include the TGF-βRII binding domains comprising a VH region having an amino acid sequence as set out in SEQ ID NO: 76 and 70 are nearly as potent as the bivalent monospecific positive control antibody. Bispecific antibodies targeting TGF-βRII and Antigen A, which include the TGF-βRII binding domain comprising a VH region having an amino acid sequence as set out in SEQ ID NO: 70, 61, 86, 65, 12, and 76, are more potent than the bivalent monospecific positive control antibody. Accordingly, anti-TGF-βRII binding domains of the present disclosure demonstrate comparable, equal and superior TGF-βRII blocking capability in monovalent form, providing for a variety of applications as monovalent molecules, bivalent molecules, or as a one or more valencenes as incorporated into a multispecific molecule.

Sequencing of the Heavy Chain Variable Regions

The nucleic acids encoding VH regions of a selection of antibodies that were identified to bind human TGF-βRII and block interaction with its ligand were sequenced. Sequence information is provided below.

---

SEQUENCES

SEQ ID NO: 1: HCDR1 according to Kabat
IYAMT

SEQ ID NO: 2: HCDR2 according to Kabat
VISGSGGTTYYADSVKG

SEQ ID NO: 3: HCDR3 according to Kabat
RGQYRDIVGATDY

SEQ ID NO: 4: HCDR1 according to Kabat
NAWMS

SEQ ID NO: 5: HCDR2 according to Kabat
RIKTTISGGATDFAAPVKG

SEQ ID NO: 6: HCDR3 according to Kabat
DLRDY

SEQ ID NO: 7: HCDR1 according to Kabat
RYAMS

SEQ ID NO: 8: HCDR2 according to Kabat
AISASGDRTHNTDSVKG

SEQ ID NO: 9: HCDR3 according to Kabat
GIAASGKNYFDP

SEQ ID NO: 10: Heavy chain variable region
EVQLVESGGGLVQPGGSLRLSCAASGFTFDIYAMTWVRQAPGKGLEWV
SVISGSGGTTYYADSVKGRFTISRDNSKNTLYLQMNSLRAEDTAVYYCA
RRGQYRDIVGATDYWGQGTLVTVSS SEQ ID NO: 11: Heavy chain variable region
QVQLVESGGGLVEPGGSLRLSCAASGFTFSNAWMSWVRQAPGKGLEW
VGRIKTTISGGATDFAAPVKGRFTISRDDSKNTLYLQMNSLKTEDTAVY
YCTLDLRDYWGQGTLVTVSS SEQ ID NO: 12: Heavy chain variable region
QVQLVESGGGLVQPGGSLRLSCAVSGFTFRRYAMSWVRQAPGKGLEW
VSAISASGDRTHNTDSVKGRFSISRDNSKNTLYLQMNSLRAEDTAVYFC
AKGIAASGKNYFDPWGQGTLVTVSS SEQ ID NO: 13: LCDR1 according to IMGT
QSISSY SEQ ID NO: 14: LCDR2 according to IMGT
AAS SEQ ID NO: 15: LCDR3 according to IMGT
QQSYSTPPT SEQ ID NO: 16: Light chain variable region
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPTFGQG
TKVEIK -continued

| SEQUENCES |
| --- |

SEQ ID NO: 17: Heavy chain constant region
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTV
DKSRWQQGNVFSCSVMHEALHNHYTQKSLSLSPG SEQ ID NO: 18: Light chain constant region
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC SEQ ID NO: 19: LCDR1 according to Kabat
RASQSISSYLN SEQ ID NO: 20: LCDR2 according to Kabat
AASSLQS SEQ ID NO: 21: LCDR3 according to Kabat
QQSYSTPPT SEQ ID NO: 22: Heavy chain variable region
EVQLVESGGGLVQPGGSLRLSCAASGFTFDINAMTWVRQAPGKGLEWV
SVISGSGGTTYYADSVKGRFTISRDNSKNTLYLQMNSLRAEDTAVYYCA
RRGQYRDIVGATDYWGQGTLVTVSS SEQ ID NO: 23: Heavy chain variable region
EVQLVESGGGLVQPGGSLRLSCAASGFTFDIQAMTWVRQAPGKGLEWV
SVISGSGGTTYYADSVQGRFTISRDNSKNTLYLQMNSLRAEDTAVYYCA
RRGQYRDIVGATDYWGQGTLVTVSS SEQ ID NO: 24: Heavy chain variable region
EVQLVESGGGLVQPGGSLRLSCAASGFTFDIYRMTWVRQAPGKGLEWV
SVISGSGGTTYYADSVKGRFTISRDNSKNTLYLQMNSLRAEDTAVYYCA
RQGQYREIVGATDYWGQGTLVTVSS SEQ ID NO: 25: Heavy chain variable region
EVQLVESGGGLVQPGGSLRLSCAASGFYFDIYAMTWVRQAPGKGLEWV
SVISGSGGTTYYADSVKGRFTISRDNSKNTLYLQMNSLRAEDTAVYYCA
RRSQYRDKVGATDYWGQGTLVTVSS SEQ ID NO: 26: Heavy chain variable region
EVQLVESGGGLVQPGGSLRLSCAASGFTFDINAMTWVRQAPGKGLEW
VSVISGSGGTTYYADSVKGRFTISRDNSKNTLYLQMNSLRAEDTAVYY
CARRGQYREIAGATDYWGQGTLVTVSS SEQ ID NO: 27: Heavy chain variable region
EVQLVESGGGLVQPGGSLRLSCAASGFAFDIYAMTWVRQAPGKGLEWV
SVISGSGGTIYYADSVKGRFTISRDNSKNTLYLQMNSLRAEDTAVYYCA
RRGQYRDIVGATDYWGQGTLVTVSS SEQ ID NO: 28: Heavy chain variable region
EVQLVESGGGLVQPGGSLRLSCAASGFTFDIYAMTWVRQAPGKGLEWV
SVISGSGGTVYYADSVKGRFTISRDNSKNTLYLQMNSLRAEDTAVYYCA
RRGQYRDIAGGTDYWGQGTLVTVSS SEQ ID NO: 29: Heavy chain variable region
EVQLVESGGGLVQPGGSLRLSCAASGFDFDIYAMTWVRQAPGKGLEWV
SVISGSGGTTYYADSVKGRFTISRDNSKNTLYLQMNSLRAEDTAVYYCA
RRSQYRDKVGATDYWGQGTLVTVSS SEQ ID NO: 30: Heavy chain variable region
EVQLVESGGGLVQPGGSLRLSCAASGFRFDIYAMTWVRQAPGKGLEW
VSVISGSGGTTYYADSVKGRFTISRDNSKNTLYLQMNSLRAEDTAVYY
CARRGQYRRIVGATDYWGQGTLVTVSS SEQ ID NO: 31: Heavy chain variable region
EVQLVESGGGLVQPGGSLRLSCAASGFTFDINAMTWVRQAPGKGLEWV
SVISGSGGTTAYADSVKGRFTISRDNSKNTLYLQMNSLRAEDTAVYYCA
RRGQYRYIAGATDYWGQGTLVTVSS -continued

SEQUENCES

SEQ ID NO: 32: Heavy chain variable region
EVQLVESGGGLVQPGGSLRLSCAASGFTFDITAMTWVRQAPGKGLEWV
SVISGSGGTTYYADSVKGRFTISRDNSKNTLYLQMNSLRAEDTAVYYCA
RRGQYRDIAGATDYWGQGTLVTVSS SEQ ID NO: 33: Heavy chain variable region
EVQLVESGGGLVQPGGSLRLSCAASGFSFDIYAMTWVRQAPGKGLEWV
SVISGSGGTTYYADSVKGRFTISRDNSKNTLYLQMNSLRAEDTAVYYCA
RRAQYRDKVGATDYWGQGTLVTVSS SEQ ID NO: 34: Heavy chain variable region
EVQLVESGGGLVQPGGSLRLSCAASGFTFDIYAMTWVRQAPGKGLEWV
SVISGSGGTTYYADSVKGRFTISRDNSKNTLYLQMNSLRAEDTAVYYCA
RRGQYRYVVGATDYWGQGTLVTVSS SEQ ID NO: 35: Heavy chain variable region
EVQLVESGGGLVQPGGSLRLSCAASGFYFDIYAMTWVRQAPGKGLEWV
SVISGSGGTTYYADSVKGRFTISRDNSKNTLYLQMNSLRAEDTAVYYCA
RRGQYRHIAGATDYWGQGTLVTVSS SEQ ID NO: 36: Heavy chain variable region
EVQLVESGGGLVQPGGSLRLSCAASGFRFDIYAMTWVRQAPGKGLEWV
SVISGSGGTTYYADSVKGRFTISRDNSKNTLYLQMNSLRAEDTAVYYCA
RRGQYRDIVGATDYWGQGTLVTVSS SEQ ID NO: 37: Heavy chain variable region
EVQLVESGGGLVQPGGSLRLSCAASGFTFDINAMTWVRQAPGKGLEWV
SVISGSGATTYYADSVKGRFTISRDNSKNTLYLQMNSLRAEDTAVYYCA
RRGQYREIQGANDYWGQGTLVTVSS SEQ ID NO: 38: Heavy chain variable region
QVQLVESGGGLVEPGGSLRLSCAASGFTFSRAWMSWVRQAPGKGLEW
VGRIKTTISGGATQFAAPVKGRFTISRDDSKNTLYLQMNSLKTEDTAVY
YCTLDLRNYWGQGTLVTVSS SEQ ID NO: 39: Heavy chain variable region
QVQLVESGGGLVEPGGSLRLSCAASGFTFSRAWMSWVRQAPGKGLEW
VGRIKTTVSGGATAFAAPVKGRFTISRDDSKNTLYLQMNSLKTEDTAVY
YCTLDLRAYWGQGTLVTVSS SEQ ID NO: 40: Heavy chain variable region
QVQLVESGGGLVEPGGSLRLSCAASGFTFSNYWMSWVRQAPGKGLEW
VGRIKTTYSGGATDFAAPVKGRFTISRDDSKNTLYLQMNSLKTEDTAV
YYCTLDLRDYWGQGTLVTVSS SEQ ID NO: 41: Heavy chain variable region
QVQLVESGGGLVEPGGSLRLSCAASGFTFSRAWMSWVRQAPGKGLEW
VGRIKTTYSGGATDFAAPVKGRFTISRDDSKNTLYLQMNSLKTEDTAVY
YCTLDLRKYWGQGTLVTVSS SEQ ID NO: 42: Heavy chain variable region
QVQLVESGGGLVEPGGSLRLSCAASGFTFSRAWMSWVRQAPGKGLEW
VGRIKTTISGGATDFAAPVKGRFTISRDDSKNTLYLQMNSLKTEDTAVY
YCTLDLRAYWGQGTLVTVSS SEQ ID NO: 43: Heavy chain variable region
QVQLVESGGGLVEPGGSLRLSCAASGFKFSNAWMSWVRQAPGKGLEW
VGRIKTTISGGATQFAAPVKGRFTISRDDSKNTLYLQMNSLKTEDTAVY
YCTLDLRDYWGQGTLVTVSS SEQ ID NO: 44: Heavy chain variable region
QVQLVESGGGLVEPGGSLRLSCAASGFTFSNAWMSWVRQAPGKGLEW
VGRIKTTYSGGATDFAAPVKGRFTISRDDSKNTLYLQMNSLKTEDTAVY
YCTLDLRDYWGQGTLVTVSS SEQ ID NO: 45: Heavy chain variable region
QVQLVESGGGLVEPGGSLRLSCAASGFTFSNAWMSWVRQAPGKGLEW
VGRIKTTYSGGATEFAAPVKGRFTISRDDSKNTLYLQMNSLKTEDTAVY
YCTLDLRKYWGQGTLVTVSS SEQ ID NO: 46: Heavy chain variable region
QVQLVESGGGLVEPGGSLRLSCAASGFTFSNYWMSWVRQAPGKGLEW
VGRIKTTISGGATDFAAPVKGRFTISRDDSKNTLYLQMNSLKTEDTAVY
YCTLDLRAYWGQGTLVTVSS -continued

| SEQUENCES |
| --- |

SEQ ID NO: 47: Heavy chain variable region
QVQLVESGGGLVEPGGSLRLSCAASGFTFSRAWMSWVRQAPGKGLEW
VGRIKTTISGAATDFAAPVKGRFTISRDDSKNTLYLQMNSLKTEDTAVY
YCTLDLRDYWGQGTLVTVSS SEQ ID NO: 48: Heavy chain variable region
QVQLVESGGGLVEPGGSLRLSCAASGFTFANAWMSWVRQAPGKGLEW
VGRIKTTYSGGATDFAAPVKGRFTISRDDSKNTLYLQMNSLKTEDTAVY
YCTLDLRKYWGQGTLVTVSS SEQ ID NO: 49: Heavy chain variable region
QVQLVESGGGLVEPGGSLRLSCAASGFQFSNAWMSWVRQAPGKGLEW
VGRIKTTYSGGATDFAAPVKGRFTISRDDSKNTLYLQMNSLKTEDTAVY
YCTLDLRDYWGQGTLVTVSS SEQ ID NO: 50: Heavy chain variable region
QVQLVESGGGLVEPGGSLRLSCAASGFTFSNAHMSWVRQAPGKGLEW
VGRIKTTYSGGATDFAAPVKGRFTISRDDSKNTLYLQMNSLKTEDTAVY
YCTLDLRQYWGQGTLVTVSS SEQ ID NO: 51: Heavy chain variable region
QVQLVESGGGLVEPGGSLRLSCAASGFTFANAWMSWVRQAPGKGLEW
VGRIKTTYSGGATEFAAPVKGRFTISRDDSKNTLYLQMNSLKTEDTAVY
YCTLDLRTYWGQGTLVTVSS SEQ ID NO: 52: Heavy chain variable region
QVQLVESGGGLVEPGGSLRLSCAASGFTFSNAWMSWVRQAPGKGLEW
VGRIKTTYSGGATDFAAPVKGRFTISRDDSKNTLYLQMNSLKTEDTAVY
YCTLDLRSYWGQGTLVTVSS SEQ ID NO: 53: Heavy chain variable region
QVQLVESGGGLVEPGGSLRLSCAASGFQFSNAWMSWVRQAPGKGLEW
VGRIKTTISGGATEFAAPVKGRFTISRDDSKNTLYLQMNSLKTEDTAVY
YCTLDLRDYWGQGTLVTVSS SEQ ID NO: 54: Heavy chain variable region
QVQLVESGGGLVEPGGSLRLSCAASGFVFSNAWMSWVRQAPGKGLEW
VGRIKTTFSGGATDFAAPVKGRFTISRDDSKNTLYLQMNSLKTEDTAVY
YCTLDLRKYWGQGTLVTVSS SEQ ID NO: 55: Heavy chain variable region
QVQLVESGGGLVEPGGSLRLSCAASGFHFSNAWMSWVRQAPGKGLEW
VGRIKTTISGGATDFAAPVKGRFTISRDDSKNTLYLQMNSLKTEDTAVY
YCTLDLRAYWGQGTLVTVSS SEQ ID NO: 56: Heavy chain variable region
QVQLVESGGGLVEPGGSLRLSCAASGFKFSNAWMSWVRQAPGKGLEW
VGRIKTTISGGKTEFAAPVKGRFTISRDDSKNTLYLQMNSLKTEDTAVY
YCTLDLRRYWGQGTLVTVSS SEQ ID NO: 57: Heavy chain variable region
QVQLVESGGGLVQPGGSLRLSCAVSGFAFRRYAMSWVRQAPGKGLEW
VSAISASGDRTHNTDSVKGRFSISRDNSKNTLYLQMNSLRAEDTAVYFC
AKGIAKRGKNYFDPWGQGTLVTVSS SEQ ID NO: 58: Heavy chain variable region
QVQLVESGGGLVQPGGSLRLSCAVSGFQFRRYAMSWVRQAPGKGLEW
VSAISASGDRTHNTDSVKGRFSISRDNSKNTLYLQMNSLRAEDTAVYFC
AKGIAKSGKNYFDPWGQGTLVTVSS SEQ ID NO: 59: Heavy chain variable region
QVQLVESGGGLVQPGGSLRLSCAVSGFTFRRYAMSWVRQAPGKGLEW
VSAISASGDRTHNTDSVKGRFSISRDNSKNTLYLQMNSLRAEDTAVYFC
AKGIAKSGKNYFDPWGQGTLVTVSS SEQ ID NO: 60: Heavy chain variable region
QVQLVESGGGLVQPGGSLRLSCAVSGFKFRRYAMSWVRQAPGKGLEW
VSSISASGDRTHNTDSVKGRFSISRDNSKNTLYLQMNSLRAEDTAVYFC
AKGLAASGKNYFDPWGQGTLVTVSS SEQ ID NO: 61: Heavy chain variable region
QVQLVESGGGLVQPGGSLRLSCAVSGFRFRRYAMSWVRQAPGKGLEW
VSAISASGDRTHNTDSVKGRFSISRDNSKNTLYLQMNSLRAEDTAVYFC
AKGIYASGKHYFDPWGQGTLVTVSS -continued

| SEQUENCES |
|---|

SEQ ID NO: 62: Heavy chain variable region
QVQLVESGGGLVQPGGSLRLSCAVSGFTFRRYAMSWVRQAPGKGLEW
VSAISASGDRTKNTDSVKGRFSISRDNSKNTLYLQMNSLRAEDTAVYFC
AKGTAASGRNYFDPWGQGTLVTVSS SEQ ID NO: 63: Heavy chain variable region
QVQLVESGGGLVQPGGSLRLSCAVSGFAFRRYAMSWVRQAPGKGLEW
VSSISASGDRTKNTDSVKGRFSISRDNSKNTLYLQMNSLRAEDTAVYFC
AKGIAASGKNYFDPWGQGTLVTVSS SEQ ID NO: 64: Heavy chain variable region
QVQLVESGGGLVQPGGSLRLSCAVSGFTFRRYAMSWVRQAPGKGLEW
VSAISASGDRTHNTDSVKGRFSISRDNSKNTLYLQMNSLRAEDTAVYFC
AKGIFASGKHYFDPWGQGTLVTVSS SEQ ID NO: 65: Heavy chain variable region
QVQLVESGGGLVQPGGSLRLSCAVSGFTFGRYAMSWVRQAPGKGLEW
VSAISASGDRHHNTDSVKGRFSISRDNSKNTLYLQMNSLRAEDTAVYF
CAK<u>GIAKSGKNYFDP</u>WGQGTLVTVSS SEQ ID NO: 66: Heavy chain variable region
QVQLVESGGGLVQPGGSLRLSCAVSGFQFRRYAMSWVRQAPGKGLEW
VSDISASGDRTHNTDSVKGRFSISRDNSKNTLYLQMNSLRAEDTAVYFC
AKGIARSGKNYFDPWGQGTLVTVSS SEQ ID NO: 67: Heavy chain variable region
QVQLVESGGGLVQPGGSLRLSCAVSGFTFRRYAMSWVRQAPGKGLEW
VSAISASGDRTLNTDSVKGRFSISRDNSKNTLYLQMNSLRAEDTAVYFC
AKGTAARGKNYFDPWGQGTLVTVSS SEQ ID NO: 68: Heavy chain variable region
QVQLVESGGGLVQPGGSLRLSCAVSGFAFRRYAMSWVRQAPGKGLEW
VSAISAFGDRTHNTDSVKGRFSISRDNSKNTLYLQMNSLRAEDTAVYFC
AKGTAASGKNFFDPWGQGTLVTVSS SEQ ID NO: 69: Heavy chain variable region
QVQLVESGGGLVQPGGSLRLSCAVSGFTFRRYAMSWVRQAPGKGLEW
VSAISASGDRTKNTDSVKGRFSISRDNSKNTLYLQMNSLRAEDTAVYFC
AKGTAASGKNFFDPWGQGTLVTVSS SEQ ID NO: 70: Heavy chain variable region
QVQLVESGGGLVQPGGSLRLSCAVSGFTFSRYAMSWVRQAPGKGLEW
VSAISASGDRTKNTDSVKGRFSISRDNSKNTLYLQMNSLRAEDTAVYFC
AK<u>GTAAAGKNYFDP</u>WGQGTLVTVSS SEQ ID NO: 71: Heavy chain variable region
QVQLVESGGGLVQPGGSLRLSCAVSGFQFRRYAMSWVRQAPGKGLEW
VSAISAHGDRTHNTDSVKGRFSISRDNSKNTLYLQMNSLRAEDTAVYFC
AKGTAASGKNYFDPWGQGTLVTVSS SEQ ID NO: 72: Heavy chain variable region
QVQLVESGGGLVQPGGSLRLSCAVSGFTIRRYAMSWVRQAPGKGLEWV
SYISASGDRTHNTDSVKGRFSISRDNSKNTLYLQMNSLRAEDTAVYFCA
KGTANSGKNYFDPWGQGTLVTVSS SEQ ID NO: 73: Heavy chain variable region
QVQLVESGGGLVQPGGSLRLSCAVSGFTFRRYAMSWVRQAPGKGLEW
VSAISASGDRTHNTDSVKGRFSISRDNSKNTLYLQMNSLRAEDTAVYFC
AKGTAARGKNYFDPWGQGTLVTVSS SEQ ID NO: 74: Heavy chain variable region
QVQLVESGGGLVQPGGSLRLSCAVSGFTFERYAMSWVRQAPGKGLEW
VSAISASGDRTQNTDSVKGRFSISRDNSKNTLYLQMNSLRAEDTAVYFC
AKGTAASGRNYFDPWGQGTLVTVSS SEQ ID NO: 75: Heavy chain variable region
QVQLVESGGGLVQPGGSLRLSCAVSGFEFRRYAMSWVRQAPGKGLEW
VSAISAGGDRTANTDSVKGRFSISRDNSKNTLYLQMNSLRAEDTAVYFC
AKGTAARGKNYFDPWGQGTLVTVSS SEQ ID NO: 76: Heavy chain variable region
QVQLVESGGGLVQPGGSLRLSCAVSGFAFRRYAMSWVRQAPGKGLEW
VSAISASGDRTQNTDSVKGRFSISRDNSKNTLYLQMNSLRAEDTAVYFC
AK<u>GTAASGKNYFDP</u>WGQGTLVTVSS -continued

| SEQUENCES |
|---|

SEQ ID NO: 77: Heavy chain variable region
QVQLVESGGGLVQPGGSLRLSCAVSGFSFRRYAMSWVRQAPGKGLEW
VSAISASGDRTLNTDSVKGRFSISRDNSKNTLYLQMNSLRAEDTAVYFC
AKGTAARGKNYFDPWGQGTLVTVSS SEQ ID NO: 78: Heavy chain variable region
QVQLVESGGGLVQPGGSLRLSCAVSGFEFRRYAMSWVRQAPGKGLEW
VSAISASGDRTDNTDSVKGRFSISRDNSKNTLYLQMNSLRAEDTAVYFC
AKGIARSGKNFFDPWGQGTLVTVSS SEQ ID NO: 79: Heavy chain variable region
QVQLVESGGGLVQPGGSLRLSCAVSGFNFRRYAMSWVRQAPGKGLEW
VSAISASGDRTHNTDSVTGRFSISRDNSKNTLYLQMNSLRAEDTAVYFC
AKGLAASGKNYFDPWGQGTLVTVSS SEQ ID NO: 80: Heavy chain variable region
QVQLVESGGGLVQPGGSLRLSCAVSGFAFRRYAMSWVRQAPGKGLEW
VSAISAHGDRTHNTDSVKGRFSISRDNSKNTLYLQMNSLRAEDTAVYFC
AKGTAASGKNYFDPWGQGTLVTVSS SEQ ID NO: 81: Heavy chain variable region
QVQLVESGGGLVQPGGSLRLSCAVSGFTFRRYAMSWVRQAPGKGLEW
VSAISASGDRTHNTDSVKGRFSISRDNSKNTLYLQMNSLRAEDTAVYFC
AKGLAASGKNFFDPWGQGTLVTVSS SEQ ID NO: 82 Heavy chain variable region
QVQLVESGGGLVQPGGSLRLSCAVSGFAFRRYAMSWVRQAPGKGLEW
VSSISASGDRTHNTDSVKGRFSISRDNSKNTLYLQMNSLRAEDTAVYFC
AKGLASSGKNYFDPWGQGTLVTVSS SEQ ID NO: 83: Heavy chain variable region
QVQLVESGGGLVQPGGSLRLSCAVSGFQFRRYAMSWVRQAPGKGLEW
VSSISASGDRTHNTDSVKGRFSISRDNSKNTLYLQMNSLRAEDTAVYFC
AKGLAASGKNYFDPWGQGTLVTVSS SEQ ID NO: 84: Heavy chain variable region
QVQLVESGGGLVQPGGSLRLSCAVSGFQFRRYAMSWVRQAPGKGLEW
VSAISASGDRYHNTDSVKGRFSISRDNSKNTLYLQMNSLRAEDTAVYFC
AKGTAASGKNYFDPWGQGTLVTVSS SEQ ID NO: 85: Heavy chain variable region
QVQLVESGGGLVQPGGSLRLSCAVSGFKFRRYAMSWVRQAPGKGLEW
VSAISASGDYTHNTDSVKGRFSISRDNSKNTLYLQMNSLRAEDTAVYFC
AKGIAKSGKNYFDPWGQGTLVTVSS SEQ ID NO: 86: Heavy chain variable region
QVQLVESGGGLVQPGGSLRLSCAVSGFAFRRYAMSWVRQAPGKGLEW
VSAISASGDRTRNTDSVKGRFSISRDNSKNTLYLQMNSLRAEDTAVYFC
AKGIATSGKNYFDPWGQGTLVTVSS SEQ ID NO: 87: Heavy chain variable region
QVQLVESGGGLVQPGGSLRLSCAVSGFTFKRYAMSWVRQAPGKGLEW
VSAISASGDRSHNTDSVKGRFSISRDNSKNTLYLQMNSLRAEDTAVYFC
AKGLAARGKNYFDPWGQGTLVTVSS SEQ ID NO: 88: Heavy chain variable region
QVQLVESGGGLVQPGGSLRLSCAVSGFNFRRYAMSWVRQAPGKGLEW
VSAISASGDRTHNTDSVKGRFSISRDNSKNTLYLQMNSLRAEDTAVYFC
AKGTAARGKNYFDPWGQGTLVTVSS SEQ ID NO: 89: Heavy chain variable region
QVQLVESGGGLVQPGGSLRLSCAVSGFTFRRYAMSWVRQAPGKGLEW
VSAISASGDRTHNTDSVKGRFSISRDNSKNTLYLQMNSLRAEDTAVYFC
AKGIAASGKNFFDPWGQGTLVTVSS SEQ ID NO: 90: Heavy chain variable region
QVQLVESGGGLVQPGGSLRLSCAVSGFTFRRYAMSWVRQAPGKGLEW
VSAISASGDRTHNTDSVKGRFSISRDNSKNTLYLQMNSLRAEDTAVYFC
AKGIAARGKNYFDPWGQGTLVTVSS SEQ ID NO: 91: Heavy chain variable region
QVQLVESGGGLVQPGGSLRLSCAVSGFRFRRYAMSWVRQAPGKGLEW
VSAISASGDRTHNTDSVKGRFSISRDNSKNTLYLQMNSLRAEDTAVYFC
AKGIAARGKNFFDPWGQGTLVTVSS -continued

| SEQUENCES |
| --- |

SEQ ID NO: 92: Heavy chain variable region
EVQLVETGAEVKKPGASVKVSCKASDYIFTKYDINWVRQAPGQGLEW
MGWMSANTGNTGYAQKFQGRVTMTRDTSINTAYMELSSLTSGDTAVY
FCARSSLFKTETAPYYHFALDVWGQGTTVTSS SEQ ID NO: 93: Heavy chain variable region
EVQLVESGGDLVKPGGSLRLSCAASGFTFSNAWMSWVRQAPGKGLEW
VGRVKTTVSGGTTDYAAAVKGRFTISRDDSKNTLYLQMNSLKTEDTAI
YYCTIDLRDYWGQGTLVTVSS SEQ ID NO: 94: Heavy chain variable region
EVQLVESGGGLVQPGGSLRLSCAASGFTFSRYAMSWVRQAPGKGLEWV
SSINTSGGNTFYADSVKGRFTISRDNSKNTLYLQMNSLRAEDTAIYYCAK
GIAATGKNYFDPWGQGTLVTVSS SEQ ID NO: 95: Heavy chain variable region
QVQLVESGGGLVQPGGSLRLSCAASGFTFSRYAMSWVRQAPGKGLEW
VSSINTSGGNTFYADSVKGRFTISRDNSKNTLYLQMNSLRAEDTAVYYC
VKGIAAAGKNWFGPWGQGTLVTVSS SEQ ID NO: 96: Heavy chain variable region
QVQLVESGGGLVQPGGSLSLSCAASGFTFSRYAMSWVRQAPGKGLEWV
SSINTSGGNTYYADSVKGRFTISRDNSKNTLYLQMNSLRAEDTAVYYCA
KGIAASGKNYFDPWGQGTLVTVSS SEQ ID NO: 97: Heavy chain variable region
EVQLVESGGGVVQPGRSLRLSCAASGFTFSNYGMHWVRQAPGKGLEW
VAVISYDGSTKYSADSLKGRFTISRDNSKNTLYLQMNSLRADDTAVYYC
AKEGWSFDSSGYRSWFDSWGQGTLVTVSS SEQ ID NO: 98: Heavy chain variable region
QLQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCARS
FRGGYTAFDVWGQGTLVTVSS SEQ ID NO: 99: IGKV1-39
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTP SEQ ID NO: 100: IGKV1-39/jk5
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPITFGQG
TRLEIK SEQ ID NO: 101: Isoform A human TGF-βRII
MGRGLLRGLWPLHIVLWTRIASTIPPHVQKSVNNDMIVTDNNGAVKFP
QLCKFCDVRFSTCDNQKSCMSNCSITSICEKPQEVCVAVWRKNDENITL
ETVCHDPKLPYHDFILEDAASPKCIMKEKKKPGETFFMCSCSSDECNDNI
IFSEEYNTSNPDLLLVIFQVTGISLLPPLGVAISVIIIFYCYRVNRQQKLSST
WETGKTRKLMEFSEHCAIILEDDRSDISSTCANNINHNTELLPIELDTLVG
KGRFAEVYKAKLKQNTSEQFETVAVKIFPYEEYASWKTEKDIFSDINLK
HENILQFLTAEERKTELGKQYWLITAFHAKGNLQEYLTRHVISWEDLRK
LGSSLARGIAHLHSDHTPCGRPKMPIVHRDLKSSNILVKNDLTCCLCDFG
LSLRLDPTLSVDDLANSGQVGTARYMAPEVLESRMNLENVESFKQTDV
YSMALVLWEMTSRCNAVGEVKDYEPPFGSKVREHPCVESMKDNVLRD
RGRPEIPSFWLNHQGIQMVCETLTECWDHDPEARLTAQCVAERFSELEH
LDRLSGRSCSEEKIPEDGSLNTTK SEQ ID NO: 102: Extracellular domain of isoform A of human TGF-βRII
TIPPHVQKSVNNDMIVTDNNGAVKFPQLCKFCDVRFSTCDNQKSCMSN
CSITSICEKPQEVCVAVWRKNDENITLETVCHDPKLPYHDFILEDAASPK
CIMKEKKKPGETFFMCSCSSDECNDNIIFSEEYNTSNPDLLLVIFQ SEQ ID NO: 103: Isoform B human TGFBRII
MGRGLLRGLWPLHIVLWTRIASTIPPHVQKSDVEMEAQKDEIICPSCNRT
AHPLRHINNDMIVTDNNGAVKFPQLCKFCDVRFSTCDNQKSCMSNCSIT
SICEKPQEVCVAVWRKNDENITLETVCHDPKLPYHDFILEDAASPKCIMK
EKKKPGETFFMCSCSSDECNDNIIFSEEYNTSNPDLLLVIFQVTGISLLPPL
GVAISVIIIFYCYRVNRQQKLSSTWETGKTRKLMEFSEHCAIILEDDRSDI
SSTCANNINHNTELLPIELDTLVGKGRFAEVYKAKLKQNTSEQFETVAV
KIFPYEEYASWKTEKDIFSDINLKHENILQFLTAEERKTELGKQYWLITAF
HAKGNLQEYLTRHVISWEDLRKLGSSLARGIAHLHSDHTPCGRPKMPIV
HRDLKSSNILVKNDLTCCLCDFGLSLRLDPTLSVDDLANSGQVGTARYM
APEVLESRMNLENVESFKQTDVYSMALVLWEMTSRCNAVGEVKDYEP
PFGSKVREHPCVESMKDNVLRDRGRPEIPSFWLNHQGIQMVCETLTECW
DHDPEARLTAQCVAERFSELEHLDRLSGRSCSEEKIPEDGSLNTTK -continued

| SEQUENCES |
| --- |

SEQ ID NO: 104: Extracellular domain of isoform B of human TGF-βRII
TIPPHVQKSDVEMEAQKDEIICPSCNRTAHPLRHINNDMIVTDNNGAVKF
PQLCKFCDVRFSTCDNQKSCMSNCSITSICEKPQEVCVAVWRKNDENIT
LETVCHDPKLPYHDFILEDAASPKCIMKEKKKPGETFFMCSCSSDECND
NIIFSEEYNTSNPDLLLVIFQ SEQ ID NO: 105: HCDR1 according to Kabat
NAWMS SEQ ID NO: 106: HCDR2 according to Kabat
RIKTTISGGATQFAAPVKG SEQ ID NO: 107: HCDR3 according to Kabat
DLRDY SEQ ID NO: 108: HCDR1 according to Kabat
RYAMS SEQ ID NO: 109: HCDR2 according to Kabat
AISAGGDRTANTDSVKG SEQ ID NO: 110: HCDR3 according to Kabat
GTAARGKNYFDP SEQ ID NO: 111: HCDR1 according to Kabat
RYAMS SEQ ID NO: 112: HCDR2 according to Kabat
AISASGDRTKNTDSVKG SEQ ID NO: 113: HCDR3 according to Kabat
GTAAAGKNYFDP SEQ ID NO: 114: HCDR1 according to Kabat
RYAMS SEQ ID NO: 115: HCDR2 according to Kabat
AISASGDRYHNTDSVKG SEQ ID NO: 116: HCDR3 according to Kabat
GTAASGKNYFDP SEQ ID NO: 117: HCDR1 according to Kabat
RYAMS SEQ ID NO: 118: HCDR2 according to Kabat
AISASGDRTHNTDSVKG SEQ ID NO: 119: HCDR3 according to Kabat
GTAARGKNYFDP SEQ ID NO: 120: HCDR1 according to Kabat
NYWMS SEQ ID NO: 121: HCDR2 according to Kabat
RIKTTYSGGATDFAAPVKG SEQ ID NO: 122: HCDR3 according to Kabat
DLRDY SEQ ID NO: 123: HCDR1 according to Kabat
RYAMS SEQ ID NO: 124: HCDR2 according to Kabat
SISASGDRTHNTDSVKG SEQ ID NO: 125: HCDR3 according to Kabat
GLAASGKNYFDP SEQ ID NO: 126: HCDR1 according to Kabat
RYAMS SEQ ID NO: 127: HCDR2 according to Kabat
AISASGDRTDNTDSVKG -continued

| SEQUENCES |
| --- |

SEQ ID NO: 128: HCDR3 according to Kabat
GIARSGKNFFDP

SEQ ID NO: 129: HCDR1 according to Kabat
RAWMS

SEQ ID NO: 130: HCDR2 according to Kabat
RIKTTISGAATDFAAPVKG

SEQ ID NO: 131: HCDR3 according to Kabat
DLRDY

SEQ ID NO: 132: HCDR1 according to Kabat
RYAMS

SEQ ID NO: 133: HCDR2 according to Kabat
AISASGDRTLNTDSVKG

SEQ ID NO: 134: HCDR3 according to Kabat
GTAARGKNYFDP

SEQ ID NO: 135: Light chain variable region
EIVLTQSPATLSLSPGERATLSCRASQSVRSYLAWYQQKPGQAPRLLIYD
ASNRATGIPARFSGSGSGTDFTLTISSLEPEDFAVYYCQQRSNWPPTFGQ
GTKVEIK SEQ ID NO: 136: Heavy chain variable region
EVQLVESGGGVVQPGRSLRLSCAASGFTFSNYGMHWVRQAPGKGLEW
VAVISYDGSTKYSADSLKGRFTISRDNSKNTLYLQMNSLRADDTAVYYC
AKEGWSFDSSGYRSWFDSWGQGTLVTVSS

| SEQUENCE LISTING |
| --- |

<160> NUMBER OF SEQ ID NOS: 136

<210> SEQ ID NO 1
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 1

Ile Tyr Ala Met Thr
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 2

Val Ile Ser Gly Ser Gly Gly Thr Thr Tyr Tyr Ala Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: HCDR3 according to Kabat

```
<400> SEQUENCE: 3

Arg Gly Gln Tyr Arg Asp Ile Val Gly Ala Thr Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 4

Asn Ala Trp Met Ser
1               5

<210> SEQ ID NO 5
<211> LENGTH: 19
<212> TYPE: PRT
<213> ORGANISM: Artificial Sequence
<220> FEATURE:
<223> OTHER INFORMATION: HCDR2 according to Kabat

<400> SEQUENCE: 5

Arg Ile Lys Thr Thr Ile Ser Gly Gly Ala Thr Asp Phe Ala Ala Pro
1               5                   10                  15

Val Lys Gly

<210> SEQ ID NO 6
<211> LENGTH: 5
<212> TYPE: PRT
<213> ORGANISM: Artificial Sequence
<220> FEATURE:
<223> OTHER INFORMATION: HCDR3 according to Kabat

<400> SEQUENCE: 6

Asp Leu Arg Asp Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 7

Arg Tyr Ala Met Ser
1               5

<210> SEQ ID NO 8
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 8

Ala Ile Ser Ala Ser Gly Asp Arg Thr His Asn Thr Asp Ser Val Lys
1               5                   10                  15

Gly

<210> SEQ ID NO 9
<211> LENGTH: 12
<212> TYPE: PRT
```

<213> ORGANISM: Artificial Sequence
<220> FEATURE:
<223> OTHER INFORMATION: HCDR3 according to Kabat

<400> SEQUENCE: 9

Gly Ile Ala Ala Ser Gly Lys Asn Tyr Phe Asp Pro
1               5                   10

<210> SEQ ID NO 10
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Tyr
            20                  25                  30

Ala Met Thr Trp Val Arg Gln Ala Pro Gly Lys Gly Leu Glu Trp Val
            35                  40                  45

Ser Val Ile Ser Gly Ser Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Asp Ile Val Gly Ala Thr Asp Tyr Trp
            100                 105                 110

Gly Gln Gly Thr Leu Val Thr Val Ser Ser
        115                 120

<210> SEQ ID NO 11
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 11

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Thr Thr Ile Ser Gly Gly Ala Thr Asp Phe Ala Ala
            50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Asp Tyr Trp Gly Gln Gly Thr Leu Val
            100                 105                 110

Thr Val Ser Ser
        115

<210> SEQ ID NO 12

```
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 12

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Ala Ser Gly Lys Asn Tyr Phe Asp Pro Trp Gly
            100                 105                 110

Gln Gly Thr Leu Val Thr Val Ser Ser
        115                 120

<210> SEQ ID NO 13
<211> LENGTH: 6
<212> TYPE: PRT
<213> ORGANISM: Artificial Sequence
<220> FEATURE:
<223> OTHER INFORMATION: LCDR1 according to IMGT

<400> SEQUENCE: 13

Gln Ser Ile Ser Ser Tyr
1               5

<210> SEQ ID NO 14
<211> LENGTH: 3
<212> TYPE: PRT
<213> ORGANISM: Artificial Sequence
<220> FEATURE:
<223> OTHER INFORMATION: LCDR2 according to IMGT

<400> SEQUENCE: 14

Ala Ala Ser
1

<210> SEQ ID NO 15
<211> LENGTH: 9
<212> TYPE: PRT
<213> ORGANISM: Artificial Sequence
<220> FEATURE:
<223> OTHER INFORMATION: LCDR3 according to IMGT

<400> SEQUENCE: 15

Gln Gln Ser Tyr Ser Thr Pro Pro Thr
1               5

<210> SEQ ID NO 16
<211> LENGTH: 107
<212> TYPE: PRT
<213> ORGANISM: Homo sapiens
```

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 17
<211> LENGTH: 329
<212> TYPE: PRT
<213> ORGANISM: Artificial Sequence
<220> FEATURE:
<223> OTHER INFORMATION: Heavy chain constant region

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

68

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 18
<211> LENGTH: 107
<212> TYPE: PRT
<213> ORGANISM: Artificial Sequence
<220> FEATURE:
<223> OTHER INFORMATION: Light chain constant region

<400> SEQUENCE: 18

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 19
<211> LENGTH: 11
<212> TYPE: PRT
<213> ORGANISM: Artificial Sequence
<220> FEATURE:
<223> OTHER INFORMATION: LCDR1 according to Kabat

<400> SEQUENCE: 19

Arg Ala Ser Gln Ser Ile Ser Ser Tyr Leu Asn
1                   5                   10

<210> SEQ ID NO 20
<211> LENGTH: 7
<212> TYPE: PRT
<213> ORGANISM: Artificial Sequence
<220> FEATURE:
<223> OTHER INFORMATION: LCDR2 according to Kabat

<400> SEQUENCE: 20

Ala Ala Ser Ser Leu Gln Ser
1                   5

<210> SEQ ID NO 21
<211> LENGTH: 9
<212> TYPE: PRT
```

<213> ORGANISM: Artificial Sequence
<220> FEATURE:
<223> OTHER INFORMATION: LCDR3 according to Kabat

<400> SEQUENCE: 21

Gln Gln Ser Tyr Ser Thr Pro Pro Thr
1               5

<210> SEQ ID NO 22
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Asn
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Asp Ile Val Gly Ala Thr Asp Tyr Trp
            100                 105                 110

Gly Gln Gly Thr Leu Val Thr Val Ser Ser
        115                 120

<210> SEQ ID NO 23
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Gln
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Asp Ile Val Gly Ala Thr Asp Tyr Trp
            100                 105                 110

Gly Gln Gly Thr Leu Val Thr Val Ser Ser
        115                 120

<210> SEQ ID NO 24

```
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Tyr
            20                  25                  30

Arg Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Gln Tyr Arg Glu Ile Val Gly Ala Thr Asp Tyr Trp
            100                 105                 110

Gly Gln Gly Thr Leu Val Thr Val Ser Ser
        115                 120

<210> SEQ ID NO 25
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Tyr Phe Asp Ile Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gln Tyr Arg Asp Lys Val Gly Ala Thr Asp Tyr Trp
            100                 105                 110

Gly Gln Gly Thr Leu Val Thr Val Ser Ser
        115                 120

<210> SEQ ID NO 26
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 26

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Asp Ile Asn
        20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Glu Ile Ala Gly Ala Thr Asp Tyr Trp
            100                 105                 110

Gly Gln Gly Thr Leu Val Thr Val Ser Ser
        115                 120

<210> SEQ ID NO 27
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 27

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Ala Phe Asp Ile Tyr
        20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Asp Ile Val Gly Ala Thr Asp Tyr Trp
            100                 105                 110

Gly Gln Gly Thr Leu Val Thr Val Ser Ser
        115                 120

<210> SEQ ID NO 28
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 28

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Asp Ile Tyr
        20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
            85                  90                  95

Ala Arg Arg Gly Gln Tyr Arg Asp Ile Ala Gly Gly Thr Asp Tyr Trp
            100                 105                 110

Gly Gln Gly Thr Leu Val Thr Val Ser Ser
        115                 120

<210> SEQ ID NO 29
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Asp Ile Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Arg Ser Gln Tyr Arg Asp Lys Val Gly Ala Thr Asp Tyr Trp
            100                 105                 110

Gly Gln Gly Thr Leu Val Thr Val Ser Ser
        115                 120

<210> SEQ ID NO 30
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Arg Phe Asp Ile Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Arg Gly Gln Tyr Arg Arg Ile Val Gly Ala Thr Asp Tyr Trp
            100                 105                 110

Gly Gln Gly Thr Leu Val Thr Val Ser Ser
        115                 120
```

<210> SEQ ID NO 31
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Asn
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Tyr Ile Ala Gly Ala Thr Asp Tyr Trp
            100                 105                 110

Gly Gln Gly Thr Leu Val Thr Val Ser Ser
        115                 120

<210> SEQ ID NO 32
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Thr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Asp Ile Ala Gly Ala Thr Asp Tyr Trp
            100                 105                 110

Gly Gln Gly Thr Leu Val Thr Val Ser Ser
        115                 120

<210> SEQ ID NO 33
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 33

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Phe Ser Phe Asp Ile Tyr
            20                  25                  30

Ala Met Thr Trp Val Arg Gln Ala Pro Gly Lys Gly Leu Glu Trp Val
            35                  40                  45

Ser Val Ile Ser Gly Ser Gly Gly Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gln Tyr Arg Asp Lys Val Gly Ala Thr Asp Tyr Trp
            100                 105                 110

Gly Gln Gly Thr Leu Val Thr Val Ser Ser
        115                 120
```

<210> SEQ ID NO 34
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Tyr
            20                  25                  30

Ala Met Thr Trp Val Arg Gln Ala Pro Gly Lys Gly Leu Glu Trp Val
            35                  40                  45

Ser Val Ile Ser Gly Ser Gly Gly Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Tyr Val Val Gly Ala Thr Asp Tyr Trp
            100                 105                 110

Gly Gln Gly Thr Leu Val Thr Val Ser Ser
        115                 120
```

<210> SEQ ID NO 35
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Tyr Phe Asp Ile Tyr
            20                  25                  30

Ala Met Thr Trp Val Arg Gln Ala Pro Gly Lys Gly Leu Glu Trp Val
            35                  40                  45

Ser Val Ile Ser Gly Ser Gly Gly Thr Thr Tyr Tyr Ala Asp Ser Val
        50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg His Ile Ala Gly Ala Thr Asp Tyr Trp
            100                 105                 110

Gly Gln Gly Thr Leu Val Thr Val Ser Ser
        115                 120
```

```
<210> SEQ ID NO 36
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 36
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Arg Phe Asp Ile Tyr
            20                  25                  30

Ala Met Thr Trp Val Arg Gln Ala Pro Gly Lys Gly Leu Glu Trp Val
            35                  40                  45

Ser Val Ile Ser Gly Ser Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Asp Ile Val Gly Ala Thr Asp Tyr Trp
            100                 105                 110

Gly Gln Gly Thr Leu Val Thr Val Ser Ser
        115                 120
```

```
<210> SEQ ID NO 37
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 37
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ile Asn
            20                  25                  30

Ala Met Thr Trp Val Arg Gln Ala Pro Gly Lys Gly Leu Glu Trp Val
            35                  40                  45

Ser Val Ile Ser Gly Ser Gly Ala Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gln Tyr Arg Glu Ile Gln Gly Ala Asn Asp Tyr Trp
            100                 105                 110
```

-continued

```
Gly Gln Gly Thr Leu Val Thr Val Ser Ser
        115                 120

<210> SEQ ID NO 38
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 38

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Arg Ala
            20                  25                  30

Trp Met Ser Trp Val Arg Gln Ala Pro Gly Lys Gly Leu Glu Trp Val
        35                  40                  45

Gly Arg Ile Lys Thr Thr Ile Ser Gly Gly Ala Thr Gln Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Asn Tyr Trp Gly Gln Gly Thr Leu Val
            100                 105                 110

Thr Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 39

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Arg Ala
            20                  25                  30

Trp Met Ser Trp Val Arg Gln Ala Pro Gly Lys Gly Leu Glu Trp Val
        35                  40                  45

Gly Arg Ile Lys Thr Thr Val Ser Gly Gly Ala Thr Ala Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Ala Tyr Trp Gly Gln Gly Thr Leu Val
            100                 105                 110

Thr Val Ser Ser
        115

<210> SEQ ID NO 40
<211> LENGTH: 116
<212> TYPE: PRT
<213> ORGANISM: Artificial Sequence
<220> FEATURE:
<223> OTHER INFORMATION: Heavy chain variable region
```

<400> SEQUENCE: 40

Gln Val Gln Leu Val Glu Ser Gly Gly Gly Leu Val Glu Pro Gly Gly
1                   5                   10                  15

Ser Leu Arg Leu Ser Cys Ala Ala Ser Gly Phe Thr Phe Ser Asn Tyr
                20                  25                  30

Trp Met Ser Trp Val Arg Gln Ala Pro Gly Lys Gly Leu Glu Trp Val
            35                  40                  45

Gly Arg Ile Lys Thr Thr Tyr Ser Gly Gly Ala Thr Asp Phe Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Asp Tyr Trp Gly Gln Gly Thr Leu Val
                100                 105                 110

Thr Val Ser Ser
        115

<210> SEQ ID NO 41
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 41

Gln Val Gln Leu Val Glu Ser Gly Gly Gly Leu Val Glu Pro Gly Gly
1                   5                   10                  15

Ser Leu Arg Leu Ser Cys Ala Ala Ser Gly Phe Thr Phe Ser Arg Ala
                20                  25                  30

Trp Met Ser Trp Val Arg Gln Ala Pro Gly Lys Gly Leu Glu Trp Val
            35                  40                  45

Gly Arg Ile Lys Thr Thr Tyr Ser Gly Gly Ala Thr Asp Phe Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Lys Tyr Trp Gly Gln Gly Thr Leu Val
                100                 105                 110

Thr Val Ser Ser
        115

<210> SEQ ID NO 42
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 42

Gln Val Gln Leu Val Glu Ser Gly Gly Gly Leu Val Glu Pro Gly Gly
1                   5                   10                  15

Ser Leu Arg Leu Ser Cys Ala Ala Ser Gly Phe Thr Phe Ser Arg Ala
                20                  25                  30

Trp Met Ser Trp Val Arg Gln Ala Pro Gly Lys Gly Leu Glu Trp Val
            35                  40                  45

```
Gly Arg Ile Lys Thr Thr Ile Ser Gly Gly Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Ala Tyr Trp Gly Gln Gly Thr Leu Val
                100                 105                 110

Thr Val Ser Ser
        115

<210> SEQ ID NO 43
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 43

Gln Val Gln Leu Val Glu Ser Gly Gly Gly Leu Val Glu Pro Gly Gly
1                   5                   10                  15

Ser Leu Arg Leu Ser Cys Ala Ala Ser Gly Phe Lys Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Thr Thr Ile Ser Gly Gly Ala Thr Gln Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Asp Tyr Trp Gly Gln Gly Thr Leu Val
                100                 105                 110

Thr Val Ser Ser
        115

<210> SEQ ID NO 44
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 44

Gln Val Gln Leu Val Glu Ser Gly Gly Gly Leu Val Glu Pro Gly Gly
1                   5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Thr Thr Tyr Ser Gly Gly Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95
```

-continued

```
Tyr Cys Thr Leu Asp Leu Arg Asp Tyr Trp Gly Gln Gly Thr Leu Val
            100                 105                 110

Thr Val Ser Ser
        115

<210> SEQ ID NO 45
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 45

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Thr Thr Tyr Ser Gly Gly Ala Thr Glu Phe Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Lys Tyr Trp Gly Gln Gly Thr Leu Val
            100                 105                 110

Thr Val Ser Ser
        115

<210> SEQ ID NO 46
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 46

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
            35                  40                  45

Gly Arg Ile Lys Thr Thr Ile Ser Gly Gly Ala Thr Asp Phe Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Ala Tyr Trp Gly Gln Gly Thr Leu Val
            100                 105                 110

Thr Val Ser Ser
        115

<210> SEQ ID NO 47
<211> LENGTH: 116
<212> TYPE: PRT
```

-continued

<213> ORGANISM: Artificial Sequence
<220> FEATURE:
<223> OTHER INFORMATION: Heavy chain variable region

<400> SEQUENCE: 47

```
Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Arg Ala
            20                  25                  30

Trp Met Ser Trp Val Arg Gln Ala Pro Gly Lys Gly Leu Glu Trp Val
        35                  40                  45

Gly Arg Ile Lys Thr Thr Ile Ser Gly Ala Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Asp Tyr Trp Gly Gln Gly Thr Leu Val
            100                 105                 110

Thr Val Ser Ser
        115
```

<210> SEQ ID NO 48
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 48

```
Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ala Asn Ala
            20                  25                  30

Trp Met Ser Trp Val Arg Gln Ala Pro Gly Lys Gly Leu Glu Trp Val
        35                  40                  45

Gly Arg Ile Lys Thr Thr Tyr Ser Gly Gly Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Lys Tyr Trp Gly Gln Gly Thr Leu Val
            100                 105                 110

Thr Val Ser Ser
        115
```

<210> SEQ ID NO 49
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 49

```
Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Gln Phe Ser Asn Ala
            20                  25                  30
```

-continued

```
Trp Met Ser Trp Val Arg Gln Ala Pro Gly Lys Gly Leu Glu Trp Val
        35                  40                  45

Gly Arg Ile Lys Thr Thr Tyr Ser Gly Gly Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Asp Tyr Trp Gly Gln Gly Thr Leu Val
            100                 105                 110

Thr Val Ser Ser
        115

<210> SEQ ID NO 50
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 50

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ala
            20                  25                  30

His Met Ser Trp Val Arg Gln Ala Pro Gly Lys Gly Leu Glu Trp Val
        35                  40                  45

Gly Arg Ile Lys Thr Thr Tyr Ser Gly Gly Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Gln Tyr Trp Gly Gln Gly Thr Leu Val
            100                 105                 110

Thr Val Ser Ser
        115

<210> SEQ ID NO 51
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 51

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ala Asn Ala
            20                  25                  30

Trp Met Ser Trp Val Arg Gln Ala Pro Gly Lys Gly Leu Glu Trp Val
        35                  40                  45

Gly Arg Ile Lys Thr Thr Tyr Ser Gly Gly Ala Thr Glu Phe Ala Ala
    50                  55                  60

Pro Val Lys Gly Arg Phe Thr Ile Ser Arg Asp Asp Ser Lys Asn Thr
65                  70                  75                  80
```

-continued

___

Leu Tyr Leu Gln Met Asn Ser Leu Lys Thr Glu Asp Thr Ala Val Tyr
                85                      90                      95

Tyr Cys Thr Leu Asp Leu Arg Thr Tyr Trp Gly Gln Gly Thr Leu Val
                100                     105                     110

Thr Val Ser Ser
        115

<210> SEQ ID NO 52
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 52

Gln Val Gln Leu Val Glu Ser Gly Gly Gly Leu Val Glu Pro Gly Gly
1                   5                       10                      15

Ser Leu Arg Leu Ser Cys Ala Ala Ser Gly Phe Thr Phe Ser Asn Ala
                20                      25                      30

Trp Met Ser Trp Val Arg Gln Ala Pro Gly Lys Gly Leu Glu Trp Val
                35                      40                      45

Gly Arg Ile Lys Thr Thr Tyr Ser Gly Gly Ala Thr Asp Phe Ala Ala
        50                      55                      60

Pro Val Lys Gly Arg Phe Thr Ile Ser Arg Asp Asp Ser Lys Asn Thr
65                      70                      75                      80

Leu Tyr Leu Gln Met Asn Ser Leu Lys Thr Glu Asp Thr Ala Val Tyr
                85                      90                      95

Tyr Cys Thr Leu Asp Leu Arg Ser Tyr Trp Gly Gln Gly Thr Leu Val
                100                     105                     110

Thr Val Ser Ser
        115

<210> SEQ ID NO 53
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 53

Gln Val Gln Leu Val Glu Ser Gly Gly Gly Leu Val Glu Pro Gly Gly
1                   5                       10                      15

Ser Leu Arg Leu Ser Cys Ala Ala Ser Gly Phe Gln Phe Ser Asn Ala
                20                      25                      30

Trp Met Ser Trp Val Arg Gln Ala Pro Gly Lys Gly Leu Glu Trp Val
                35                      40                      45

Gly Arg Ile Lys Thr Thr Ile Ser Gly Gly Ala Thr Glu Phe Ala Ala
        50                      55                      60

Pro Val Lys Gly Arg Phe Thr Ile Ser Arg Asp Asp Ser Lys Asn Thr
65                      70                      75                      80

Leu Tyr Leu Gln Met Asn Ser Leu Lys Thr Glu Asp Thr Ala Val Tyr
                85                      90                      95

Tyr Cys Thr Leu Asp Leu Arg Asp Tyr Trp Gly Gln Gly Thr Leu Val
                100                     105                     110

Thr Val Ser Ser
        115

```
<210> SEQ ID NO 54
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 54

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe Val Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Thr Thr Phe Ser Gly Gly Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Lys Tyr Trp Gly Gln Gly Thr Leu Val
            100                 105                 110

Thr Val Ser Ser
        115

<210> SEQ ID NO 55
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 55

Gln Val Gln Leu Val Glu Ser Gly Gly Gly Leu Val Glu Pro Gly Gly
1               5                   10                  15

Ser Leu Arg Leu Ser Cys Ala Ala Ser Gly Phe His Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Thr Thr Ile Ser Gly Gly Ala Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Asp Leu Arg Ala Tyr Trp Gly Gln Gly Thr Leu Val
            100                 105                 110

Thr Val Ser Ser
        115

<210> SEQ ID NO 56
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 56

Gln Val Gln Leu Val Glu Ser Gly Gly Gly Leu Val Glu Pro Gly Gly
1               5                   10                  15
```

Ser Leu Arg Leu Ser Cys Ala Ala Ser Gly Phe Lys Phe Ser Asn Ala
            20                      25                      30

Trp Met Ser Trp Val Arg Gln Ala Pro Gly Lys Gly Leu Glu Trp Val
            35                      40                      45

Gly Arg Ile Lys Thr Thr Ile Ser Gly Gly Lys Thr Glu Phe Ala Ala
    50                      55                      60

Pro Val Lys Gly Arg Phe Thr Ile Ser Arg Asp Asp Ser Lys Asn Thr
65                      70                      75                      80

Leu Tyr Leu Gln Met Asn Ser Leu Lys Thr Glu Asp Thr Ala Val Tyr
                85                      90                      95

Tyr Cys Thr Leu Asp Leu Arg Arg Tyr Trp Gly Gln Gly Thr Leu Val
            100                     105                     110

Thr Val Ser Ser
        115

<210> SEQ ID NO 57
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 57

Gln Val Gln Leu Val Glu Ser Gly Gly Gly Leu Val Gln Pro Gly Gly
1                   5                       10                      15

Ser Leu Arg Leu Ser Cys Ala Val Ser Gly Phe Ala Phe Arg Arg Tyr
            20                      25                      30

Ala Met Ser Trp Val Arg Gln Ala Pro Gly Lys Gly Leu Glu Trp Val
            35                      40                      45

Ser Ala Ile Ser Ala Ser Gly Asp Arg Thr His Asn Thr Asp Ser Val
    50                      55                      60

Lys Gly Arg Phe Ser Ile Ser Arg Asp Asn Ser Lys Asn Thr Leu Tyr
65                      70                      75                      80

Leu Gln Met Asn Ser Leu Arg Ala Glu Asp Thr Ala Val Tyr Phe Cys
                85                      90                      95

Ala Lys Gly Ile Ala Lys Arg Gly Lys Asn Tyr Phe Asp Pro Trp Gly
            100                     105                     110

Gln Gly Thr Leu Val Thr Val Ser Ser
        115                     120

<210> SEQ ID NO 58
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 58

Gln Val Gln Leu Val Glu Ser Gly Gly Gly Leu Val Gln Pro Gly Gly
1                   5                       10                      15

Ser Leu Arg Leu Ser Cys Ala Val Ser Gly Phe Gln Phe Arg Arg Tyr
            20                      25                      30

Ala Met Ser Trp Val Arg Gln Ala Pro Gly Lys Gly Leu Glu Trp Val
            35                      40                      45

Ser Ala Ile Ser Ala Ser Gly Asp Arg Thr His Asn Thr Asp Ser Val
    50                      55                      60

```
Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Lys Ser Gly Lys Asn Tyr Phe Asp Pro Trp Gly
            100                 105                 110

Gln Gly Thr Leu Val Thr Val Ser Ser
        115                 120

<210> SEQ ID NO 59
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 59

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Lys Ser Gly Lys Asn Tyr Phe Asp Pro Trp Gly
            100                 105                 110

Gln Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 60

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Lys Phe Arg Arg Tyr
            20                  25                  30

Ala Met Ser Trp Val Arg Gln Ala Pro Gly Lys Gly Leu Glu Trp Val
        35                  40                  45

Ser Ser Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Leu Ala Ala Ser Gly Lys Asn Tyr Phe Asp Pro Trp Gly
            100                 105                 110
```

```
Gln Gly Thr Leu Val Thr Val Ser Ser
        115                 120

<210> SEQ ID NO 61
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 61

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Arg Phe Arg Arg Tyr
            20                  25                  30

Ala Met Ser Trp Val Arg Gln Ala Pro Gly Lys Gly Leu Glu Trp Val
            35                  40                  45

Ser Ala Ile Ser Ala Ser Gly Asp Arg Thr His Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Tyr Ala Ser Gly Lys His Tyr Phe Asp Pro Trp Gly
            100                 105                 110

Gln Gly Thr Leu Val Thr Val Ser Ser
        115                 120

<210> SEQ ID NO 62
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 62

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Arg Arg Tyr
            20                  25                  30

Ala Met Ser Trp Val Arg Gln Ala Pro Gly Lys Gly Leu Glu Trp Val
            35                  40                  45

Ser Ala Ile Ser Ala Ser Gly Asp Arg Thr Lys Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Ser Gly Arg Asn Tyr Phe Asp Pro Trp Gly
            100                 105                 110

Gln Gly Thr Leu Val Thr Val Ser Ser
        115                 120

<210> SEQ ID NO 63
<211> LENGTH: 121
<212> TYPE: PRT
<213> ORGANISM: Artificial Sequence
<220> FEATURE:
<223> OTHER INFORMATION: Heavy chain variable region
```

<400> SEQUENCE: 63

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Phe Arg Arg Tyr
            20                  25                  30

Ala Met Ser Trp Val Arg Gln Ala Pro Gly Lys Gly Leu Glu Trp Val
        35                  40                  45

Ser Ser Ile Ser Ala Ser Gly Asp Arg Thr Lys Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Ala Ser Gly Lys Asn Tyr Phe Asp Pro Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Phe Ala Ser Gly Lys His Tyr Phe Asp Pro Trp Gly
            100                 105                 110

Gln Gly Thr Leu Val Thr Val Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 65

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Gly Arg Tyr
            20                  25                  30

Ala Met Ser Trp Val Arg Gln Ala Pro Gly Lys Gly Leu Glu Trp Val
        35                  40                  45

```
Ser Ala Ile Ser Ala Ser Gly Asp Arg His His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Lys Ser Gly Lys Asn Tyr Phe Asp Pro Trp Gly
                100                 105                 110

Gln Gly Thr Leu Val Thr Val Ser Ser
        115                 120
```

<210> SEQ ID NO 66
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 66

```
Gln Val Gln Leu Val Glu Ser Gly Gly Gly Leu Val Gln Pro Gly Gly
1                   5                   10                  15

Ser Leu Arg Leu Ser Cys Ala Val Ser Gly Phe Gln Phe Arg Arg Tyr
                20                  25                  30

Ala Met Ser Trp Val Arg Gln Ala Pro Gly Lys Gly Leu Glu Trp Val
            35                  40                  45

Ser Asp Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Arg Ser Gly Lys Asn Tyr Phe Asp Pro Trp Gly
                100                 105                 110

Gln Gly Thr Leu Val Thr Val Ser Ser
        115                 120
```

<210> SEQ ID NO 67
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 67

```
Gln Val Gln Leu Val Glu Ser Gly Gly Gly Leu Val Gln Pro Gly Gly
1                   5                   10                  15

Ser Leu Arg Leu Ser Cys Ala Val Ser Gly Phe Thr Phe Arg Arg Tyr
                20                  25                  30

Ala Met Ser Trp Val Arg Gln Ala Pro Gly Lys Gly Leu Glu Trp Val
            35                  40                  45

Ser Ala Ile Ser Ala Ser Gly Asp Arg Thr Leu Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95
```

-continued

```
Ala Lys Gly Thr Ala Ala Arg Gly Lys Asn Tyr Phe Asp Pro Trp Gly
            100                 105                 110

Gln Gly Thr Leu Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 68

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Phe Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Ser Gly Lys Asn Phe Phe Asp Pro Trp Gly
            100                 105                 110

Gln Gly Thr Leu Val Thr Val Ser Ser
        115                 120

<210> SEQ ID NO 69
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr Lys Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Ser Gly Lys Asn Phe Phe Asp Pro Trp Gly
            100                 105                 110

Gln Gly Thr Leu Val Thr Val Ser Ser
        115                 120

<210> SEQ ID NO 70
<211> LENGTH: 121
<212> TYPE: PRT
```

<213> ORGANISM: Artificial Sequence
<220> FEATURE:
<223> OTHER INFORMATION: Heavy chain variable region

<400> SEQUENCE: 70

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr Lys Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Ala Gly Lys Asn Tyr Phe Asp Pro Trp Gly
            100                 105                 110

Gln Gly Thr Leu Val Thr Val Ser Ser
        115                 120

<210> SEQ ID NO 71
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 71

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Gln Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala His Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Ser Gly Lys Asn Tyr Phe Asp Pro Trp Gly
            100                 105                 110

Gln Gly Thr Leu Val Thr Val Ser Ser
        115                 120

<210> SEQ ID NO 72
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Ile Arg Arg Tyr
            20                  25                  30

-continued

```
Ala Met Ser Trp Val Arg Gln Ala Pro Gly Lys Gly Leu Glu Trp Val
        35                  40                  45

Ser Tyr Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Asn Ser Gly Lys Asn Tyr Phe Asp Pro Trp Gly
               100                 105                 110

Gln Gly Thr Leu Val Thr Val Ser Ser
        115                 120

<210> SEQ ID NO 73
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Arg Arg Tyr
        20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Arg Gly Lys Asn Tyr Phe Asp Pro Trp Gly
               100                 105                 110

Gln Gly Thr Leu Val Thr Val Ser Ser
        115                 120

<210> SEQ ID NO 74
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 74

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Glu Arg Tyr
        20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr Gln Asn Thr Asp Ser Val
    50                  55                  60

Lys Gly Arg Phe Ser Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Phe Cys
                85                      90                      95

Ala Lys Gly Thr Ala Ala Ser Gly Arg Asn Tyr Phe Asp Pro Trp Gly
            100                     105                     110

Gln Gly Thr Leu Val Thr Val Ser Ser
        115                     120

<210> SEQ ID NO 75
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Glu Phe Arg Arg Tyr
            20                  25                  30

Ala Met Ser Trp Val Arg Gln Ala Pro Gly Lys Gly Leu Glu Trp Val
            35                  40                  45

Ser Ala Ile Ser Ala Gly Gly Asp Arg Thr Ala Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                      90                      95

Ala Lys Gly Thr Ala Ala Arg Gly Lys Asn Tyr Phe Asp Pro Trp Gly
            100                     105                     110

Gln Gly Thr Leu Val Thr Val Ser Ser
        115                     120

<210> SEQ ID NO 76
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 76

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Phe Arg Arg Tyr
            20                  25                  30

Ala Met Ser Trp Val Arg Gln Ala Pro Gly Lys Gly Leu Glu Trp Val
            35                  40                  45

Ser Ala Ile Ser Ala Ser Gly Asp Arg Thr Gln Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                      90                      95

Ala Lys Gly Thr Ala Ala Ser Gly Lys Asn Tyr Phe Asp Pro Trp Gly
            100                     105                     110

Gln Gly Thr Leu Val Thr Val Ser Ser
        115                     120

<210> SEQ ID NO 77
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 77

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ser Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr Leu Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Arg Gly Lys Asn Tyr Phe Asp Pro Trp Gly
            100                 105                 110

Gln Gly Thr Leu Val Thr Val Ser Ser
        115                 120

<210> SEQ ID NO 78
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 78

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Glu Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr Asp Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Arg Ser Gly Lys Asn Phe Phe Asp Pro Trp Gly
            100                 105                 110

Gln Gly Thr Leu Val Thr Val Ser Ser
        115                 120

<210> SEQ ID NO 79
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 79

Gln Val Gln Leu Val Glu Ser Gly Gly Gly Leu Val Gln Pro Gly Gly
1               5                   10                  15

```
Ser Leu Arg Leu Ser Cys Ala Val Ser Gly Phe Asn Phe Arg Arg Tyr
        20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
    50                  55                  60

Thr Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Leu Ala Ala Ser Gly Lys Asn Tyr Phe Asp Pro Trp Gly
                100                 105                 110

Gln Gly Thr Leu Val Thr Val Ser Ser
            115                 120
```

<210> SEQ ID NO 80
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 80

```
Gln Val Gln Leu Val Glu Ser Gly Gly Gly Leu Val Gln Pro Gly Gly
1                   5                   10                  15

Ser Leu Arg Leu Ser Cys Ala Val Ser Gly Phe Ala Phe Arg Arg Tyr
        20                  25                  30

Ala Met Ser Trp Val Arg Gln Ala Pro Gly Lys Gly Leu Glu Trp Val
        35                  40                  45

Ser Ala Ile Ser Ala His Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Ser Gly Lys Asn Tyr Phe Asp Pro Trp Gly
                100                 105                 110

Gln Gly Thr Leu Val Thr Val Ser Ser
            115                 120
```

<210> SEQ ID NO 81
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 81

```
Gln Val Gln Leu Val Glu Ser Gly Gly Gly Leu Val Gln Pro Gly Gly
1                   5                   10                  15

Ser Leu Arg Leu Ser Cys Ala Val Ser Gly Phe Thr Phe Arg Arg Tyr
        20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
    50                  55                  60
```

-continued

```
Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Leu Ala Ala Ser Gly Lys Asn Phe Phe Asp Pro Trp Gly
            100                 105                 110

Gln Gly Thr Leu Val Thr Val Ser Ser
        115                 120

<210> SEQ ID NO 82
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 82

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Phe Arg Arg Tyr
            20                  25                  30

Ala Met Ser Trp Val Arg Gln Ala Pro Gly Lys Gly Leu Glu Trp Val
            35                  40                  45

Ser Ser Ile Ser Ala Ser Gly Asp Arg Thr His Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Leu Ala Ser Ser Gly Lys Asn Tyr Phe Asp Pro Trp Gly
            100                 105                 110

Gln Gly Thr Leu Val Thr Val Ser Ser
        115                 120

<210> SEQ ID NO 83
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Gln Phe Arg Arg Tyr
            20                  25                  30

Ala Met Ser Trp Val Arg Gln Ala Pro Gly Lys Gly Leu Glu Trp Val
            35                  40                  45

Ser Ser Ile Ser Ala Ser Gly Asp Arg Thr His Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Leu Ala Ala Ser Gly Lys Asn Tyr Phe Asp Pro Trp Gly
            100                 105                 110
```

```
Gln Gly Thr Leu Val Thr Val Ser Ser
        115                 120
```

```
<210> SEQ ID NO 84
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Gln Phe Arg Arg Tyr
            20                  25                  30

Ala Met Ser Trp Val Arg Gln Ala Pro Gly Lys Gly Leu Glu Trp Val
            35                  40                  45

Ser Ala Ile Ser Ala Ser Gly Asp Arg Tyr His Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Ser Gly Lys Asn Tyr Phe Asp Pro Trp Gly
            100                 105                 110

Gln Gly Thr Leu Val Thr Val Ser Ser
        115                 120
```

```
<210> SEQ ID NO 85
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Lys Phe Arg Arg Tyr
            20                  25                  30

Ala Met Ser Trp Val Arg Gln Ala Pro Gly Lys Gly Leu Glu Trp Val
            35                  40                  45

Ser Ala Ile Ser Ala Ser Gly Asp Tyr Thr His Asn Thr Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Lys Ser Gly Lys Asn Tyr Phe Asp Pro Trp Gly
            100                 105                 110

Gln Gly Thr Leu Val Thr Val Ser Ser
        115                 120
```

```
<210> SEQ ID NO 86
<211> LENGTH: 121
<212> TYPE: PRT
<213> ORGANISM: Artificial Sequence
<220> FEATURE:
<223> OTHER INFORMATION: Heavy chain variable region
```

<400> SEQUENCE: 86

```
Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr Arg Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Thr Ser Gly Lys Asn Tyr Phe Asp Pro Trp Gly
            100                 105                 110

Gln Gly Thr Leu Val Thr Val Ser Ser
        115                 120
```

<210> SEQ ID NO 87
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 87

```
Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Lys Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Ser His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Leu Ala Ala Arg Gly Lys Asn Tyr Phe Asp Pro Trp Gly
            100                 105                 110

Gln Gly Thr Leu Val Thr Val Ser Ser
        115                 120
```

<210> SEQ ID NO 88
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 88

```
Gln Val Gln Leu Val Glu Ser Gly Gly Gly Leu Val Gln Pro Gly Gly
1               5                   10                  15

Ser Leu Arg Leu Ser Cys Ala Val Ser Gly Phe Asn Phe Arg Arg Tyr
            20                  25                  30

Ala Met Ser Trp Val Arg Gln Ala Pro Gly Lys Gly Leu Glu Trp Val
        35                  40                  45
```

```
Ser Ala Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Thr Ala Ala Arg Gly Lys Asn Tyr Phe Asp Pro Trp Gly
            100                 105                 110

Gln Gly Thr Leu Val Thr Val Ser Ser
        115                 120

<210> SEQ ID NO 89
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 89

Gln Val Gln Leu Val Glu Ser Gly Gly Gly Leu Val Gln Pro Gly Gly
1                   5                   10                  15

Ser Leu Arg Leu Ser Cys Ala Val Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Ala Ser Gly Lys Asn Phe Phe Asp Pro Trp Gly
            100                 105                 110

Gln Gly Thr Leu Val Thr Val Ser Ser
        115                 120

<210> SEQ ID NO 90
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 90

Gln Val Gln Leu Val Glu Ser Gly Gly Gly Leu Val Gln Pro Gly Gly
1                   5                   10                  15

Ser Leu Arg Leu Ser Cys Ala Val Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95
```

-continued

```
Ala Lys Gly Ile Ala Ala Arg Gly Lys Asn Tyr Phe Asp Pro Trp Gly
            100                 105                 110

Gln Gly Thr Leu Val Thr Val Ser Ser
        115                 120

<210> SEQ ID NO 91
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 91

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Arg Phe Arg Arg Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Asp Arg Thr His Asn Thr Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Gly Ile Ala Ala Arg Gly Lys Asn Phe Phe Asp Pro Trp Gly
            100                 105                 110

Gln Gly Thr Leu Val Thr Val Ser Ser
        115                 120

<210> SEQ ID NO 92
<211> LENGTH: 127
<212> TYPE: PRT
<213> ORGANISM: Artificial Sequence
<220> FEATURE:
<223> OTHER INFORMATION: Heavy chain variable region

<400> SEQUENCE: 92

Glu Val Gln Leu Val Glu Thr Gly Ala Glu Val Lys Lys Pro Gly Ala
1               5                   10                  15

Ser Val Lys Val Ser Cys Lys Ala Ser Asp Tyr Ile Phe Thr Lys Tyr
            20                  25                  30

Asp Ile Asn Trp Val Arg Gln Ala Pro Gly Gln Gly Leu Glu Trp Met
        35                  40                  45

Gly Trp Met Ser Ala Asn Thr Gly Asn Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Gly Asp Thr Ala Val Tyr Phe Cys
                85                  90                  95

Ala Arg Ser Ser Leu Phe Lys Thr Glu Thr Ala Pro Tyr Tyr His Phe
            100                 105                 110

Ala Leu Asp Val Trp Gly Gln Gly Thr Thr Val Thr Val Ser Ser
        115                 120                 125

<210> SEQ ID NO 93
<211> LENGTH: 116
<212> TYPE: PRT
```

-continued

<213> ORGANISM: Artificial Sequence
<220> FEATURE:
<223> OTHER INFORMATION: Heavy chain variable region

<400> SEQUENCE: 93

```
Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Val Lys Thr Thr Val Ser Gly Gly Thr Thr Asp Tyr Ala Ala
    50                  55                  60

Ala Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Ile Tyr
                85                  90                  95

Tyr Cys Thr Ile Asp Leu Arg Asp Tyr Trp Gly Gln Gly Thr Leu Val
            100                 105                 110

Thr Val Ser Ser
        115
```

<210> SEQ ID NO 94
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ser Ile Asn Thr Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Gly Ile Ala Ala Thr Gly Lys Asn Tyr Phe Asp Pro Trp Gly
            100                 105                 110

Gln Gly Thr Leu Val Thr Val Ser Ser
        115                 120
```

<210> SEQ ID NO 95
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 95

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

```
Ala Met Ser Trp Val Arg Gln Ala Pro Gly Lys Gly Leu Glu Trp Val
        35                  40                  45

Ser Ser Ile Asn Thr Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Ile Ala Ala Ala Gly Lys Asn Trp Phe Gly Pro Trp Gly
            100                 105                 110

Gln Gly Thr Leu Val Thr Val Ser Ser
        115                 120
```

<210> SEQ ID NO 96
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 96

```
Gln Val Gln Leu Val Glu Ser Gly Gly Gly Leu Val Gln Pro Gly Gly
1               5                   10                  15

Ser Leu Ser Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ser Ile Asn Thr Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ile Ala Ala Ser Gly Lys Asn Tyr Phe Asp Pro Trp Gly
            100                 105                 110

Gln Gly Thr Leu Val Thr Val Ser Ser
        115                 120
```

<210> SEQ ID NO 97
<211> LENGTH: 125
<212> TYPE: PRT
<213> ORGANISM: Artificial Sequence
<220> FEATURE:
<223> OTHER INFORMATION: Heavy chain variable region

<400> SEQUENCE: 97

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Thr Lys Tyr Ser Ala Asp Ser Leu
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Asp Asp Thr Ala Val Tyr Tyr Cys
              85                      90                      95

Ala Lys Glu Gly Trp Ser Phe Asp Ser Ser Gly Tyr Arg Ser Trp Phe
              100                     105                     110

Asp Ser Trp Gly Gln Gly Thr Leu Val Thr Val Ser Ser
              115                     120                     125

<210> SEQ ID NO 98
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 98

Gln Leu Gln Leu Gln Glu Ser Gly Pro Gly Leu Val Lys Pro Ser Glu
1               5                       10                      15

Thr Leu Ser Leu Thr Cys Thr Val Ser Gly Gly Ser Ile Ser Ser Ser
              20                      25                      30

Ser Tyr Tyr Trp Gly Trp Ile Arg Gln Pro Pro Gly Lys Gly Leu Glu
          35                      40                      45

Trp Ile Gly Ser Ile Tyr Tyr Ser Gly Ser Thr Tyr Tyr Asn Pro Ser
      50                      55                      60

Leu Lys Ser Arg Val Thr Ile Ser Val Asp Thr Ser Lys Asn Gln Phe
65                      70                      75                      80

Ser Leu Lys Leu Ser Ser Val Thr Ala Ala Asp Thr Ala Val Tyr Tyr
              85                      90                      95

Cys Ala Arg Ser Phe Arg Gly Gly Tyr Thr Ala Phe Asp Val Trp Gly
              100                     105                     110

Gln Gly Thr Leu Val Thr Val Ser Ser
              115                     120

<210> SEQ ID NO 99
<211> LENGTH: 95
<212> TYPE: PRT
<213> ORGANISM: Artificial Sequence
<220> FEATURE:
<223> OTHER INFORMATION: IGKV1-39

<400> SEQUENCE: 99

Asp Ile Gln Met Thr Gln Ser Pro Ser Ser Leu Ser Ala Ser Val Gly
1               5                       10                      15

Asp Arg Val Thr Ile Thr Cys Arg Ala Ser Gln Ser Ile Ser Ser Tyr
              20                      25                      30

Leu Asn Trp Tyr Gln Gln Lys Pro Gly Lys Ala Pro Lys Leu Leu Ile
          35                      40                      45

Tyr Ala Ala Ser Ser Leu Gln Ser Gly Val Pro Ser Arg Phe Ser Gly
      50                      55                      60

Ser Gly Ser Gly Thr Asp Phe Thr Leu Thr Ile Ser Ser Leu Gln Pro
65                      70                      75                      80

Glu Asp Phe Ala Thr Tyr Tyr Cys Gln Gln Ser Tyr Ser Thr Pro
              85                      90                      95

<210> SEQ ID NO 100
<211> LENGTH: 108
<212> TYPE: PRT
<213> ORGANISM: Artificial Sequence
<220> FEATURE:
<223> OTHER INFORMATION: IGKV1-39/jk5

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
                100                 105

<210> SEQ ID NO 101
<211> LENGTH: 567
<212> TYPE: PRT
<213> ORGANISM: Artificial Sequence
<220> FEATURE:
<223> OTHER INFORMATION: Isoform A human TGF-BRII

<400> SEQUENCE: 101

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
                180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

```
Leu Leu Pro Ile Glu Leu Asp Thr Leu Val Gly Lys Gly Arg Phe Ala
            245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
            290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
            370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
            405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
            450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
            485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
            530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 102
<211> LENGTH: 144
<212> TYPE: PRT
<213> ORGANISM: Artificial Sequence
<220> FEATURE:
<223> OTHER INFORMATION: Extracellular domain of isoform A of human
      TGF-BRII

<400> SEQUENCE: 102

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30
```

```
Asp Val Arg Phe Ser Thr Cys Asp Asn Gln Lys Ser Cys Met Ser Asn
    35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
                100                 105                 110

Met Cys Ser Cys Ser Ser Asp Glu Cys Asn Asp Asn Ile Ile Phe Ser
                115                 120                 125

Glu Glu Tyr Asn Thr Ser Asn Pro Asp Leu Leu Leu Val Ile Phe Gln
    130                 135                 140
```

```
<210> SEQ ID NO 103
<211> LENGTH: 592
<212> TYPE: PRT
<213> ORGANISM: Artificial Sequence
<220> FEATURE:
<223> OTHER INFORMATION: Isoform B human TGF-BRII

<400> SEQUENCE: 103
```

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
    35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
                115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
                180                 185                 190

Thr Gly Ile Ser Leu Leu Pro Pro Leu Gly Val Ala Ile Ser Val Ile
                195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255
```

```
Ala Asn Asn Ile Asn His Asn Thr Glu Leu Leu Pro Ile Glu Leu Asp
            260             265             270

Thr Leu Val Gly Lys Gly Arg Phe Ala Glu Val Tyr Lys Ala Lys Leu
            275             280             285

Lys Gln Asn Thr Ser Glu Gln Phe Glu Thr Val Ala Val Lys Ile Phe
            290             295             300

Pro Tyr Glu Glu Tyr Ala Ser Trp Lys Thr Glu Lys Asp Ile Phe Ser
305             310             315             320

Asp Ile Asn Leu Lys His Glu Asn Ile Leu Gln Phe Leu Thr Ala Glu
            325             330             335

Glu Arg Lys Thr Glu Leu Gly Lys Gln Tyr Trp Leu Ile Thr Ala Phe
            340             345             350

His Ala Lys Gly Asn Leu Gln Glu Tyr Leu Thr Arg His Val Ile Ser
            355             360             365

Trp Glu Asp Leu Arg Lys Leu Gly Ser Ser Leu Ala Arg Gly Ile Ala
            370             375             380

His Leu His Ser Asp His Thr Pro Cys Gly Arg Pro Lys Met Pro Ile
385             390             395             400

Val His Arg Asp Leu Lys Ser Ser Asn Ile Leu Val Lys Asn Asp Leu
            405             410             415

Thr Cys Cys Leu Cys Asp Phe Gly Leu Ser Leu Arg Leu Asp Pro Thr
            420             425             430

Leu Ser Val Asp Asp Leu Ala Asn Ser Gly Gln Val Gly Thr Ala Arg
            435             440             445

Tyr Met Ala Pro Glu Val Leu Glu Ser Arg Met Asn Leu Glu Asn Val
            450             455             460

Glu Ser Phe Lys Gln Thr Asp Val Tyr Ser Met Ala Leu Val Leu Trp
465             470             475             480

Glu Met Thr Ser Arg Cys Asn Ala Val Gly Glu Val Lys Asp Tyr Glu
            485             490             495

Pro Pro Phe Gly Ser Lys Val Arg Glu His Pro Cys Val Glu Ser Met
            500             505             510

Lys Asp Asn Val Leu Arg Asp Arg Gly Arg Pro Glu Ile Pro Ser Phe
            515             520             525

Trp Leu Asn His Gln Gly Ile Gln Met Val Cys Glu Thr Leu Thr Glu
            530             535             540

Cys Trp Asp His Asp Pro Glu Ala Arg Leu Thr Ala Gln Cys Val Ala
545             550             555             560

Glu Arg Phe Ser Glu Leu Glu His Leu Asp Arg Leu Ser Gly Arg Ser
            565             570             575

Cys Ser Glu Glu Lys Ile Pro Glu Asp Gly Ser Leu Asn Thr Thr Lys
            580             585             590

<210> SEQ ID NO 104
<211> LENGTH: 169
<212> TYPE: PRT
<213> ORGANISM: Artificial Sequence
<220> FEATURE:
<223> OTHER INFORMATION: Extracellular domain of isoform B of human
      TGFR-BRII

<400> SEQUENCE: 104

Thr Ile Pro Pro His Val Gln Lys Ser Asp Val Glu Met Glu Ala Gln
1               5               10              15
```

-continued

```
Lys Asp Glu Ile Ile Cys Pro Ser Cys Asn Arg Thr Ala His Pro Leu
        20              25              30

Arg His Ile Asn Asn Asp Met Ile Val Thr Asp Asn Asn Gly Ala Val
        35              40              45

Lys Phe Pro Gln Leu Cys Lys Phe Cys Asp Val Arg Phe Ser Thr Cys
    50              55              60

Asp Asn Gln Lys Ser Cys Met Ser Asn Cys Ser Ile Thr Ser Ile Cys
65              70              75              80

Glu Lys Pro Gln Glu Val Cys Val Ala Val Trp Arg Lys Asn Asp Glu
                85              90              95

Asn Ile Thr Leu Glu Thr Val Cys His Asp Pro Lys Leu Pro Tyr His
        100             105             110

Asp Phe Ile Leu Glu Asp Ala Ala Ser Pro Lys Cys Ile Met Lys Glu
        115             120             125

Lys Lys Lys Pro Gly Glu Thr Phe Phe Met Cys Ser Cys Ser Ser Asp
    130             135             140

Glu Cys Asn Asp Asn Ile Ile Phe Ser Glu Glu Tyr Asn Thr Ser Asn
145             150             155             160

Pro Asp Leu Leu Leu Val Ile Phe Gln
                165
```

```
<210> SEQ ID NO 105
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 105

Asn Ala Trp Met Ser
1               5
```

```
<210> SEQ ID NO 106
<211> LENGTH: 19
<212> TYPE: PRT
<213> ORGANISM: Artificial Sequence
<220> FEATURE:
<223> OTHER INFORMATION: HCDR2 according to Kabat

<400> SEQUENCE: 106

Arg Ile Lys Thr Thr Ile Ser Gly Gly Ala Thr Gln Phe Ala Ala Pro
1               5               10              15

Val Lys Gly
```

```
<210> SEQ ID NO 107
<211> LENGTH: 5
<212> TYPE: PRT
<213> ORGANISM: Artificial Sequence
<220> FEATURE:
<223> OTHER INFORMATION: HCDR3 according to Kabat

<400> SEQUENCE: 107

Asp Leu Arg Asp Tyr
1               5
```

```
<210> SEQ ID NO 108
<211> LENGTH: 5
<212> TYPE: PRT
<213> ORGANISM: Artificial Sequence
<220> FEATURE:
<223> OTHER INFORMATION: HCDR1 according to Kabat
```

-continued

<400> SEQUENCE: 108

Arg Tyr Ala Met Ser
1               5

<210> SEQ ID NO 109
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 109

Ala Ile Ser Ala Gly Gly Asp Arg Thr Ala Asn Thr Asp Ser Val Lys
1               5                   10                  15

Gly

<210> SEQ ID NO 110
<211> LENGTH: 12
<212> TYPE: PRT
<213> ORGANISM: Artificial Sequence
<220> FEATURE:
<223> OTHER INFORMATION: HCDR3 according to Kabat

<400> SEQUENCE: 110

Gly Thr Ala Ala Arg Gly Lys Asn Tyr Phe Asp Pro
1               5                   10

<210> SEQ ID NO 111
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 111

Arg Tyr Ala Met Ser
1               5

<210> SEQ ID NO 112
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 112

Ala Ile Ser Ala Ser Gly Asp Arg Thr Lys Asn Thr Asp Ser Val Lys
1               5                   10                  15

Gly

<210> SEQ ID NO 113
<211> LENGTH: 12
<212> TYPE: PRT
<213> ORGANISM: Artificial Sequence
<220> FEATURE:
<223> OTHER INFORMATION: HCDR3 according to Kabat

<400> SEQUENCE: 113

Gly Thr Ala Ala Ala Gly Lys Asn Tyr Phe Asp Pro
1               5                   10

<210> SEQ ID NO 114
<211> LENGTH: 5
<212> TYPE: PRT

-continued

```
<213> ORGANISM: Artificial Sequence
<220> FEATURE:
<223> OTHER INFORMATION: HCDR1 according to Kabat

<400> SEQUENCE: 114

Arg Tyr Ala Met Ser
1               5

<210> SEQ ID NO 115
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 115

Ala Ile Ser Ala Ser Gly Asp Arg Tyr His Asn Thr Asp Ser Val Lys
1               5                   10                  15

Gly

<210> SEQ ID NO 116
<211> LENGTH: 12
<212> TYPE: PRT
<213> ORGANISM: Artificial Sequence
<220> FEATURE:
<223> OTHER INFORMATION: HCDR3 according to Kabat

<400> SEQUENCE: 116

Gly Thr Ala Ala Ser Gly Lys Asn Tyr Phe Asp Pro
1               5                   10

<210> SEQ ID NO 117
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 117

Arg Tyr Ala Met Ser
1               5

<210> SEQ ID NO 118
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 118

Ala Ile Ser Ala Ser Gly Asp Arg Thr His Asn Thr Asp Ser Val Lys
1               5                   10                  15

Gly

<210> SEQ ID NO 119
<211> LENGTH: 12
<212> TYPE: PRT
<213> ORGANISM: Artificial Sequence
<220> FEATURE:
<223> OTHER INFORMATION: HCDR3 according to Kabat

<400> SEQUENCE: 119

Gly Thr Ala Ala Arg Gly Lys Asn Tyr Phe Asp Pro
1               5                   10
```

-continued

```
<210> SEQ ID NO 120
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 120

Asn Tyr Trp Met Ser
1               5

<210> SEQ ID NO 121
<211> LENGTH: 19
<212> TYPE: PRT
<213> ORGANISM: Artificial Sequence
<220> FEATURE:
<223> OTHER INFORMATION: HCDR2 according to Kabat

<400> SEQUENCE: 121

Arg Ile Lys Thr Thr Tyr Ser Gly Gly Ala Thr Asp Phe Ala Ala Pro
1               5                   10                  15

Val Lys Gly

<210> SEQ ID NO 122
<211> LENGTH: 5
<212> TYPE: PRT
<213> ORGANISM: Artificial Sequence
<220> FEATURE:
<223> OTHER INFORMATION: HCDR3 according to Kabat

<400> SEQUENCE: 122

Asp Leu Arg Asp Tyr
1               5

<210> SEQ ID NO 123
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 123

Arg Tyr Ala Met Ser
1               5

<210> SEQ ID NO 124
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 124

Ser Ile Ser Ala Ser Gly Asp Arg Thr His Asn Thr Asp Ser Val Lys
1               5                   10                  15

Gly

<210> SEQ ID NO 125
<211> LENGTH: 12
<212> TYPE: PRT
<213> ORGANISM: Artificial Sequence
<220> FEATURE:
<223> OTHER INFORMATION: HCDR3 according to Kabat
```

-continued

<400> SEQUENCE: 125

Gly Leu Ala Ala Ser Gly Lys Asn Tyr Phe Asp Pro
1               5               10

<210> SEQ ID NO 126
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 126

Arg Tyr Ala Met Ser
1               5

<210> SEQ ID NO 127
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 127

Ala Ile Ser Ala Ser Gly Asp Arg Thr Asp Asn Thr Asp Ser Val Lys
1               5               10              15

Gly

<210> SEQ ID NO 128
<211> LENGTH: 12
<212> TYPE: PRT
<213> ORGANISM: Artificial Sequence
<220> FEATURE:
<223> OTHER INFORMATION: HCDR3 according to Kabat

<400> SEQUENCE: 128

Gly Ile Ala Arg Ser Gly Lys Asn Phe Phe Asp Pro
1               5               10

<210> SEQ ID NO 129
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 129

Arg Ala Trp Met Ser
1               5

<210> SEQ ID NO 130
<211> LENGTH: 19
<212> TYPE: PRT
<213> ORGANISM: Artificial Sequence
<220> FEATURE:
<223> OTHER INFORMATION: HCDR2 according to Kabat

<400> SEQUENCE: 130

Arg Ile Lys Thr Thr Ile Ser Gly Ala Ala Thr Asp Phe Ala Ala Pro
1               5               10              15

Val Lys Gly

<210> SEQ ID NO 131
<211> LENGTH: 5
<212> TYPE: PRT

<213> ORGANISM: Artificial Sequence
<220> FEATURE:
<223> OTHER INFORMATION: HCDR3 according to Kabat

<400> SEQUENCE: 131

Asp Leu Arg Asp Tyr
1               5

<210> SEQ ID NO 132
<211> LENGTH: 5
<212> TYPE: PRT
<213> ORGANISM: Artificial Sequence
<220> FEATURE:
<223> OTHER INFORMATION: HCDR1 according to Kabat

<400> SEQUENCE: 132

Arg Tyr Ala Met Ser
1               5

<210> SEQ ID NO 133
<211> LENGTH: 17
<212> TYPE: PRT
<213> ORGANISM: Artificial Sequence
<220> FEATURE:
<223> OTHER INFORMATION: HCDR2 according to Kabat

<400> SEQUENCE: 133

Ala Ile Ser Ala Ser Gly Asp Arg Thr Leu Asn Thr Asp Ser Val Lys
1               5                   10                  15

Gly

<210> SEQ ID NO 134
<211> LENGTH: 12
<212> TYPE: PRT
<213> ORGANISM: Artificial Sequence
<220> FEATURE:
<223> OTHER INFORMATION: HCDR3 according to Kabat

<400> SEQUENCE: 134

Gly Thr Ala Ala Arg Gly Lys Asn Tyr Phe Asp Pro
1               5                   10

<210> SEQ ID NO 135
<211> LENGTH: 107
<212> TYPE: PRT
<213> ORGANISM: Artificial Sequence
<220> FEATURE:
<223> OTHER INFORMATION: Light chain variable region

<400> SEQUENCE: 135

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
65              70              75              80

Glu Asp Phe Ala Val Tyr Tyr Cys Gln Gln Arg Ser Asn Trp Pro Pro
            85              90              95

Thr Phe Gly Gln Gly Thr Lys Val Glu Ile Lys
            100             105
```

```
<210> SEQ ID NO 136
<211> LENGTH: 125
<212> TYPE: PRT
<213> ORGANISM: Artificial Sequence
<220> FEATURE:
<223> OTHER INFORMATION: Heavy chain variable region

<400> SEQUENCE: 136

Glu Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Asn Tyr
            20              25              30

Gly Met His Trp Val Arg Gln Ala Pro Gly Lys Gly Leu Glu Trp Val
        35              40              45

Ala Val Ile Ser Tyr Asp Gly Ser Thr Lys Tyr Ser Ala Asp Ser Leu
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Asp Asp Thr Ala Val Tyr Tyr Cys
            85              90              95

Ala Lys Glu Gly Trp Ser Phe Asp Ser Ser Gly Tyr Arg Ser Trp Phe
            100             105             110

Asp Ser Trp Gly Gln Gly Thr Leu Val Thr Val Ser Ser
            115             120             125
```

The invention claimed is:

1. An antibody or antibody fragment thereof that specifically binds to the extracellular domain of human TGF-βRII, wherein the antibody or antibody fragment comprises any one of the heavy chain variable regions (VH) selected from:

a VH having
a VH-CDR1 comprising the amino acid sequence set forth in SEQ ID NO: 4,
a VH-CDR2 comprising the amino acid sequence set forth in SEQ ID NO: 5, and
a VH-CDR3 comprising the amino acid sequence set forth in SEQ ID NO: 6; or a VH having
a VH-CDR1 comprising the amino acid sequence set forth in SEQ ID NO: 7,
a VH-CDR2 comprising the amino acid sequence set forth in SEQ ID NO: 8, and
a VH-CDR3 comprising the amino acid sequence set forth in SEQ ID NO: 9,
wherein the antibody further comprises:
a light chain variable region (VL) having
a VL-CDR1 comprising the amino acid sequence set forth in SEQ ID NO: 19,
a VL-CDR2 comprising the amino acid sequence set forth in SEQ ID NO: 20, and
a VL-CDR3 comprising the amino acid sequence set forth in SEQ ID NO: 21.

2. The antibody or antibody fragment thereof of claim 1, wherein the antibody comprises a VH amino acid sequence selected from:

```
                                        (SEQ ID NO: 11)
QVQLVESGGGLVEPGGSLRLSCAASGFTFSNAWMSWVRQAPGKGLEWVG

RIKTTISGGATDFAAPVKGRFTISRDDSKNTLYLQMNSLKTEDTAVYYC

TLDLRDYWGQGTLVTVSS;

(SEQ ID NO: 12)
QVQLVESGGGLVQPGGSLRLSCAVSGFTFRRYAMSWVRQAPGKGLEWVS

AISASGDRTHNTDSVKGRFSISRDNSKNTLYLQMNSLRAEDTAVYFCAK

GIAASGKNYFDPWGQGTLVTVSS,
``` or a VH amino acid sequence having at least 80% identity thereto.

3. The antibody or antibody fragment thereof of claim 2, wherein the antibody comprises a VL amino acid sequence:
DIQMTQSPSSLSASVGDRVTITCRASQSIS-
SYLNWYQQKPGKAPKLLIYAASSLQSGV
PSRFSGSGSGTDFTLTISSLQPEDFATYYCQQSYS-
TPPTFGQGTKVEIK (SEQ ID NO: 16), or a VL amino acid sequence having at least 80% identity thereto.

4. The antibody of claim 1, which is an IgG antibody.

5. The antibody of claim 4, wherein the antibody is an IgG1 antibody or an IgG4 antibody.

6. The antibody of claim 5, wherein the antibody is an IgG1 antibody.

7. The antibody or antibody fragment thereof of claim 6, wherein the antibody or antibody fragment further comprises a heavy chain constant region comprising the amino acid sequence set forth in SEQ ID NO: 17.

8. The antibody or antibody fragment thereof of claim 7, wherein the antibody or antibody fragment further comprises a light chain constant region comprising the amino acid sequence set forth in SEQ ID NO: 18.

9. A pharmaceutical composition comprising the antibody or antibody fragment of claim 1 and a pharmaceutically acceptable carrier, diluent, or excipient.

10. The antibody or antibody fragment thereof of claim 1, wherein the antibody comprises a VH amino acid sequence selected from:

```
                                  (SEQ ID NO: 11)
QVQLVESGGGLVEPGGSLRLSCAASGFTFSNAWMSWVRQAPGKGLEWVG

RIKTTISGGATDFAAPVKGRFTISRDDSKNTLYLQMNSLKTEDTAVYYC

TLDLRDYWGQGTLVTVSS; or
                                  (SEQ ID NO: 12)
QVQLVESGGGLVQPGGSLRLSCAVSGFTFRRYAMSWVRQAPGKGLEWVS

AISASGDRTHNTDSVKGRFSISRDNSKNTLYLQMNSLRAEDTAVYFCAK

GIAASGKNYFDPWGQGTLVTVSS.
```

11. The antibody or antibody fragment thereof of claim 10, wherein the antibody comprises a VL amino acid sequence:

```
                                  (SEQ ID NO: 16)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPPTF

GQGTKVEIK.
```

12. An antibody or antibody fragment thereof that specifically binds to the extracellular domain of human TGF-βRII, wherein the antibody or antibody fragment comprises the VH-CDR1, VH-CDR2, and VH-CDR3 of a VH having an amino acid sequence set forth in any one of SEQ ID NO: 22-24, 26-28, 32, 39, 40, 42, 43, 48, 51-53, 56, 61, 63, 65, 70, 72, 74, 76, 79, 81, 87, 93,
    wherein the antibody further comprises a light chain variable region (VL) having
        a VL-CDR1 comprising the amino acid sequence set forth in SEQ ID NO: 19,
        a VL-CDR2 comprising the amino acid sequence set forth in SEQ ID NO: 20, and
        a VL-CDR3 comprising the amino acid sequence set forth in SEQ ID NO: 21.

13. The antibody or antibody fragment thereof of claim 12, wherein the antibody comprises a VH amino acid sequence selected from any one of SEQ ID NO: 22-24, 26-28, 32, 39, 40, 42, 43, 48, 51-53, 56, 61, 63, 65, 70, 72, 74, 76, 79, 81, 87, 93, or a VH amino acid sequence having at least 80%, 85%, 90%, 95%, 96%, 97%, 98%, or 99% identity thereto.

14. The antibody or antibody fragment thereof of claim 13, wherein the antibody comprises a VL amino acid sequence:

DIQMTQSPSSLSASVGDRVTITCRASQSIS-SYLNWYQQKPGKAPKLLIYAASSLQSGV PSRFSGSGSGTDFTLTISSLQPEDFATYYCQQSYS-TPPTFGQGTKVEIK (SEQ ID NO: 16), or a VL amino acid sequence having at least 80% identity thereto.

15. The antibody or antibody fragment thereof of claim 12, wherein the antibody comprises a VH amino acid sequence selected from any one of SEQ ID NO: 22-24, 26-28, 32, 39, 40, 42, 43, 48, 51-53, 56, 61, 63, 65, 70, 72, 74, 76, 79, 81, 87, or 93.

16. The antibody or antibody fragment thereof of claim 15, wherein the antibody comprises a VL amino acid sequence:

```
                                  (SEQ ID NO: 16)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPPTF

GQGTKVEIK.
```

17. A pharmaceutical composition comprising the antibody or antibody fragment of claim 12 and a pharmaceutically acceptable carrier, diluent, or excipient.

18. An antibody or antibody fragment thereof that specifically binds to the extracellular domain of human TGF-βRII, wherein the antibody comprises a VH amino acid sequence selected from SEQ ID NO: 67 or 83,
    wherein the antibody further comprises a light chain variable region (VL) having
        a VL-CDR1 comprising the amino acid sequence set forth in SEQ ID NO: 19,
        a VL-CDR2 comprising the amino acid sequence set forth in SEQ ID NO: 20, and
        a VL-CDR3 comprising the amino acid sequence set forth in SEQ ID NO: 21.

19. The antibody or antibody fragment thereof of claim 18, wherein the antibody comprises a VL amino acid sequence:
    DIQMTQSPSSLSASVGDRVTITCRASQSIS-SYLNWYQQKPGKAPKLLIYAASSLQSGV PSRFSGSGSGTDFTLTISSLQPEDFATYYCQQSYS-TPPTFGQGTKVEIK (SEQ ID NO: 16), or a VL amino acid sequence having at least 80% identity thereto.

20. The antibody or antibody fragment thereof of claim 18, wherein the antibody comprises a VL amino acid sequence:

```
                                  (SEQ ID NO: 16)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPPTF

GQGTKVEIK.
```

21. A pharmaceutical composition comprising the antibody or antibody fragment of claim 18 and a pharmaceutically acceptable carrier, diluent, or excipient.

22. An antibody that specifically binds to human TGF-βRII, wherein the antibody comprises:
    a heavy chain having a VH comprising the amino acid sequence set forth in any one selected from SEQ ID NOs: 10-12 and SEQ ID NOs: 22-24, 26-28, 32, 39, 40, 42, 43, 48, 51-53, 56, 61, 63, 65, 70, 72, 74, 76, 79, 81, 87, 93, and a heavy chain constant region comprising the amino acid sequence set forth in SEQ ID NO: 17; and a light chain having a VL comprising the amino acid sequence set forth in SEQ ID NO: 16, and a light chain constant region comprising the amino acid sequence set forth in SEQ ID NO: 18.

23. A pharmaceutical composition comprising the antibody or antibody fragment of claim 22 and a pharmaceutically acceptable carrier, diluent, or excipient.

24. An antibody that specifically binds to human TGF-βRII, wherein the antibody comprises:

a heavy chain having a VH comprising the amino acid sequence set forth in any one selected from SEQ ID NOs: 67 or 83, and a heavy chain constant region comprising the amino acid sequence set forth in SEQ ID NO: 17; and a light chain having a VL comprising the amino acid sequence set forth in SEQ ID NO: 16, and a light chain constant region comprising the amino acid sequence set forth in SEQ ID NO: 18.

25. A pharmaceutical composition comprising the antibody or antibody fragment of claim 24 and a pharmaceutically acceptable carrier, diluent, or excipient.

26. A binding domain that specifically binds to human TGF-βRII, wherein the binding domain comprises:

any one of the heavy chain variable regions (VH) selected from:

a VH having a VH-CDR1, VH-CDR2, and VH-CDR3 of the VH having an amino acid sequence set forth in SEQ ID NO: 12;

a VH having a VH-CDR1, VH-CDR2, and VH-CDR3 of the VH having an amino acid sequence set forth in SEQ ID NO: 26;

a VH having a VH-CDR1, VH-CDR2, and VH-CDR3 of the VH having an amino acid sequence set forth in SEQ ID NO: 40;

a VH having a VH-CDR1, VH-CDR2, and VH-CDR3 of the VH having an amino acid sequence set forth in SEQ ID NO: 61;

a VH having a VH-CDR1, VH-CDR2, and VH-CDR3 of the VH having an amino acid sequence set forth in SEQ ID NO: 65;

a VH having a VH-CDR1, VH-CDR2, and VH-CDR3 of the VH having an amino acid sequence set forth in SEQ ID NO: 70;

a VH having a VH-CDR1, VH-CDR2, and VH-CDR3 of the VH having an amino acid sequence set forth in SEQ ID NO: 76;

and wherein said binding domain further comprises:

a light chain variable region (VL) having a VL-CDR1 comprising the amino acid sequence set forth in SEQ ID NO: 19, a VL-CDR2 comprising the amino acid sequence set forth in SEQ ID NO: 20, and a VL-CDR3 comprising the amino acid sequence set forth in SEQ ID NO: 21.

27. The binding domain of claim 26, wherein the binding domain comprises a VH amino acid sequence selected from SEQ ID NOs: 12, 26, 40, 61, 65, 70, and 76, or a VH amino acid sequence having at least 80% identity thereto.

28. The binding domain of claim 27, wherein the antibody or binding domain comprises a VL amino acid sequence:
DIQMTQSPSSLSASVGDRVTITCRASQSIS-
SYLNWYQQKPGKAPKLLIYAASSLQSGV
PSRFSGSGSGTDFTLTISSLQPEDFATYYCQQSYS-
TPPTFGQGTKVEIK (SEQ ID NO: 16), or a VL amino acid sequence having at least 80% identity thereto.

29. A pharmaceutical composition comprising the binding domain of claim 26 and a pharmaceutically acceptable carrier, diluent, or excipient.

30. The binding domain of claim 26, wherein the binding domain comprises a VH amino acid sequence selected from SEQ ID NOs: 12, 26, 40, 61, 65, 70, and 76.

31. The binding domain of claim 30, wherein the antibody or binding domain comprises a VL amino acid sequence:

```
                                 (SEQ ID NO: 16)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPPTF

GQGTKVEIK.
```

32. An antibody or antibody fragment thereof that specifically binds to the extracellular domain of human TGF-βRII, wherein the antibody comprises a VH amino acid sequence as set forth in SEQ ID NO: 10, wherein the antibody further comprises a light chain variable region (VL) having a VL-CDR1 comprising the amino acid sequence set forth in SEQ ID NO: 19, a VL-CDR2 comprising the amino acid sequence set forth in SEQ ID NO: 20, and a VL-CDR3 comprising the amino acid sequence set forth in SEQ ID NO: 21.

33. The antibody or antibody fragment thereof of claim 32, wherein the antibody comprises a VL amino acid sequence:

```
                                 (SEQ ID NO: 16)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPPTF

GQGTKVEIK,
``` or a VL amino acid sequence having at least 80% identity thereto.

34. The antibody or antibody fragment thereof of claim 32, wherein the antibody comprises a VL amino acid sequence:

```
                                 (SEQ ID NO: 16)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPPTF

GQGTKVEIK.
```

35. A pharmaceutical composition comprising the antibody or antibody fragment of claim 32 and a pharmaceutically acceptable carrier, diluent, or excipient.

* * * * *